United States Patent
Nishimura et al.

[11] Patent Number: 5,861,284
[45] Date of Patent: Jan. 19, 1999

[54] METHOD FOR PRODUCING A BIOLOGICALLY ACTIVE RECOMBINANT CYSTEINE-FREE PARATHYROID HORMONE (1-34)

[75] Inventors: Osamu Nishimura, Kawanishi; Masato Kuriyama, Osaka; Nobuyuki Koyama, Suita; Tsunehiko Fukuda, Kyoto, all of Japan

[73] Assignee: Takeda Chemical Industries, Ltd., Osaka, Japan

[21] Appl. No.: 835,231

[22] Filed: Apr. 7, 1997

Related U.S. Application Data

[63] Continuation of Ser. No. 350,709, Dec. 7, 1994, abandoned, which is a continuation of Ser. No. 838,857, Feb. 18, 1992, abandoned.

[30] Foreign Application Priority Data

Feb. 19, 1991 [JP] Japan .................................. 3-024841
Oct. 18, 1991 [JP] Japan .................................. 3-271438
Oct. 24, 1991 [JP] Japan .................................. 3-277724

[51] Int. Cl.$^6$ .................................................. C12P 21/02
[52] U.S. Cl. ........................................ 435/69.4; 435/69.7
[58] Field of Search ................................. 435/69.4, 69.7

[56] References Cited

U.S. PATENT DOCUMENTS 5,426,036   6/1995   Koller et al. ........................... 435/69.7

FOREIGN PATENT DOCUMENTS

| | | |
|---|---|---|
| 121352 | 10/1984 | European Pat. Off. . |
| 281822A | 9/1988 | European Pat. Off. . |
| 0 293 158 | 11/1988 | European Pat. Off. .......... C07K 7/10 |
| 0 301 485 | 1/1989 | European Pat. Off. . |
| 0 301 485 | 2/1989 | European Pat. Off. ........ C12N 15/00 |
| 269072A | 6/1988 | Japan . |
| 84/03103 | 8/1984 | WIPO ............................ C12N 15/00 |
| 9013659 | 11/1990 | WIPO . |

OTHER PUBLICATIONS

Jacobson, et al., *J. of Bio. Chem.*, 243:19, pp. 6583–6591 (1973).
B. Merrifield, *Science*, vol. 232, pp. 341–347 (1986).
R.B. Merrifield, *Advances in Enzymology*, vol. 32, pp. 221–296 (1969).
Stark, "Cleavage at Cysteine After Cyanylation" *Meth. Enzymol.* 47:129–133, (1977).
Jambon et al. 1988 PNAS vol. 85 (24): pp. 9426–9430.
Lather et al. (1983), Genetic Engineering, Academic Press, pp. 31–50.
Smith et al. (1981), Genetic Engineering: Principles and Methods, vol. 3, pp. 1–32.
Koza, Seikagaku Biochemistry Experiments, Chemistry of Protein vol. 1, pp. 247–250 (1976) and an English translation thereof.
Science, vol. 198 p. 1056 (1977).
Nagai, et al. Methods in Enzymology, vol. 153, p. 46 (1987).

*Primary Examiner*—Elizabeth C. Kemmerer
*Attorney, Agent, or Firm*—David G. Conlin; David S. Resnick; Dike, Bronstein, Roberts & Cushman, LLP

[57] ABSTRACT

A cysteine-free peptide is produced by producing a fused protein comprising a protein having cysteine at its N-terminal and a cysteine-free peptide ligated to the N-terminal and subsequently subjecting the fused protein to a reaction for cleaving the peptide linkage.

1 Claim, 22 Drawing Sheets

```
             1                                                              15
         H-Tyr-Ala-Glu-Gly-Thr-Phe-Ile-Ser-Asp-Tyr-Ser-Ile-Ala-Met-Asp-

Lys-Ile-His-Gln-Gln-Asp-Phe-Val-Asn-Trp-Leu-Leu-Ala-Gln-Lys-
          16                                                              30

Gly-Lys-Lys-Asn-Asp-Trp-Lys-His-Asn-Ile-Thr-Gln-OH
              31                                                42
```

FIG. 2

```
                        H-His-Ala-Glu-Gly-Thr-Phe-Thr-Ser-Asp-Val-Ser-Ser-Tyr-
                             7           10              15              19

Leu-Glu-Gly-Gln-Ala-Ala-Lys-Glu-Phe-Ile-Ala-Trp-Leu-Val-Lys-Gly-Arg-Gly-OH
      20             25                  30                   35        37
```

FIG. 3

```
             1                                                              16
         H-Ser-Val-Ser-Glu-Ile-Gln-Leu-Met-His-Asn-Leu-Gly-Lys-His-Leu-Asn- 17                                                             32
         Ser-Met-Glu-Arg-Val-Glu-Trp-Leu-Arg-Lys-Lys-Leu-Gln-Asp-Val-His- 33 34
         Asn-Phe-OH
```

FIG. 4

```
    XbaI 1        10        20        30        40        50        60
    5'TCTAGATGTACGCGGAAGGGACTTTCATCAGTGACTACAGTATTGCCATGGACAAGATTCACCAACAAGAC (MetTyrAlaGluGlyThrPheIleSerAspTyrSerIleAlaMetAspLysIleHisGlnGlnAsp 70        80        90       100       110       120       130 AbaI
       TTTGTGAACTGGCTGCTGGCCCAAAAGGGGAAGAAGAATGACTGGAAACACAACATCACCCAGTGCCCCGAG 3'

PheValAsnTrpLeuLeuAlaGlnLysGlyLysLysAsnAspTrpLysHisAsnIleThrGlnCys)
```

FIG. 8

```
    1                            10                              20
H-MetTyrAlaGluGlyThrPheIleSerAspTyrSerIleAlaMetAspLysIleHisGln 30                              40
GlnAspPheValAsnTrpLeuLeuAlaGlnLysGlyLysLysAsnAspTrpLysHisAsn 50                              60
IleThrGln Cys ProGluAspGlyGlySerGlyAlaPheProProGlyHisPheLysAsp
GIP ←——|  |——→ hbFGF

ProLysArgLeuTyrCysLysAsnGlyGlyPhePheLeuArgIleHisProAspGlyArg

ValAspGlyValArgGluLysSerAspProHisIleLysLeuGlnLeuGlnAlaGluGlu-
```

FIG. 11

```
                                110                             120
ArgGlyValValSerIleLysGlyValSerAlaAsnArgTyrLeuAlaMetLysGluAsp 130                             140
GlyArgLeuLeuAlaSerLysSerValThrAspGluCysPhePhePheGluArgLeuGlu 150                             160
SerAsnAsnTyrAsnThrTyrArgSerArgLysTyrThrSerTrpTyrValAlaLeuLys 170                             180
ArgThrGlyGlnTyrLysLeuGlySerLysThrGlyProGlyGlnLysAlaIleLeuPhe

LeuProMetSerAlaLysSer-OH
```

FIG. 12

```
1   XbaI                     Met His Asp Glu Phe Glu Arg His Ala
1   TCT AGA AAG GAG ATA TAC ACT ATG CAC GAT GAA TTT GAA AGA CAT GCT
        ⌐——⌐

10  Glu Gly Thr Phe Thr Ser Asp Val Ser Ser Tyr Leu Glu Gly Gln Ala
49  GAA GGC ACC TTT ACC AGC GAT GTA AGC TCT TAT CTG GAA GGC CAG GCT

26  Ala Lys Glu Phe Ile Ala Trp Leu Val Lys Gly Arg Gly Cys Pro Glu
97  GCC AAA GAA TTC ATT GCT TGG CTG GTG AAA GGC CGT GGC TGC CCC GAG
                                                          ‾‾‾‾‾‾‾
                                                            AvaI
```

FIG. 16

```
Met His Ala Glu Gly Thr Phe Thr Ser Asp Val Ser Ser Tyr Leu Glu
 1            5                   10                  15

Gly Gln Ala Ala Lys Glu Phe Ile Ala Trp Leu Val Lys Gly Arg Gly
             20                  25                  30
                                            Insulinotropin ←

Cys Pro Glu Asp Gly Gly Ser Gly Ala Phe Pro Pro Gly His Phe Lys
     35                  40                  45
  → hbFGF

Asp Pro Lys Arg Leu Tyr Cys Lys Asn Gly Gly Phe Phe Leu Arg Ile
 50                  55                  60

His Pro Asp Gly Arg Val Asp Gly Val Arg Glu Lys Ser Asp Pro His
65                   70                  75                  80

Ile Lys Leu Gln Leu Gln Ala Glu Glu Arg Gly Val Val Ser Ile Lys
             85                  90                  95

Gly Val Ser Ala Asn Arg Tyr Leu Ala Met Lys Glu Asp Gly Arg Leu
             100                 105                 110

Leu Ala Ser Lys Ser Val Tyr Asp Glu Cys Phe Phe Phe Glu Arg Leu
             115                 120                 125

Glu Ser Asn Asn Tyr Asn Thr Tyr Arg Ser Arg Lys Tyr Thr Ser Trp
     130                 135                 140

Tyr Val Ala Leu Lys Arg Thr Gly Gln Tyr Lys Leu Gly Ser Lys Thr
145                 150                 155                 160

Gly Pro Gly Gln Lys Ala Ile Leu Phe Leu Pro Met Ser Ala Lys Ser-OH
                 165                 170                 175
```

FIG. 18

1   5'TATGTCTGTGTCCGAGATTCAGTTAATGCA3'
2   3'ACAGACACAGGCTCTAAGTCAATTACGTATTGGA5'

3   5'TAACCTTGGCAAACATTTGAACTCCATGGAGCGTGTAGAATGGCT3'
4   3'ACCGTTTGTAAACTTGAGGTACCTCGCACATCTTACCGACGCATT5'

5   5'GCGTAAGAAGTTGCAGGATGTGCACAATTT3'
6   3'CTTCAACGTCCTACACGTGTTAAAACAACG5'

7   5'TGTTGCCTTAGGTGCCCCATTGGCTCCTCGTGATGCTGGTTCCCAA3'
8   3'GAATCCACGGGGTAACCGAGGAGCACTACGACCAAGGGTTTCTGGT5'

9   5'AGACCACGTAAAAAGGAAGACAATGTCTTAGTTGAGAGCCA3'
10  3'GCATTTTTCCTTCTGTTACAGAATCAACTCTCGGTACTTTT5'

11  5'TGAAAAATCCCTAGGCGAGGCAGACAAGGCCGATGTGAATGT3'
12  3'TAGGGATCCGCTCCGTCTGTTCCGGCTACACTTACATAATTG5'

13  5'ATTAACTAAAGCTAAATCCCAGTAATGAG3'
14  3'ATTTCGATTTAGGGTCATTACTCCTAG5'

FIG. 19

TCT.GTG.TCC.GAG.ATT.CAG.TTA.ATG.CAT.AAC.CTT.GGC.AAA.CAT.TTG.AAC.TCC.ATG.GAG
Ser-Val-Ser-Glu-Ile-Gln-Leu-Met-His-Asn-Leu-Gly-Lys-His-Leu-Asn-Ser-Met-Glu

CGT.GTA.GAA.TGG.CTG.CGT.AAG.AAG.TTG.CAG.GAT.GTG.CAC.AAT.TTT.TGC.GCC.TTA.GGT.GCC
Arg-Val-Glu-Trp-Leu-Arg-Lys-Lys-Leu-Gln-Asp-Val-His-Asn-Phe-Cys-Ala-Leu-Gly-Ala

CCA.TTG.GCT.CCT.CGT.GAT.CCT.GGT.TCC.CAA.AGA.CCA.CGT.AAA.AAG.GAA.GAC.AAT.GTC.TTA
Pro-Leu-Ala-Pro-Arg-Asp-Ala-Gly-Ser-Gln-Arg-Pro-Arg-Lys-Lys-Glu-Asp-Asn-Val-Leu

GTT.GAG.AGC.CAT.GAA.AAA.TCC.CTA.GGC.GAG.GCA.GAC.AAG.GCC.GAT.GTG.AAT.GTA.TTA.ACT
Val-Glu-Ser-His-Glu-Lys-Ser-Leu-Gly-Glu-Ala-Asp-Lys-Ala-Asp-Val-Asn-Val-Leu-Thr

AAA.GCT.AAA.TCC.CAG
Lys-Ala-Lys-Ser-Gln

FIG. 25

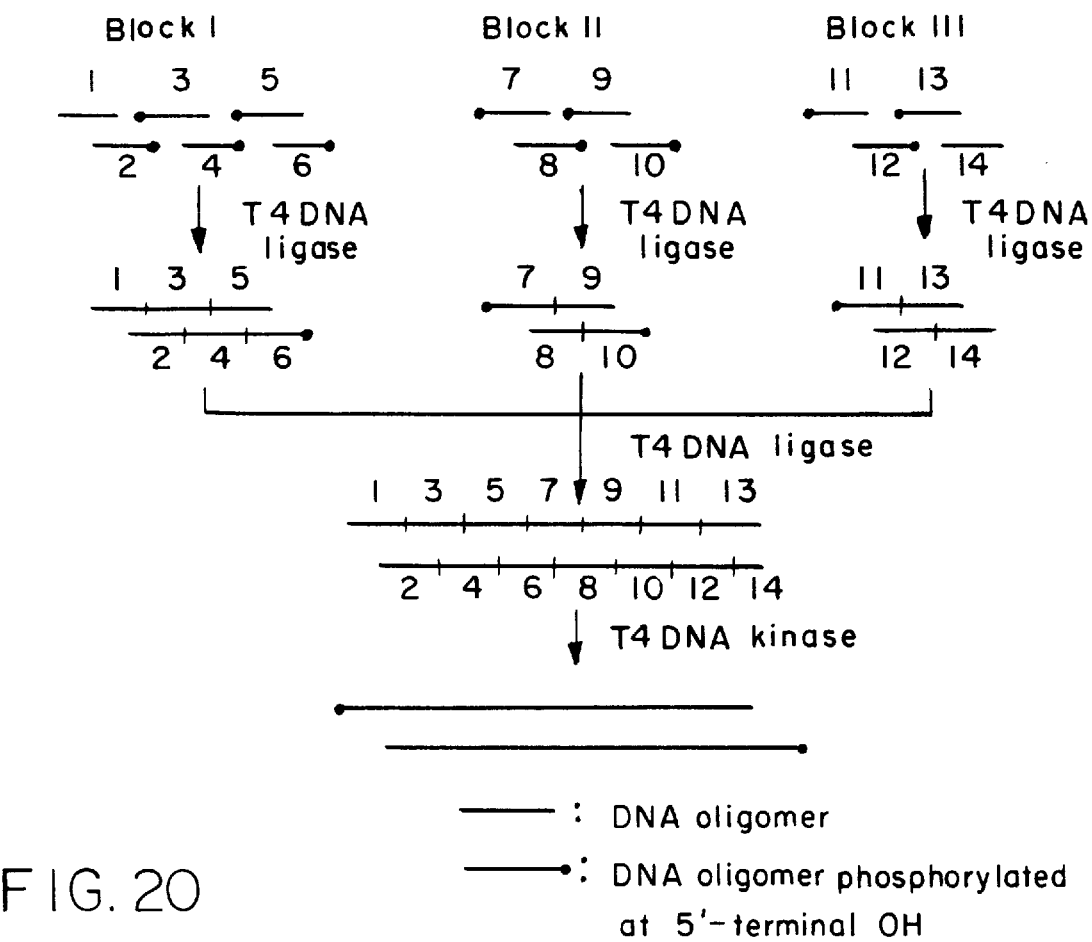
F I G. 20
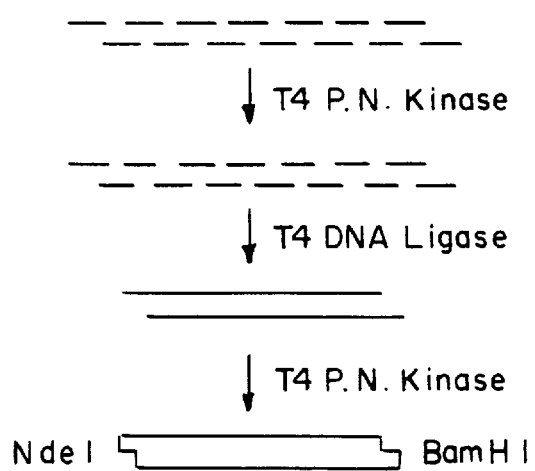
F I G. 21

SEQUENCE LISTING ( 1 ) GENERAL INFORMATION:

( i i i ) NUMBER OF SEQUENCES: 37

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) FEATURE:
        ( A ) NAME/KEY: Protein
        ( B ) LOCATION: 1
        ( C ) OTHER INFORMATION: /note ="Xaa = D-Leucine"

( v i i ) ORIGINAL SOURCE:

( x i ) SEQUENCE DESCRIPTION: SEQ ID NO:1:

Xaa Leu Leu Arg Pro
1               5

( 2 ) INFORMATION FOR SEQ ID NO:2:

( i ) SEQUENCE CHARACTERISTICS:

(A) LENGTH: 11 amino acids
                (B) TYPE: amino acid
                (C) STRANDEDNESS: single
                (D) TOPOLOGY: linear (ii) MOLECULE TYPE: peptide (iii) HYPOTHETICAL: NO (iv) ANTI-SENSE: NO (vi) FEATURE:
                (A) NAME/KEY: Protein
                (B) LOCATION: 4
                (C) OTHER INFORMATION: /note ="Xaa = D-Alanine"

(v) FRAGMENT TYPE: N-terminal (vi) ORIGINAL SOURCE:

(xi) SEQUENCE DESCRIPTION: SEQ ID NO:2:

Val Ala Leu Xaa Ala Ala Pro Leu Ala Pro Arg
 1           5                   10

(2) INFORMATION FOR SEQ ID NO:3:

(i) SEQUENCE CHARACTERISTICS:
                (A) LENGTH: 561 base pairs
                (B) TYPE: nucleic acid
                (C) STRANDEDNESS: double
                (D) TOPOLOGY: linear (ii) MOLECULE TYPE: Synthetic DNA (iii) HYPOTHETICAL: NO (iv) ANTI-SENSE: NO (v) FRAGMENT TYPE:

(vi) ORIGINAL SOURCE:
                (A) ORGANISM: Synthetic DNA (xi) SEQUENCE DESCRIPTION: SEQ ID NO:3:

| TACGCGGAAG | GGACTTTCAT | CAGTGACTAC | AGTATTGCCA | TGGACAAGAT | TCACCAACAA | 60 |
| GACTTTGTGA | ACTGGCTGCT | GGCCCAAAAG | GGGAAGAAGA | ATGACTGGAA | ACACAACATC | 120 |
| ACCCAGTGCC | CCGAGGATGG | CGGCAGCGGC | GCCTTCCCGC | CCGGCCACTT | CAAGGACCCC | 180 |
| AAGCGGCTGT | ACTGCAAAAA | CGGGGGCTTC | TTCCTGCGCA | TCCACCCCGA | CGGCCGAGTT | 240 |
| GACGGGGTCC | GGGAGAAGAG | CGACCCTCAC | ATCAAGCTAC | AACTTCAAGC | AGAAGAGAGA | 300 |
| GGAGTTGTGT | CTATCAAAGG | AGTGAGCGCT | AATCGTTACC | TGGCTATGAA | GGAAGATGGA | 360 |
| AGATTACTAG | CTTCTAAGTC | TGTTACGGAT | GAGTGTTTCT | TTTTGAACG | ATTGGAATCT | 420 |
| AATAACTACA | ATACTTACCG | GTCAAGGAAA | TACACCAGTT | GGTATGTGGC | ACTGAAACGA | 480 |
| ACTGGGCAGT | ATAAACTTGG | ATCCAAAACA | GGACCTGGGC | AGAAAGCTAT | ACTTTTTCTT | 540 |
| CCAATGTCTG | CTAAGAGCTG | C | | | | 561 |

(2) INFORMATION FOR SEQ ID NO:4:

(i) SEQUENCE CHARACTERISTICS:
                (A) LENGTH: 561 base pairs
                (B) TYPE: nucleic acid
                (C) STRANDEDNESS: double
                (D) TOPOLOGY: linear (ii) MOLECULE TYPE: Synthetic DNA (iii) HYPOTHETICAL: NO (iv) ANTI-SENSE: NO (v) FRAGMENT TYPE:

(vi) ORIGINAL SOURCE:
    (A) ORGANISM: Synthetic DNA (xi) SEQUENCE DESCRIPTION: SEQ ID NO:4:

```
TACGCGGAAG GGACTTTCAT CAGTGACTAC AGTATTGCCA TGGACAAGAT TCACCAACAA      60
GACTTTGTGA ACTGGCTGCT GGCCCAAAAG GGGAAGAAGA ATGACTGGAA ACACAACATC     120
ACCCAGTGTC CGAGGATGG  CGGCAGCGGC GCCTTCCCGC CGGCCACTT  CAAGGACCCC     180
AAGCGGCTGT ACTGCAAAAA CGGGGGCTTC TTCCTGCGCA TCCACCCCGA CGGCCGAGTT     240
GACGGGGTCC GGGAGAAGAG CGACCCTCAC ATCAAGCTAC AACTTCAAGC AGAAGAGAGA     300
GGAGTTGTGT CTATCAAAGG AGTGAGCGCT AATCGTTACC TGGCTATGAA GGAAGATGGA     360
AGATTACTAG CTTCTAAGTC TGTTACGGAT GAGTGTTTCT TTTTTGAACG ATTGGAATCT     420
AATAACTACA ATACTTACCG GTCAAGGAAA TACACCAGTT GGTATGTGGC ACTGAAACGA     480
ACTGGGCAGT ATAAACTTGG ATCCAAAACA GGACCTGGGC AGAAAGCTAT ACTTTTTCTT     540
CCAATGTCTG CTAAGAGCTG C                                               561
```

(2) INFORMATION FOR SEQ ID NO:5:

(i) SEQUENCE CHARACTERISTICS:
    (A) LENGTH: 537 base pairs
    (B) TYPE: nucleic acid
    (C) STRANDEDNESS: double
    (D) TOPOLOGY: linear (ii) MOLECULE TYPE: Synthetic DNA (iii) HYPOTHETICAL: NO (iv) ANTI-SENSE: NO (v) FRAGMENT TYPE:

(vi) ORIGINAL SOURCE:
    (A) ORGANISM: Synthetic DNA (xi) SEQUENCE DESCRIPTION: SEQ ID NO:5:

```
TCTGTGAGTG AAATACAGCT TATGCATAAC CTGGGAAAAC ATCTGAACTC GATGGAGAGA      60
GTAGAATGGC TGCGTAAGAA GCTGCAGGAT GTGCACAATT TTTGTCCCGA GGATGGCGGC     120
AGCGGCGCCT TCCCGCCCGG CCACTTCAAG GACCCCAAGC GGCTGTACTG CAAAAACGGG     180
GGCTTCTTCC TGCGCATCCA CCCCGACGGC CGAGTTGACG GGTCCGGGA  GAAGAGCGAC     240
CCTCACATCA AGCTACAACT TCAAGCAGAA GAGAGGAG   TTGTGTCTAT CAAAGGAGTG     300
AGCGCTAATC GTTACCTGGC TATGAAGGAA GATGGAAGAT TACTAGCTTC TAAGTCTGTT     360
ACGGATGAGT GTTTCTTTTT TGAACGATTG GAATCTAATA ACTACAATAC TTACCGGTCA     420
AGGAAATACA CCAGTTGGTA TGTGGCACTG AAACGAACTG GCAGTATAA  ACTTGGATCC     480
AAAACAGGAC CTGGGCAGAA AGCTATACTT TTTCTTCCAA TGTCTGCTAA GAGCTGC        537
```

(2) INFORMATION FOR SEQ ID NO:6:

(i) SEQUENCE CHARACTERISTICS:
    (A) LENGTH: 537 base pairs
    (B) TYPE: nucleic acid
    (C) STRANDEDNESS: double
    (D) TOPOLOGY: linear (ii) MOLECULE TYPE: Synthetic DNA ( i i i ) HYPOTHETICAL: NO ( i v ) ANTI-SENSE: NO ( v ) FRAGMENT TYPE:

( v i ) ORIGINAL SOURCE:
    ( A ) ORGANISM: Synthetic DNA ( x i ) SEQUENCE DESCRIPTION: SEQ ID NO:6:

| TCTGTGAGTG | AAATACAGCT | TATGCATAAC | CTGGGAAAAC | ATCTGAACTC | GATGGAGAGA | 60 |
| GTAGAATGGC | TGCGTAAGAA | GCTGCAGGAT | GTGCACAATT | TTTGTCCCGA | GGATGGCGGC | 120 |
| AGCGGCGCCT | TCCCGCCCGG | CCACTTCAAG | GACCCCAAGC | GGCTGTACTG | CAAAAACGGG | 180 |
| GGCTTCTTCC | TGCGCATCCA | CCCCGACGGC | CGAGTTGACG | GGGTCCGGGA | GAAGAGCGAC | 240 |
| CCTCACATCA | AGCTACAACT | TCAAGCAGAA | GAGAGAGGAG | TTGTGTCTAT | CAAAGGAGTG | 300 |
| AGCGCTAATC | GTTACCTGGC | TATGAAGGAA | GATGGAAGAT | TACTAGCTTC | TAAGTCTGTT | 360 |
| ACGGATGAGT | GTTTCTTTTT | TGAACGATTG | GAATCTAATA | ACTACAATAC | TTACCGGTCA | 420 |
| AGGAAATACA | CCAGTTGGTA | TGTGGCACTG | AAACGAACTG | GGCAGTATAA | ACTTGGATCC | 480 |
| AAAACAGGAC | CTGGGCAGAA | AGCTATACTT | TTTCTTCCAA | TGTCTGCTAA | GAGCTGC | 537 |

( 2 ) INFORMATION FOR SEQ ID NO:7:

( i ) SEQUENCE CHARACTERISTICS:
    ( A ) LENGTH: 528 base pairs
    ( B ) TYPE: nucleic acid
    ( C ) STRANDEDNESS: double
    ( D ) TOPOLOGY: linear ( i i ) MOLECULE TYPE: Synthetic DNA ( i i i ) HYPOTHETICAL: NO ( i v ) ANTI-SENSE: NO ( v ) FRAGMENT TYPE:

( v i ) ORIGINAL SOURCE:
    ( A ) ORGANISM: Synthetic DNA ( x i ) SEQUENCE DESCRIPTION: SEQ ID NO:7:

| CATGCTGAAG | GGACCTTTAC | GAGTGATGTA | AGTTCTTATT | TGGAAGGCCA | AGCTGCCAAG | 60 |
| GAATTCATTG | CTTGGCTGGT | GAAAGGCCGA | GGATGCCCCG | AGGATGGCGG | CAGCGGCGCC | 120 |
| TTCCCGCCCG | GCCACTTCAA | GGACCCCAAG | CGGCTGTACT | GCAAAAACGG | GGGCTTCTTC | 180 |
| CTGCGCATCC | ACCCCGACGG | CCGAGTTGAC | GGGGTCCGGG | AGAAGAGCGA | CCCTCACATC | 240 |
| AAGCTACAAC | TTCAAGCAGA | AGAGAGAGGA | GTTGTGTCTA | TCAAAGGAGT | GAGCGCTAAT | 300 |
| CGTTACCTGG | CTATGAAGGA | AGATGGAAGA | TTACTAGCTT | CTAAGTCTGT | TACGGATGAG | 360 |
| TGTTTCTTTT | TTGAACGATT | GGAATCTAAT | AACTACAATA | CTTACCGGTC | AAGGAAATAC | 420 |
| ACCAGTTGGT | ATGTGGCACT | GAAACGAACT | GGGCAGTATA | AACTTGGATC | CAAAACAGGA | 480 |
| CCTGGGCAGA | AAGCTATACT | TTTTCTTCCA | ATGTCTGCTA | AGAGCTGC | | 528 |

( 2 ) INFORMATION FOR SEQ ID NO:8:

( i ) SEQUENCE CHARACTERISTICS:
    ( A ) LENGTH: 528 base pairs
    ( B ) TYPE: nucleic acid
    ( C ) STRANDEDNESS: double
    ( D ) TOPOLOGY: linear ( i i ) MOLECULE TYPE: Synthetic DNA ( i i i ) HYPOTHETICAL: NO ( i v ) ANTI-SENSE: NO ( v ) FRAGMENT TYPE:

( v i ) ORIGINAL SOURCE:
    ( A ) ORGANISM: Synthetic DNA ( x i ) SEQUENCE DESCRIPTION: SEQ ID NO:8:

```
CATGCTGAAG  GGACCTTTAC  CAGTGATGTA  AGTTCTTATT  TGGAAGGCCA  AGCTGCCAAG      60
GAATTCATTG  CTTGGCTGGT  GAAAGGCCGA  GGATGTCCCG  AGGATGGCGG  CAGCGGCGCC     120
TTCCCGCCCG  GCCACTTCAA  GGACCCCAAG  CGGCTGTACT  GCAAAAACGG  GGGCTTCTTC     180
CTGCGCATCC  ACCCCGACGG  CCGAGTTGAC  GGGGTCCGGG  AGAAGAGCGA  CCCTCACATC     240
AAGCTACAAC  TTCAAGCAGA  AGAGAGAGGA  GTTGTGTCTA  TCAAAGGAGT  GAGCGCTAAT     300
CGTTACCTGG  CTATGAAGGA  AGATGGAAGA  TTACTAGCTT  CTAAGTCTGT  TACGGATGAG     360
TGTTTCTTTT  TTGAACGATT  GGAATCTAAT  AACTACAATA  CTTACCGGTC  AAGGAAATAC     420
ACCAGTTGGT  ATGTGGCACT  GAAACGAACT  GGGCAGTATA  AACTTGGATC  CAAAACAGGA     480
CCTGGGCAGA  AAGCTATACT  TTTTCTTCCA  ATGTCTGCTA  AGAGCTGC                   528
```

( 2 ) INFORMATION FOR SEQ ID NO:9:

( i ) SEQUENCE CHARACTERISTICS:
        ( A ) LENGTH: 84 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:9:

```
Ser  Val  Ser  Glu  Ile  Gln  Leu  Met  His  Asn  Leu  Gly  Lys  His  Leu  Asn
 1             5                      10                      15
Ser  Met  Glu  Arg  Val  Glu  Trp  Leu  Arg  Lys  Lys  Leu  Gln  Asp  Val  His
                20                      25                      30
Asn  Phe  Val  Ala  Leu  Gly  Ala  Pro  Leu  Ala  Pro  Arg  Asp  Ala  Gly  Ser
                35                      40                      45
Gln  Arg  Pro  Arg  Lys  Lys  Glu  Asp  Asn  Val  Leu  Val  Glu  Ser  His  Glu
         50                      55                      60
Lys  Ser  Leu  Gly  Glu  Ala  Asp  Lys  Ala  Asp  Val  Asn  Val  Leu  Thr  Lys
 65                      70                      75                      80
Ala  Lys  Ser  Gln
```

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Synthetic DNA ( i i i ) HYPOTHETICAL: NO (i v) ANTI-SENSE: NO (v) FRAGMENT TYPE:

(v i) ORIGINAL SOURCE:
    (A) ORGANISM: Synthetic DNA (x i) SEQUENCE DESCRIPTION: SEQ ID NO:10:

CACAATTTTT GCGCCTTAGG                        20

(2) INFORMATION FOR SEQ ID NO:11:

(i) SEQUENCE CHARACTERISTICS:
        (A) LENGTH: 42 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: N-terminal (v i) ORIGINAL SOURCE:

(x i) SEQUENCE DESCRIPTION: SEQ ID NO:11:

Tyr Ala Glu Gly Thr Phe Ile Ser Asp Tyr Ser Ile Ala Met Asp Lys
 1               5                  10                  15

Ile His Gln Gln Asp Phe Val Asn Trp Leu Leu Xaa Gln Lys Gly Lys
                20                  25                  30

Lys Asn Asp Trp Lys His Asn Ile Thr Gln
                35                  40

(2) INFORMATION FOR SEQ ID NO:12:

(i) SEQUENCE CHARACTERISTICS:
        (A) LENGTH: 31 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: N-terminal (v i) ORIGINAL SOURCE:

(x i) SEQUENCE DESCRIPTION: SEQ ID NO:12:

His Ala Gln Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Gly
                20                  25                  30

(2) INFORMATION FOR SEQ ID NO:13:

(i) SEQUENCE CHARACTERISTICS:
        (A) LENGTH: 34 amino acids
        (B) TYPE: amino acid
        (C) STRANDEDNESS: single
        (D) TOPOLOGY: linear (i i) MOLECULE TYPE: peptide (i i i) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:13:

| Ser | Val | Ser | Glu | Ile | Gln | Leu | Met | His | Asn | Leu | Gly | Lys | His | Leu | Asn |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Met | Glu | Arg | Val | Glu | Trp | Leu | Arg | Lys | Lys | Leu | Gln | Asp | Val | His |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

Asn Phe (2) INFORMATION FOR SEQ ID NO:14:

(i) SEQUENCE CHARACTERISTICS:
(A) LENGTH: 143 base pairs
(B) TYPE: nucleic acid
(C) STRANDEDNESS: double
(D) TOPOLOGY: linear (ii) MOLECULE TYPE: Synthetic DNA (iii) HYPOTHETICAL: NO (iv) ANTI-SENSE: NO (v) FRAGMENT TYPE:

(vi) ORIGINAL SOURCE:
(A) ORGANISM: Synthetic DNA (ix) FEATURE:
(A) NAME/KEY: Coding Sequence
(B) LOCATION: 6...137

(xi) SEQUENCE DESCRIPTION: SEQ ID NO:14:

```
TCTAG ATG TAC GCG GAA GGG ACT TTC ATC AGT GAC TAC AGT ATT GCC ATG      50
      Met Tyr Ala Glu Gly Thr Phe Ile Ser Asp Tyr Ser Ile Ala Met
      1               5                   10                  15

GAC AAG ATT CAC CAA CAA GAC TTT GTG AAC TGG CTG CTG GCC CAA AAG        98
Asp Lys Ile His Gln Gln Asp Phe Val Asn Trp Leu Leu Ala Gln Lys
                20                  25                  30

GGG AAG AAG AAT GAC TGG AAA CAC AAC ATC ACC CAG TGC CCCGAG            143
Gly Lys Lys Asn Asp Trp Lys His Asn Ile Thr Gln Cys
            35                  40
```

(2) INFORMATION FOR SEQ ID NO:15:

(i) SEQUENCE CHARACTERISTICS:
(A) LENGTH: 159 base pairs
(B) TYPE: nucleic acid
(C) STRANDEDNESS: double
(D) TOPOLOGY: linear (ii) MOLECULE TYPE: Synthetic DNA (iii) HYPOTHETICAL: NO (iv) ANTI-SENSE: NO (v) FRAGMENT TYPE:

(vi) ORIGINAL SOURCE:
(A) ORGANISM: Synthetic DNA (xi) SEQUENCE DESCRIPTION: SEQ ID NO:15:

```
TCTAGAAAGG AGATATACAC TATGTACGCG GAAGGGACTT TCATCAGTGA CTACAGTATT      60

GCCATGGACA AGATTCACCA ACAAGACTTT GTGAACTGGC TGCTGGCCCA AAAGGGGAAG     120
```

AAGAATGACT GGAAACACAA CATCACCCAG TGCCCCGAG 159

( 2 ) INFORMATION FOR SEQ ID NO:16:

( i ) SEQUENCE CHARACTERISTICS:
        ( A ) LENGTH: 187 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:16:

| Met | Tyr | Ala | Glu | Gly | Thr | Phe | Ile | Ser | Asp | Tyr | Ser | Ile | Ala | Met | Asp |
|---|---|---|---|---|---|---|---|---|---|---|---|---|---|---|---|
| 1 | | | | 5 | | | | | 10 | | | | | 15 | |
| Lys | Ile | His | Gln | Gln | Asp | Phe | Val | Asn | Trp | Leu | Leu | Ala | Gln | Lys | Gly |
| | | | 20 | | | | | 25 | | | | | 30 | | |
| Lys | Lys | Asn | Asp | Trp | Lys | His | Asn | Ile | Thr | Gln | Cys | Pro | Glu | Asp | Gly |
| | | 35 | | | | | 40 | | | | | 45 | | | |
| Gly | Ser | Gly | Ala | Phe | Pro | Pro | Gly | His | Phe | Lys | Asp | Pro | Lys | Arg | Leu |
| | 50 | | | | | 55 | | | | | 60 | | | | |
| Tyr | Cys | Lys | Asn | Gly | Gly | Phe | Phe | Leu | Arg | Ile | His | Pro | Asp | Gly | Arg |
| 65 | | | | | 70 | | | | | 75 | | | | | 80 |
| Val | Asp | Gly | Val | Arg | Glu | Lys | Ser | Asp | Pro | His | Ile | Lys | Leu | Gln | Leu |
| | | | | 85 | | | | | 90 | | | | | 95 | |
| Gln | Ala | Glu | Glu | Arg | Gly | Val | Val | Ser | Ile | Lys | Gly | Val | Ser | Ala | Asn |
| | | | 100 | | | | | 105 | | | | | 110 | | |
| Arg | Tyr | Leu | Ala | Met | Lys | Glu | Asp | Gly | Arg | Leu | Leu | Ala | Ser | Lys | Ser |
| | | 115 | | | | | 120 | | | | | 125 | | | |
| Val | Thr | Asp | Glu | Cys | Phe | Phe | Phe | Glu | Arg | Leu | Glu | Ser | Asn | Asn | Tyr |
| | 130 | | | | | 135 | | | | | 140 | | | | |
| Asn | Thr | Tyr | Arg | Ser | Arg | Lys | Tyr | Tyr | Ser | Trp | Tyr | Val | Ala | Leu | Lys |
| 145 | | | | | 150 | | | | | 155 | | | | | 160 |
| Arg | Thr | Gly | Gln | Tyr | Lys | Leu | Gly | Ser | Lys | Thr | Gly | Pro | Gly | Gln | Lys |
| | | | | 165 | | | | | 170 | | | | | 175 | |
| Ala | Ile | Leu | Phe | Leu | Pro | Met | Ser | Ala | Lys | Ser | | | | | |
| | | | 180 | | | | | 185 | | | | | | | |

( 2 ) INFORMATION FOR SEQ ID NO:17:

( i ) SEQUENCE CHARACTERISTICS:
        ( A ) LENGTH: 144 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( i x ) FEATURE:

( A ) NAME/KEY: Coding Sequence
( B ) LOCATION: 22...144

( x i ) SEQUENCE DESCRIPTION: SEQ ID NO:17:

```
TCTAGAAAGG AGATATACAC T ATG CAC GAT GAA TTT GAA AGA CAT GCT GAA        51
                        Met His Asp Glu Phe Glu Arg His Ala Glu
                         1               5                  10

GGC ACC TTT ACC AGC GAT GTA AGC TCT TAT CTG GAA GGC CAG GCT GCC        99
Gly Thr Phe Thr Ser Asp Val Ser Ser Tyr Leu Glu Gly Gln Ala Ala
                 15                  20                  25

AAA GAA TTC ATT GCT TGG CTG GTG AAA GGC CGT GGC TGC CCC GAG           144
Lys Glu Phe Ile Ala Trp Leu Val Lys Gly Arg Gly Cys Pro Glu
             30                  35                  40
```

( 2 ) INFORMATION FOR SEQ ID NO:18:

( i ) SEQUENCE CHARACTERISTICS:
    ( A ) LENGTH: 176 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:18:

```
Met His Ala Glu Gly Thr Phe Thr Ser Asp Val Ser Ser Tyr Leu Glu
 1               5                  10                  15

Gly Gln Ala Ala Lys Glu Phe Ile Ala Trp Leu Val Lys Gly Arg Gly
             20                  25                  30

Cys Pro Glu Asp Gly Gly Ser Gly Ala Phe Pro Pro Gly His Phe Lys
         35                  40                  45

Asp Pro Lys Arg Leu Tyr Cys Lys Asn Gly Gly Phe Phe Leu Arg Ile
     50                  55                  60

His Pro Asp Gly Arg Val Asp Gly Val Arg Glu Lys Ser Asp Pro His
65                  70                  75                  80

Ile Lys Leu Gln Leu Gln Ala Gln Gln Arg Gly Val Val Ser Ile Lys
                 85                  90                  95

Gly Val Ser Ala Asn Arg Tyr Leu Ala Met Lys Glu Asp Gly Arg Leu
            100                 105                 110

Leu Ala Ser Lys Ser Val Tyr Asp Glu Cys Phe Phe Glu Arg Leu
        115                 120                 125

Glu Ser Asn Asn Tyr Asn Thr Tyr Arg Ser Arg Lys Tyr Thr Ser Trp
    130                 135                 140

Tyr Val Ala Leu Lys Arg Thr Gly Gln Tyr Lys Leu Gly Ser Lys Thr
145                 150                 155                 160

Gly Pro Gly Gln Lys Ala Ile Leu Phe Leu Pro Met Ser Ala Lys Ser
                165                 170                 175
```

( 2 ) INFORMATION FOR SEQ ID NO:19:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: Synthetic DNA ( i i i ) HYPOTHETICAL: NO ( i v ) ANTI-SENSE: NO ( v ) FRAGMENT TYPE:

( v i ) ORIGINAL SOURCE:
    ( A ) ORGANISM: Synthetic DNA ( x i ) SEQUENCE DESCRIPTION: SEQ ID NO:19:

TATGTCTGTG TCCGAGATTC AGTTAATGCA 30

( 2 ) INFORMATION FOR SEQ ID NO:20:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: Synthetic DNA ( i i i ) HYPOTHETICAL: NO ( i v ) ANTI-SENSE: NO ( v ) FRAGMENT TYPE:

( v i ) ORIGINAL SOURCE:
        ( A ) ORGANISM: Synthetic DNA ( x i ) SEQUENCE DESCRIPTION: SEQ ID NO:20:

AGGTTATGCA TTAACTGAAT CTCGGACACA GACA 34

( 2 ) INFORMATION FOR SEQ ID NO:21:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: Synthetic DNA ( i i i ) HYPOTHETICAL: NO ( i v ) ANTI-SENSE: NO ( v ) FRAGMENT TYPE:

( v i ) ORIGINAL SOURCE:
        ( A ) ORGANISM: Synthetic DNA ( x i ) SEQUENCE DESCRIPTION: SEQ ID NO:21:

TAACCTTGGC AAACATTTGA ACTCCATGGA GCGTGTAGAA TGGCT 45

( 2 ) INFORMATION FOR SEQ ID NO:22:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: Synthetic DNA ( i i i ) HYPOTHETICAL: NO ( i v ) ANTI-SENSE: NO ( v ) FRAGMENT TYPE:

(v i) ORIGINAL SOURCE:
    (A) ORGANISM: Synthetic DNA (x i) SEQUENCE DESCRIPTION: SEQ ID NO:22:

TTACGCAGCC ATTCTACACG CTCCATGGAG TTCAAATGTT TGCCA    45

(2) INFORMATION FOR SEQ ID NO:23:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (i i) MOLECULE TYPE: Synthetic DNA (i i i) HYPOTHETICAL: NO (i v) ANTI-SENSE: NO (v) FRAGMENT TYPE:

(v i) ORIGINAL SOURCE:
      (A) ORGANISM: Synthetic DNA (x i) SEQUENCE DESCRIPTION: SEQ ID NO:23:

GCGTAAGAAG TTGCAGGATG TGCACAATTT    30

(2) INFORMATION FOR SEQ ID NO:24:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (i i) MOLECULE TYPE: Synthetic DNA (i i i) HYPOTHETICAL: NO (i v) ANTI-SENSE: YES (v) FRAGMENT TYPE:

(v i) ORIGINAL SOURCE:

(x i) SEQUENCE DESCRIPTION: SEQ ID NO:24:

GCAACAAAAT TGTGCACATC CTGCAACTTC    30

(2) INFORMATION FOR SEQ ID NO:25:

(i) SEQUENCE CHARACTERISTICS:
      (A) LENGTH: 46 base pairs
      (B) TYPE: nucleic acid
      (C) STRANDEDNESS: single
      (D) TOPOLOGY: linear (i i) MOLECULE TYPE: Synthetic DNA (i i i) HYPOTHETICAL: NO (i v) ANTI-SENSE: NO (v) FRAGMENT TYPE:

(v i) ORIGINAL SOURCE:
      (A) ORGANISM: Synthetic DNA (x i) SEQUENCE DESCRIPTION: SEQ ID NO:25:

TGTTGCCTTA GGTGCCCCAT TGGCTCCTCG TGATGCTGGT TCCCAA    46

(2) INFORMATION FOR SEQ ID NO:26:

( i ) SEQUENCE CHARACTERISTICS:
    ( A ) LENGTH: 46 base pairs
    ( B ) TYPE: nucleic acid
    ( C ) STRANDEDNESS: single
    ( D ) TOPOLOGY: linear ( i i ) MOLECULE TYPE: Synthetic DNA ( i i i ) HYPOTHETICAL: NO ( i v ) ANTI-SENSE: YES ( v ) FRAGMENT TYPE:

( v i ) ORIGINAL SOURCE:
    ( A ) ORGANISM: Synthetic DNA ( x i ) SEQUENCE DESCRIPTION: SEQ ID NO:26:

TGGTCTTTGG GAACCAGCAT CACGAGGAGC CAATGGGGCA CCTAAG     46

( 2 ) INFORMATION FOR SEQ ID NO:27:

( i ) SEQUENCE CHARACTERISTICS:
    ( A ) LENGTH: 41 base pairs
    ( B ) TYPE: nucleic acid
    ( C ) STRANDEDNESS: single
    ( D ) TOPOLOGY: linear ( i i ) MOLECULE TYPE: Synthetic DNA ( i i i ) HYPOTHETICAL: NO ( i v ) ANTI-SENSE: NO ( v ) FRAGMENT TYPE:

( v i ) ORIGINAL SOURCE:
    ( A ) ORGANISM: Synthetic DNA ( x i ) SEQUENCE DESCRIPTION: SEQ ID NO:27:

AGACCACGTA AAAAGGAAGA CAATGTCTTA GTTGAGAGCC A     41

( 2 ) INFORMATION FOR SEQ ID NO:28:

( i ) SEQUENCE CHARACTERISTICS:
    ( A ) LENGTH: 41 base pairs
    ( B ) TYPE: nucleic acid
    ( C ) STRANDEDNESS: single
    ( D ) TOPOLOGY: linear ( i i ) MOLECULE TYPE: Synthetic DNA ( i i i ) HYPOTHETICAL: NO ( i v ) ANTI-SENSE: YES ( v ) FRAGMENT TYPE:

( v i ) ORIGINAL SOURCE:
    ( A ) ORGANISM: Synthetic DNA ( x i ) SEQUENCE DESCRIPTION: SEQ ID NO:28:

TTTTCATGGC TCTCAACTAA GACATTGTCT TCCTTTTTAC G     41

( 2 ) INFORMATION FOR SEQ ID NO:29:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( i i ) MOLECULE TYPE: Synthetic DNA ( i i i ) HYPOTHETICAL: NO ( i v ) ANTI-SENSE: NO ( v ) FRAGMENT TYPE:

( v i ) ORIGINAL SOURCE:
    ( A ) ORGANISM: Synthetic DNA ( x i ) SEQUENCE DESCRIPTION: SEQ ID NO:29:

TGAAAAATCC CTAGGCGAGG CAGACAAGGC CGATGTGAAT GT  42

( 2 ) INFORMATION FOR SEQ ID NO:30:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: Synthetic DNA ( i i i ) HYPOTHETICAL: NO ( i v ) ANTI-SENSE: YES ( v ) FRAGMENT TYPE:

( v i ) ORIGINAL SOURCE:
        ( A ) ORGANISM: Synthetic DNA ( x i ) SEQUENCE DESCRIPTION: SEQ ID NO:30:

GTTAATACAT TCACATCGGC CTTGTCTGCC TCGCCTAGGG AT  42

( 2 ) INFORMATION FOR SEQ ID NO:31:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: Synthetic DNA ( i i i ) HYPOTHETICAL: NO ( i v ) ANTI-SENSE: NO ( v ) FRAGMENT TYPE:

( v i ) ORIGINAL SOURCE:
        ( A ) ORGANISM: Synthetic DNA ( x i ) SEQUENCE DESCRIPTION: SEQ ID NO:31:

ATTAACTAAA GCTAAATCCC AGTAATGAG  29

( 2 ) INFORMATION FOR SEQ ID NO:32:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: Synthetic DNA ( i i i ) HYPOTHETICAL: NO ( i v ) ANTI-SENSE: YES ( v ) FRAGMENT TYPE:

( v i ) ORIGINAL SOURCE:

(A) ORGANISM: Synthetic DNA (xi) SEQUENCE DESCRIPTION: SEQ ID NO:32:

GATCCTCATT ACTGGGATTT AGCTTTA                27

(2) INFORMATION FOR SEQ ID NO:33:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: Synthetic DNA (iii) HYPOTHETICAL: NO (iv) ANTI-SENSE: NO (v) FRAGMENT TYPE:

(vi) ORIGINAL SOURCE:
      (A) ORGANISM: Synthetic DNA (xi) SEQUENCE DESCRIPTION: SEQ ID NO:33:

CACAATTTTT GCGCCTTAGG TGC                23

(2) INFORMATION FOR SEQ ID NO:34:

(i) SEQUENCE CHARACTERISTICS:
      (A) LENGTH: 252 base pairs
      (B) TYPE: nucleic acid
      (C) STRANDEDNESS: double
      (D) TOPOLOGY: linear (ii) MOLECULE TYPE: Synthetic DNA (iii) HYPOTHETICAL: NO (iv) ANTI-SENSE: NO (v) FRAGMENT TYPE:

(vi) ORIGINAL SOURCE:
      (A) ORGANISM: Synthetic DNA (ix) FEATURE:
      (A) NAME/KEY: Coding Sequence
      (B) LOCATION: 1...252

(xi) SEQUENCE DESCRIPTION: SEQ ID NO:34:

```
TCT GTG TCC GAG ATT CAG TTA ATG CAT AAC CTT GGC AAA CAT TTG AAC      48
Ser Val Ser Glu Ile Gln Leu Met His Asn Leu Gly Lys His Leu Asn
 1               5                  10                  15

TCC ATG GAG CGT GTA GAA TGG CTG CGT AAG AAG TTG CAG GAT GTG CAC      96
Ser Met Glu Arg Val Glu Trp Leu Arg Lys Lys Leu Gln Asp Val His
            20                  25                  30

AAT TTT TGC GCC TTA GGT GCC CCA TTG GCT CCT CGT GAT GCT GGT TCC     144
Asn Phe Cys Ala Leu Gly Ala Pro Leu Ala Pro Arg Asp Ala Gly Ser
        35                  40                  45

CAA AGA CCA CGT AAA AAG GAA GAC AAT GTC TTA GTT GAG AGC CAT GAA     192
Gln Arg Pro Arg Lys Lys Glu Asp Asn Val Leu Val Glu Ser His Glu
    50                  55                  60

AAA TCC CTA GGC GAG GCA GAC AAG GCC GAT GTG AAT GTA TTA ACT AAA     240
Lys Ser Leu Gly Glu Ala Asp Lys Ala Asp Val Asn Val Leu Thr Lys
65                  70                  75                  80

GCT AAA TCC CAG                                                     252
Ala Lys Ser Gln
```

( 2 ) INFORMATION FOR SEQ ID NO:35:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:

( x i ) SEQUENCE DESCRIPTION: SEQ ID NO:35:

```
Pro  Tyr  Gly  Cys  Gly  Glu  Glu  Asn  Leu  Val  Tyr
 1              5                        10
```

( 2 ) INFORMATION FOR SEQ ID NO:36:

( i ) SEQUENCE CHARACTERISTICS:
        ( A ) LENGTH: 3 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:

( x i ) SEQUENCE DESCRIPTION: SEQ ID NO:36:

```
Pro  Tyr  Gly
 1
```

( 2 ) INFORMATION FOR SEQ ID NO:37:

( i ) SEQUENCE CHARACTERISTICS:
        ( A ) LENGTH: 432 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:37:

```
CCCGAGGATG  GCGGCAGCGG  CGCCTTCCCG  CCCGGCCACT  TCAAGGACCC  CAAGCGGCTG     60
TACTGCAAAA  ACGGGGCTT   CTTCCTGCGC  ATCCACCCCG  ACGGCCGAGT  TGACGGGGTC    120
CGGGAGAAGA  GCGACCCTCA  CATCAAGCTA  CAACTTCAAG  CAGAAGAGAG  AGGAGTTGTG    180
TCTATCAAAG  GAGTGAGCGC  TAATCGTTAC  CTGGCTATGA  AGGAAGATGG  AAGATTACTA    240
GCTTCTAAGT  CTGTTACGGA  TGAGTGTTTC  TTTTTTGAAC  GATTGGAATC  TAATAACTAC    300
AATACTTACC  GGTCAAGGAA  ATACACCAGT  TGGTATGTGG  CAGTGAAACG  AACTGGGCAG    360
TATAAACTTG  GATCCAAAAC  AGGACCTGGG  CAGAAAGCTA  TACTTTTTCT  TCCAATGTCT    420
GCTAAGAGCT  GC                                                            432
```

METHOD FOR PRODUCING A BIOLOGICALLY ACTIVE RECOMBINANT CYSTEINE-FREE PARATHYROID HORMONE (1-34)

This is a application of Ser. No. 08/350,709, file Dec. 7, 1994, abandoned, which is a continuation of Ser. No. 07/838,857, filed Feb. 18, 1992, abandoned.

BACKGROUND OF THE INVENTION

The present invention relates to a method for producing a cysteine-free peptide which comprises producing a fused protein or polypeptide and subsequently subjecting the thus obtained protein or polypeptide to cleavage of the peptide linkage at the cysteine residue of said fused protein or polypeptide.

In order to produce a peptide using gene recombination technology, the peptide expressed in the form of a fused protein is frequently employed since peptides are susceptible to be cleaved intracellularly. Known methods of cleaving the desired peptide from the fused protein include a chemical method using cyanogen bromide (Itakura et al., Science, 198,1056 (1977)) or an enzymatic method using enzyme Factor Xa (Nagai et al., Methods in Enzymology, 153, 46 (1987))

When cyanogen bromide is used, methionine-containing peptides cannot be produced; and when Factor Xa is used, the yield of the desired peptide is very low.

As the cleavage method, it is known that acylcysteine bond is cleaved by 2-nitro-5-thiocyanobenzoic acid (Seikagaku Jikken Koza (Biochemical Experiment), 1, Chemistry of Protein, pp. 247–250, 1976, Tokyo Kagaku Dohjin).

The present inventors investigated efficient cleavage of the desired peptide from the fused protein without using cyanogen bromide or factor Xa, and found that the desired cysteine-free peptide can be efficiently produced by producing a fused protein comprising a protein having cysteine at its N-terminal and a cysteine-free peptide ligated to the N-terminal using a gene manipulation technique or chemical synthesis and then subjecting the fused protein to a reaction for cleaving the peptide linkage.

SUMMARY OF THE INVENTION

The present invention relates to a method for producing a cysteine-free peptide by producing a fused protein or polypeptide and subsequently subjecting the fused product to cleavage at the cysteine residue of the fused protein or polypeptide.

BRIEF DESCRIPTION OF THE DRAWINGS

FIG. 2 (SEQ ID NO:11) shows the amino acid sequence of glucose-dependent insulinotropic polypeptide (GIP).

FIG. 3 (SEQ ID NO:12) shows the amino acid sequence of glucagon-like peptide (GLPI) (7-37).

FIG. 4 (SEQ ID NO:13) shows the amino acid sequence of parathyroid hormone (PTH) (1-34).

FIG. 8 (SEQ ID NO:14) shows the gene fragment used in Example 1.

FIGS. 11 (SEQ ID NO:16) and 12 show the entire amino acid sequence of the fused protein obtained in Example 1.

FIG. 16 (SEQ ID NO:17) shows the DNA sequence coding for Insulinotropin obtained in Example 6.

FIG. 18 (SEQ ID NO:18) shows the amino acid sequence of GLP-I(7-37)-hbFGF mutein CS23 obtained in Example 6.

FIG. 19 (line #1, SEQ ID NO:19; line #2, SEQ ID NO:20; line #3, SEQ ID NO:21; line #4, SEQ ID NO:22; line #5, SEQ ID NO:23; line #6, SEQ ID NO:24; line #7, SEQ ID NO:25; line #8, SEQ ID NO:26; line #9, SEQ ID NO:27; line #10, SEQ ID NO:28; line #11, SEQ ID NO:29; line #12, SEQ ID NO:30; line #13, SEQ ID NO:31; line #14, SEQ ID NO:32). shows the DNA fragments obtained in Example 7.

FIG. 20 shows the construction of a double stranded hPTH gene obtained in Example 7.

FIG. 21 shows the process for producing a double stranded DNA of hPTH obtained in Example 7.

FIG. 25 (SEQ ID NO:36) shows the DNA sequence coding for [Cys$^{35}$] human PTH and its deduced amino acid sequence, obtained in Example 7.

DESCRIPTION OF THE PREFERRED EMBODIMENTS

Figure 1:
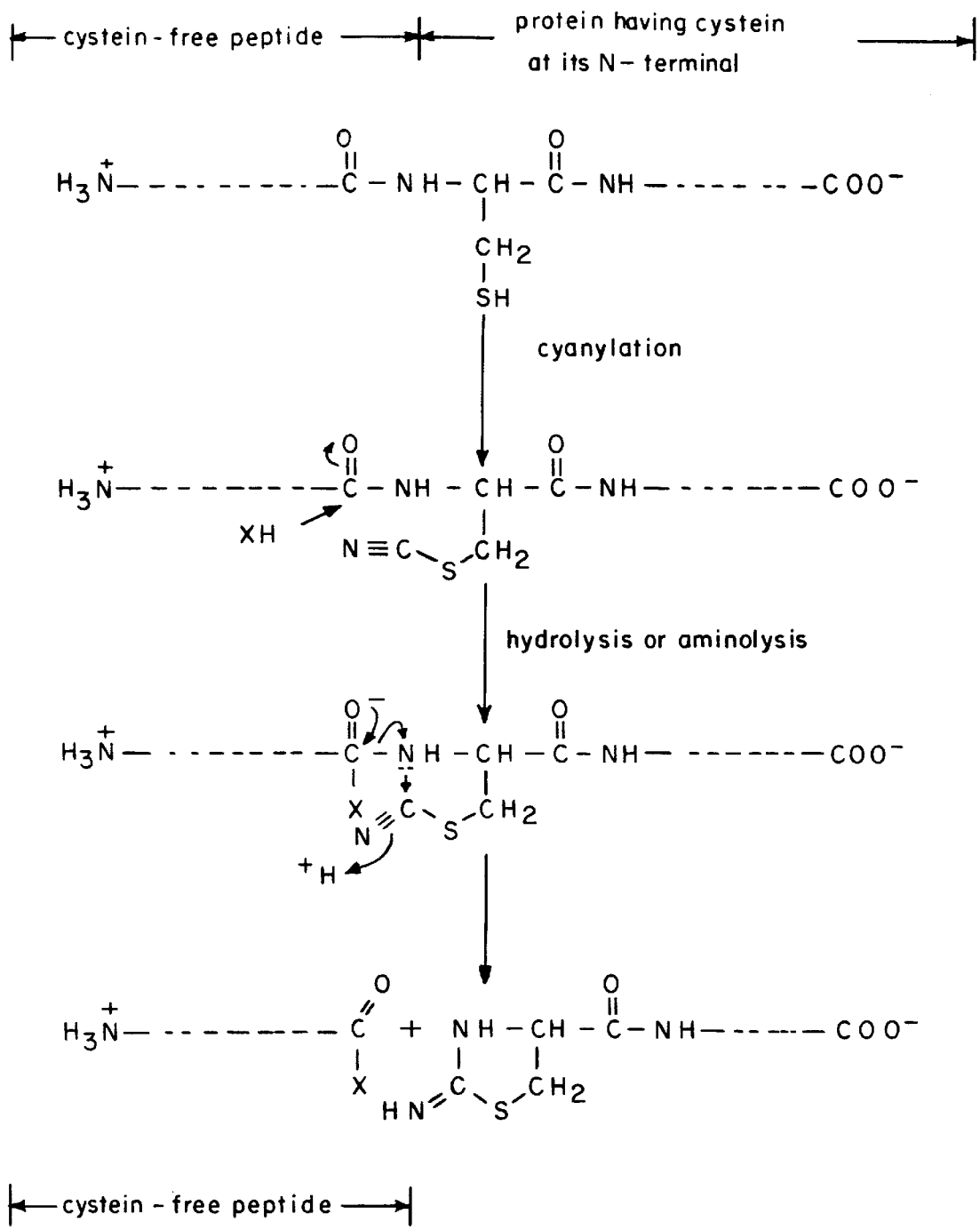
FIG. 1 shows the reaction scheme for the reaction processes of the present invention.

The present invention provides (1) a method for producing a cysteine-free peptide, which comprises cultivating a transformant having a vector carrying a gene coding for a fused protein comprising a protein having cysteine at its N-terminal and a cysteine-free peptide ligated to the N-terminal to express said fused protein, and subjecting the expressed protein to a reaction for cleaving the peptide linkage on the amino group side of the cysteine residue;

(2) a method for producing a cysteine-free peptide, which comprises constructing a gene which codes for a protein having a structure wherein a cysteine-free peptide is ligated to the N-terminal of a peptide having cysteine at its N-terminal, cultivating a transformant harboring a vector carrying said gene to express the protein, and subjecting the expressed protein to a reaction for cleaving the peptide linkage on the amino group side of the cysteine residue;

(3) a method for producing a cysteine-free peptide, which comprises chemically synthesizing a polypeptide which has a cysteine-free peptide ligated to the N-terminal of a peptide having cysteine at its N-terminal, and subjecting the thus obtained peptide to a reaction for cleaving the peptide linkage on the amino group side of the cysteine residue;

(4) a method of said method (1), (2) or (3), wherein an amino compound or a substituted amino compound is employed in the reaction for cleaving the peptide linkage to produce an amide or substituted amide derivative of the cysteine-free peptide; and (5) a peptide or salts thereof represented by the formula

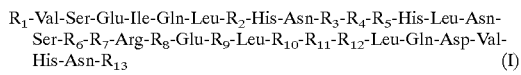

$R_1$-Val-Ser-Glu-Ile-Gln-Leu-$R_2$-His-Asn-$R_3$-$R_4$-$R_5$-His-Leu-Asn-Ser-$R_6$-$R_7$-Arg-$R_8$-Glu-$R_9$-Leu-$R_{10}$-$R_{11}$-$R_{12}$-Leu-Gln-Asp-Val-His-Asn-$R_{13}$ (I)

wherein $R_1$ represents Ser or Aib; $R_2$ represents Met or a naturally occurring hydrophobic amino acid; $R_3$ represents Leu, Ser, Lys or an aromatic amino acid; $R_4$ represents Gly or a D-α-amino acid; $R_5$ represents Lys or Leu; $R_6$ represents Met or a naturally occurring hydrophobic amino acid; $R_7$ represents Glu or a basic amino acid; $R_8$ represents Val or a basic amino acid; $R_9$ represents Trp or 2-(1,3-dithiolane-2-yl)Trp; $R_{10}$ represents Arg or His; $R_{11}$ represents Lys or His; $R_{12}$ represents Lys, Gln or Leu; and $R_{13}$ represents phenylalanine substituted amide; or salt thereof.

In the formula (I), Aib denotes aminoisobutyric acid. Naturally occuring hydrophobic amino acids, $R_2$ and $R_6$ mean hydrophobic ones among amino acids which consist of natural proteins originating from animal, plant or microorganisms, and including Leu, Ile, Val, Phe and Trp. Aromatic amino acids, $R_3$, include Phe, β-naphthyl Ala, Trp and Tyr. D-α-amino acids, $R_4$, may be any D-α-amino acid, and includes D-Leu, D-Ile, D-Nle, D-Val, D-Ser, D-Ser (But), D-Abu, D-Thr, D-Nva, D-Met, D-B-naphthyl-Ala, D-Trp, D-Tyr, D-Lys, D-Lys(Fmoc), D-Phe and D-Asn. Basic amino acids, $R_7$ and $R_8$, include Arg, Lys, Asn and His.

The substituents of the substituted amino compound or of the substituted amide include mono- or di-substituted amino. Specifically the substituent(s) include (i) $C_{1-20}$ alkyl, $C_{3-8}$ cycloalkyl, aryl or aryl-$C_{1-3}$ alkyl, which may have no substituent or one to three substituent(s) of the amino or hydroxyl group on their carbon atoms, (ii) amino or substituted amino, or (iii) hydroxyl or $C_{1-6}$ alkoxyl group.

Examples of said $C_{1-20}$ alkyl includes methyl, ethyl, propyl, isopropyl, butyl, sec-butyl, pentyl, isopentyl, neopentyl, 1-ethylpentyl, hexyl, isohexyl, heptyl, octyl, monanyl, decanyl undecanyl, dodecanyl, tetradecanyl, pentadecanyl, hexadecanyl, heptadecanyl, octadecanyl, monadecanyl, or eicosanyl.

Examples of said $C_{3-8}$ cycloalkyl include cyclopropyl, cyclobutyl, cyclopentyl, cyclohexyl, cycloheptyl, or cyclooctyl.

Examples of aryl include phenyl, naphthyl, anthryl, phenanthryl, or acenaphthylenyl.

Examples of aryl-$C_{1-3}$ alkyl include benzyl, phenethyl, 3-phenylpropyl (1-naphthyl)methyl, or (2-naphthyl)methyl.

Examples of $C_{1-6}$ alkoxyl group include methoxy, ethoxy, propoxy, butoxy, pentyloxy, or hexyloxy.

As the substituents of the substituted amino of (ii), an amino acid and peptide comprising two to 10 amino acids are exemplified.

Examples of the amino acid include L- or D-isomer of Ala Arg, Asp Asn Glu, Gln, Gly, His, Ile, Met, Leu, Phe, Pro, Ser, Thr, Trp, Tyr Val.

Examples of the peptides include H-D-Leu-Leu-Arg-Pro-NH-$C_2H_5$ (SEQ ID NO:1) or H-Val-Ala-Leu-D-Ala-Ala-Pro-Leu-Ala-Pro-Arg-OH (SEQ ID NO:2).

Examples of salts include salts with an inorganic base such as sodium and ammonium, with organic base such as triethylamine, ethylamine and methylamine, inorganic acid salts such as hydrochloride, sulfate, and nitrate, and orgainc acid salts such as formate, acetate, propionate, tartrate and citrate.

In the present invention, the desired peptide may be any peptide, as long as it is free of cysteine. The cysteine—free peptides include those having molecular weight of 100 to 12000, preferably 200 to 7000. Furthermore, as the cysteine-free peptides, there are also exemplified peptides having 2 to 100 amino acids, preferably 3 to 70 amino acids. Examples of such peptides include adrenocorticotropic hormone (ACTH), parathyroid hormone (PTH), enkephalins, endorphins, various opioid peptides, β-melanocyte stimulating hormone, glucose-dependent insulinotropic polypeptide (GIP), glucagon, glucagon-like peptides (GLP-I and II), motilin, thymopoietins, thymosins, ubiquitine, serum thymic factor, thymic humoral factor, various quinines, neurotensin, tuftsin and a fragment of these peptides.

A large number of peptides have an amide at their C-terminal and/or an -S-S- linkage in their molecule. These are also included in the desired peptide. Examples of such peptides include gastrin, calcitonin, calcitonin gene associated peptide, cholecystokinin-pancreozymin (CCK-PZ), eledoisin, epithelial growth factor (EGF), tumor growth factor (TGF-α), pancreastatin, insulin, insulin-like growth factors, luteinizing hormone-releasing hormone (LH-RH), mellitin, oxytocin, vasopressins, pancreatic polypeptide, trypsin inhibitor, relaxin, secretin, somatostatins, somatomedins, substance P, neurotensin, caerulein, thyrotropin-releasing hormone (TRH), vasoactive intestinal polypeptide (VIP), pituitary adenyl cyclase-activating polypeptides (PACAPs), gastrin-releasing peptide (GRP), endotherins, corticotropin-releasing factor (CRF), growth hormone-releasing factor (GRF), PTH-related protein, gallanin, peptide YY, neuropeptide Y, pancreastatin, atrial natriuretic peptides and also fragments of these peptides.

For the purpose of the present invention, any peptide having no cysteine at its N-terminal can be used, as long as it is given cysteine at its N-terminal before use. The peptides with cysteine at the N-terminal include those having molecular weight of 100 to 100000, preferably 300 to 50000. Furthermore, the peptides with cysteine at the N-terminal are those having 1 to 1000, preferably 3 to 500 amino acids.

Examples of such peptides include those having cysteine at the N-terminal of various growth factors such as interferons, interleukins and fibroblast growth factor (FGF), enzyme proteins such as (pro)urokinases, lymphotoxin, tumor necrosis factor (TNF) and β-galactosidase, storage proteins, streptavidin, protein A, protein G and tissue plasminogen activator (TPA), some of which may have cysteine at their N-terminal.

The gene used for the method of the present invention may be constructed by (1) chemically synthesizing the entire base sequence, or (2) placing the base sequence coding for cysteine on the N-terminal side of a base sequence coding for a protein and placing a base sequence coding for a cysteine-free peptide on the N-terminal side. Also, when it is desired to obtain a fragment of said peptide, the gene may be constructed by (3) substituting the amino acid residue immediately after the desired fragment with cysteine by, for example, site-directed mutagenesis or other technique.

In the case of (1) above, the desired gene can be prepared by ligation using T4 DNA ligase after synthesis of the entire sequence at once or in separate steps and if it is too long, by the phosphoamidide method, phosphoric acid triester method, diester method or hydrogen phosphonate method.

In the case of (2) above, the desired gene can be obtained as follows: The gene coding for the C-terminal protein is obtained by cleavage from chromosome with the appropriate restriction enzymes and subsequent ligation with a vector, or by obtaining a cDNA, which is then cleaved with restriction enzymes so that cysteine is present at its N-terminal or modified to have cysteine at its N-terminal by ligating a synthetic DNA to the 5'-terminal of the entire protein or partial gene thereof. The 5'-terminal is ligated to a gene coding for the desired protein which gene may be chemically synthesized or may be cloned, for example, from mammalian tissue.

Examples of said DNA include:

(i) (SEQ ID NO:3 and SEQ ID NO:4) TACGCGGAAGG-GACTTTCATCAGTGACTACAGTATTGC-CATGGACAAG ATTCACCAACAAGACTTTGT-GAACTGGCTGCTGGCCCAAAAGGGGAA GAAGAATGACTGGAAACACAACATCAC-CCAGTGC or TGTR (ii) (SEQ ID NO:5 and SEQ ID NO:6) TCTGTGAGT-GAAATACAGCTTATGCATAACCTGG-GAAAACATCTGAAC TCGATGGAGAGAGTA-GAATGGCTGCGTAAGAAGCTGCAGGATGTGCA CAATTTTTGC or TGTR (iii) (SEQ ID NO:7 and SEQ ID NO:8) CATGCT-GAAGGGACCTTTACCAGTGATGTAAGT-TCTTATTTGGAAGGC CAAGCTGCCAAGGAAT-TCATTGCTTGGCTGGTGAAAGGCCGAGGA TGC or TGTR The DNA (i) codes for glucose-dependent insulinotropic polypeptide (GIP); the DNA (ii) codes for PTH (1-34), the peptide corresponding to the 1-34 amino acid sequence of parathyroid hormone; and the DNA (iii) codes for glucagon-like peptide I (7-37) [GLP-I (7-37)] (insulinotropin).

In these formulas, R (a fragment of hbFGF) represents the base sequence comprising:

CCCGAGGATGGCGGCAGCGGCGCCTTC-CCGCCCGGCCACTTCAAGGAC CCCAAGCG-GCTGTACTGCAAAAACGGGGGCTTCTTC-CTGCGCATCCACCCCGACGGCCGA GTTGACGGGGTCCGGGAGAAGAGCGAC-CCTCACATCAAGCTACAACTTCAAGCA-G  A  A  G  A  G

AGAGGAGTTGTGTCTATCAAAGGAGTGAGCG-CTAATCGTTACCTGGCTATGAAGGAAGAT GGAAGATTACTAGCTTCTAAGTCTGT-TACGGATGAGTGTTTCTTTTTTGAAC-GATTGGAA TCTAATAACTACAATACTT-ACCGGTCAAGGAAATACACCAGTTGGTATGT-GGCACTGAAA CGAACTGGGCAGTATAAACT-TGGATCCAAAACAGGACCTGGGCA-GAAAGCTATACTTTTT CTTCCAATGTCT-GCTAAGAGCTGC (SEQ ID NO:37)

When the desired peptide has an amide at its C-terminal, any of the sequences GGT, GGC, GGA or GGG, which all code for amide-convertible glycine, is inserted at the 5' side of TGT or TGC.

A DNA (plasmid) which has ATG at its 5'-terminal a region coding for the fused protein downstream thereof and a translation termination codon further downstream can be produced by chemical synthesis or by processing known cDNA of said protein produced by gene engineering or by using the chromosome-derived DNA of said protein.

In addition to the conventional DNA technology, site-directed mutagenesis may also be employed to produce a gene coding for a protein having a structure wherein a cysteine-free peptide is ligated to the N-terminal of a peptide having cysteine at its N-terminal. This technique is well-known, and it is described in R. F. Lathe J. P. Lecocq and R. Everett, Genetic Engineering 4 edited by Robert Williamson, Academic Press, pp 31 to 50 (1983). Mutagenesis directed to oligonucleotide is described in Genetic Engineering: Principles and Methods, Smith, M. and Gillam, S., Plenum Press, Vol. 3, pp. 1 to 32 (1981).

The production of the structural gene which encodes the above-described protein is, for example, carried out by:

(a) hybridizing with a mutagenic oligonucleotide primer a single-stranded DNA comprising 1 strand of the structural gene, (b) elongating the primer using DNA polymerase to form a mutational heteroduplex, and (c) replicating this mutational heteroduplex.

The size of oligonucleotide primer depends upon conditions essential to stable hybridization of the primer to the gene region to which mutation is to be introduced, and upon limitations in currently available methods of oligonucleotide synthesis. The factors to be considered in designing the oligonucleotide intended for use in mutagenesis directed by the oligonucleotide (e.g., the overall size of the nucleotide and the size of the mismatching portion at the mutation site) are described by Smith, M. and Gillam, S. in the above-mentioned literature. In general, the overall length of the oligonucleotide is adjusted to such length that stable and unique hybridization at the mutation site is optimized and the extensions between the mutation site and the 5'- and 3'-terminals are provided with sufficient sizes to prevent mutation editing due to the exonuclease activity of DNA polymerase.

The oligonucleotides used for mutagenesis in accordance with the present invention normally contain some 12 to 24 bases, preferably 14 to 20 bases, and more preferably 14 to 18 bases. These normally contain at least 3 bases successively to the codon to be changed toward 3'-terminal.

The peptide represented by the formula (I) (SEQ ID NO:9) shown above is a derivative of human PTH. The amino acid sequence of the original human PTH is shown below:

Ser—Val—Ser—Glu—Ile—Gln—Leu—Met—His—Asn—Leu—Gly—Lys—His—Leu—Asn—Ser—Met—
1                          5                          10                         15

Glu—Arg—Val—Glu—Trp—Leu—Arg—Lys—Lys—Leu—Gln—Asp—Val—His—Asn—Phe—Val—Ala—
         20                          25                         30

Leu—Gly—Ala—Pro—Leu—Ala—Pro—Arg—Asp—Ala—Gly—Ser—Gln—Arg—Pro—Arg—Lys—Lys—
              40                          45                         50

Glu—Asp—Asn—Val—Leu—Val—Glu—Ser—His—Glu—Lys—Ser—Leu—Gly—Glu—Ala—Asp—Lys—
55                                       65                         70

Ala—Asp—Val—Asn—Val—Leu—Thr—Lys—Ala—Lys—Ser—Gln   (SEQ ID NO: 9)
         75                          80

For example, from a gene coding for human PTH (1-84), a gene coding for the peptide represented by the formula (I) can be produced using said site-directed mutagenesis method. For example, when a mutein wherein valine in the human PTH is substituted with cysteine is to be obtained, a gene coding for the mutein is produced by the site-directed mutagenesis method using synthesized nucleotide primer.

For example, when valine at the 35-position of human PTH is replaced with cysteine, the preferred primer includes 5'-CACAATTTTTGCGCCTTAGG-3' (oligonucleotide primer A) (SEQ ID NO:10).

The primer is hybridized to a single-stranded phage such as M13 [Yanisch-Perror, C., Vieira, J. Messing, Gene, 33, 103–119 (1985); Messing J., Methods in Enzymology, 101, 20–78 (1983)], cloned from the single-stranded DNA of the human PTH gene, fd [R. Herrman et al., Molecular and General Genetics, 177,231 (1980)] or Φx174 [M. Smith and S. Gillam, Genetic Engineering, Plenum Press, Vol. 3, pp. 1–32 (1981)] or a phage-plasmid chimeric vector such as pUC118 or pUC119 [J. Vieira and J. Messing, Methods in Enzymology, 153, 3–11 (1987)]. The phage is recognized as capable of carrying both the sense chain and antisense chain of the gene. When the phage carries an antisense chain, the primer may, due to codon degeneration, be unidentical with the sense chain region containing the codon to be mutated, in addition to the disagreement with this codon, thus determining a triplet encoding another amino acid. Similarly, when the phage carries a sense chain, the primer may not be complementary to the sense chain region containing the codon to be mutated, except for appropriate disagreements in the triplet forming a pair with the codon to be deleted. Conditions used for this hybridization are described by M. Smith and S. Gillam in the above-mentioned publication. Temperature normally ranges from about 0° C. to 70° C., preferably from 10° C. to 50° C. After hybridization, the primer is elongated on the phage DNA by reaction with *Escherichia coli* DNA polymerase I, T4 DNA polymerase, reverse transcriptase or other appropriate DNA polymerase. The resulting double-stranded DNA (dsDNA) is converted to cyclic dsDNA by treatment with a DNA ligase such as T4 DNA ligase. DNA molecules having a single-stranded region can be disrupted by S1 endonuclease treatment.

The resulting mutagenic hetero dimer is used to transform infectable host organisms or cells. In the replication of hetero dimers in a host, offspring emerge from both chains. Replication is followed by isolation of the mutant gene from the mutant chain offspring, which is inserted into an appropriate vector. This vector is then used to transform appropriate host organisms or cells. Next, the phage DNA carrying the mutated gene is isolated and inserted into a plasmid.

Examples of the plasmid used as a vector to produce a plasmid carrying DNA having a region coded for said fused protein include ColEI-derived plasmids such as pBR322 [Gene, 2, 95 (1977)], pBR313 [Gene, 2, 75 (1977)], pBR324, pBR325 [Gene, 4, 124 (1978)], pBR327, pBR328 [Gene, 9,287 (1980)], pBR329 [Gene, 17, 79 (1982)], pKY2289 [Gene, 3,1 (1978)], pKY2700 [Seikagaku, 52, 770 (1980)], pACYC177, pACYC184 [Journal of Bacteriology, 134, 1141 (1978)], pRK248, pRK646, pDF [Methods in Enzymology, 68, 268 (1979)], pUC12 [Gene, 19, 259 (1982)], pUC13 [Gene, 19, 259 (1982)], pUC18, pUC19 [Janisch-Perror et al., Gene, 33, 103 (1985)], pUB110, pTP5, pC194, pSH19 and pSH15. Also useful are vectors using λ phage or other bacteriophage such as λgt·λC [Proc. Nat. Acad. Sci., USA, 71, 4579 (1974)], λgt·λB [Proc. Nat. Acad. Sci., USA, 72, 3461 (1975)], λDam [Gene, 1, 255 (1977)], Charon vector [Science, 196, 161 (1977); Journal of Virology, 29, 555 (1979)] and mp vectors using a filamentous phage such as mp18 and mp19 [Janisch-Perror et al., Gene, 33, 103 (1985)].

The DNA preferably has a promoter upstream of ATG. Any promoter can be used as long as it is suitable for the host in producing a transformant.

Examples of such promoters include the trp promoter, lac promoter, rec A promoter, λPL promoter, lpp promoter and T-7 promoter for *Escherichia coli*, SPO1 promoter, SPO2 promoter and penP promoter for *Bacillus subtilis*, PHO5 promoter, PGK promoter, GAP promoter and ADH promoter for yeast (such as *Saccharomyces cerevisiae*) and the SV40-derived promoter for animal cells. The SD (Shine and Dalgarno) sequence may be inserted downstream of the promoter as necessary.

When using the T-7 promoter system, the promoter may be any of the 17 promoters found on the T7 DNA [J. L. Oakley et al., Proc. Natl. Acad. Sci., USA, 74, 4266–4270 (1977); M. D. Rosa, Cell, 16, 815–825 (1979); N. Panayotatos et al., Nature, 280, 35 (1979); J. J. Dunn et al., J. Mol. Biol., 166, 477–535 (1983)]. The Φ10 promoter [A. H. Rosenberg et al., Gene, 56, 125–135 (1987)] is most preferable.

Any transcription terminator can be used, as long as it functions in *Escherichia coli* systems, but the TΦ terminator [F. W. Studier et al., J. Mol. Biol., 189, 113–130 (1986)] is preferred.

The T7 RNA polymerase gene is exemplified by the T7 gene [F. W. Studier et al., J. Mol. Biol., 189, 113–130 (1986)].

The vector is constructed by inserting the T7 promoter and T7 terminator into the vector described above. Examples of such vectors include pET-1, pET-2, pET-3, pET-4 and pET-5 [A. H. Rosenberg, Gene, 56, 125–135 (1987)], with preference given to pET-3c [A. H. Rosenberg].

The transformant for the present invention can be produced by transforming a host with an expression plasmid obtained as described above using a known method [e.g., the method of Cohen S. N. et al., Proceedings of National Academy of Science, USA, 69, 2110 (1972)].

Examples of the host to be transformed include bacteria belonging to the genus Escherichia, bacteria belonging to the genus Bacillus, yeasts, and animal cells.

Examples of the bacteria belonging to the genus Escherichia include *Escherichia coli*, specifically *Escherichia coli* K12DH1 [Proceedings of National Academy of Science, USA, 60, 160 (1968)], JM-103 [Nucleic Acids Research, 9, 309 (1981)], JA221 [Journal of Molecular Biology, 120, 517 (1978)], HB101 [Journal of Molecular Biology, 41, 459 (1969)], C600 [Genetics, 39, 440 (1954)], N4830 [Cell, 25, 713 (1981)], K-12MM294 [Proceedings of National Academy of Science, USA, 73, 4174 (1976)] and BL21.

Examples of the bacteria belonging to the genus Bacillus include *Bacillus subtilis*, specifically *Bacillus subtilis* MI114 [Gene, 24, 255 (1983)] and 207–21 [Journal of Biochemistry, 95, 87 (1984)].

Examples of the yeasts include *Saccharomyces cerevisiae*, specifically *Saccharomyces cerevisiae* AH22 [Proceedings of National Academy of Science, USA, 75, 1929 (1978)], XSB52-23C [Proceedings of National Academy of Science, USA, 77, 2173 (1980)], BH-641A (ATCC 28339), 20B-12 [Genetics, 85, 23 (1976)] and GM3C-2 [Proceedings of National Academy of Science, USA, 78, 2258 (1981)].

Examples of the animal cells include simian cells COS-7 [Cell, 23, 175 (1981)], Vero [Japanese Journal of Clinical Medicine, 21, 1209 (1963)], Chinese hamster cells CHO [Journal of Experimental Medicine, 108,945 (1985)], mouse L cells [Journal of National Cancer Institute, 4, 165 (1943)], human FL cells [Proceedings of the Society for Experimental Biology and Medicine, 94, 532 (1957)] and hamster C cells.

When using a T-7 promoter system, any host can be used to obtain the desired transformant, as long as it is an *Escherichia coli* strain capable of incorporating the T7 RNA polymerase gene (T7 gene 1) [F. W. Studier et al., J. Mol. Biol., 189, 113–130 (1986)]. Examples of such strains are MM294, DH-1, C600, JM109, BL21 or an *Escherichia coli* strain with another plasmid with the T7 RNA polymerase gene (T7 gene 1). It is preferable to use the MM294 strain or BL21 strain resulting from lysogenization of a $\lambda$ phage incorporating the T7 gene 1. In this case, the lac promoter is used as promoter for the T7 gene 1, which induces expression in the presence of isopropyl-1-thio-$\beta$-D-galactopyranoside (IPTG).

The transformation of the host of the genus Bacillus, can be carried out using a known method such as that disclosed in Molecular & General Genetics, 168, 111 (1979).

The transformation of the host of yeast, can be carried out using a known method such as that disclosed in Proc. Natl. Acad. Sci. USA, 75, 1929 (1978).

The transformation of the host, an animal cell, can be carried out using a known method such as that disclosed in Virology, 52, 456 (1973).

The fused protein can be produced by cultivating the transformant described above, to produce and accumulate the fused protein in a cultured medium and then harvesting it.

It is desirable that the pH of medium be about 6 to 8.

An example of appropriate medium for the cultivation of bacteria of the genus Escherichia is the M9 medium containing glucose and casamino acids [Miller, Journal of Experiments in Molecular Genetics, 431–433, Cold Spring Harbor Laboratory, New York (1972)]. A chemical substance such as 3 $\beta$-indolylacrylic acid may be added thereto, when it is necessary to increase promoter efficiency.

When the host is a bacterium of the genus Escherichia, cultivation is normally carried out at about 15° to 43° C. for about 3 to 24 hours, and, where necessary, aeration and/or agitation may also be performed.

When the host is a bacterium of the genus Bacillus, cultivation is normally carried out at about 30° to 40° C. for about 6 to 24 hours, and, where necessary, aeration and/or agitation may also be performed.

As a medium for the cultivation of transformants whose host is a yeast, Burkholder's minimum medium may be used [Bostian, K. L. et al., Proc. Natl. Acad. Sci. USA, 77, 4505 (1980)]. It is preferable that the pH of the medium be adjusted to about 5 to 8. Cultivation is normally carried out at about 20° to 35° C. for about 24 to 72 hours, and, where necessary, aeration and/or agitation may also be performed.

Media for the cultivation of transformants whose host is an animal cell include MEM media containing about 0.2 to 20% preferably about 5 to 20% fetal bovine serum [Science, 122, 501 (1952)], DMEM medium [Virology, 8, 396 (1959)], RPMI1640 medium [Journal of the American Medical Association, 199, 519 (1967)] and 199 medium [Proceeding of the Society for the Biological Medicine, 73, 1 (1950)]. It is preferable that pH be about 6 to 8. Cultivation is normally carried out at about 30° to 40° C. for about 15 to 60 hours, and, where necessary, aeration and/or agitation may be performed.

When using a recombinant vector having both a $\lambda$cIts repressor and an expression vector carrying a $\lambda$PL-promoter, it is preferable to carry out cultivation of the transformant at a temperature between about 15° and 36° C. preferably about 30° and 36° C. and inactivate the $\lambda$cIts repressor at a temperature between about 37° and 42° C. Also, to increase recA promoter efficiency, i.e., to lower the recA gene expression suppressive function, a drug such as mitomycin C or nalidixic acid may be added or alternatively ultraviolet irradiation may be employed.

When using a T-7 promoter system, IPTG is added to express the T7 gene (RNA polymerase gene) ligated downstream from the lac promoter by specifically activating the T7 promoter via the resulting T7 phage RNA polymerase 1.

After cultivation, cells are collected by a known method and suspended in a buffer, after which they are disrupted by protein denaturant treatment, ultrasonic treatment, enzymatic treatment using lysozyme, glass bead treatment, French press treatment, freeze-thawing or other process, followed by centrifugation or other known methods, to yield a supernatant.

From the supernatant thus obtained, the fused protein can be isolated in accordance with known methods of protein purification. For example, gel filtration, ion exchange chromatography, adsorption chromatography, high performance liquid chromatography, affinity chromatography, hydrophobic chromatography and electrophoresis can be used in combination, as appropriate. The fused protein may be subjected to the subsequent reaction process without purification or in a partially purified state.

In the chemical synthesis of the polypeptide formed by the ligation of a cysteine-free peptide to the N-terminal of a peptide having cysteine at its N-terminal, in accordance with the present invention, the peptide synthesis can be carried out by the use of an automatic peptide synthesizer. The method of R. B. Merrifield *Advances in Enzymology* 32, 221–296 (1969) applies correspondingly. In this method, the amino acid of the carboxyl terminus is covalently bound to a resin carrier, and elimination of a protective group of an $\alpha$-amino group and condensation of a protected amino acid are repeated in turn to extend a peptide chain to the amino terminus, thereby obtaining a protected peptide resin having a desired amino acid sequence. The condensation of each amino acid and the elimination of the protective groups of the $\alpha$-amino groups are performed under approximately similar conditions, and purification of intermediates is not conducted. In synthesizing peptides, therefore, a high level of skill is generally not required. Moreover, the peptides are rapidly synthesized by this method, so that this method is very convenient in synthesizing various peptides. The protected peptide resin thus obtained is reacted with, for example, anhydrous hydrogen fluoride, trifluoromethanesulfonic acid or trifluoroacetic acid in the presence of various additives, whereby elimination of the peptide from the resin and removal of all protective groups can be achieved in one step.

The resulting crude peptide can be purified by known methods of purifying peptides or proteins. Examples of such methods include column chromatography such as gel filtration, ion exchange chromatography using a cation exchange resin or an anion exchange resin, hydrophobic chromatography and partition adsorption chromatography, as well as high performance liquid chromatography.

The protein or polypeptide thus obtained is then subjected to a reaction for cleaving the peptide linkage on the amino group side of the cysteine residue.

This reaction can be performed, for example, by cyanylation followed by hydrolysis or aminolysis.

The cyanylation is carried out by reacting an S-cyanylation reagent on the starting compound.

Examples of S-cyanylation reagents include 2-nitro-5-thiocyanobenzoic acid (NTCB), 1-cyano-4-dimethylaminopyridium salt (DMAP-CN) and $CN^{31}$ ion. The amount of S-cyanylation reagent is about 2 to 50 times, preferably about 5 to 10 times the total amount of all thiol groups.

Reaction temperature can be set at any level in the range from about 0° to 80° C., preferably between about 0° and 50° C. Any buffer can be used as a solvent, as long as it does not react with the cyanylating reagent. Examples of such buffers include Tris-HCl buffer, Tris-acetate buffer, phosphate buffer and borate buffer. An organic solvent may be present, as long as it does not react with the cyanylating reagent.

The reaction is normally carried out at a pH of between 1 and 12. Particularly when using NTCB, a pH range of from 7 to 10 is preferred. When using DMAP-CN, a pH range of from 2 to 7 is preferred, to avoid S-S exchange reaction. The reaction mixture may contain a denaturant such as guanidine hydrochloride.

Reaction for cleaving by hydrolysis or aminolysis can be achieved for instance by alkali treatment.

The alkali treatment is carried out by adjusting the aqueous solution containing the starting compound to a pH of 6 to 14, preferably 7 to 14.

The pH can be adjusted by adding an appropriate amount of a solution of sodium hydroxide, ammonia, a substituted amino compound, trizma base (tris[hydroxymethyl]-aminomethane), secondary sodium phosphate, potassium hydroxide or barium hydroxide, to the aqueous solution containing the starting compound. Examples of said substituted amino compounds are listed above.

The concentration of said solution are, for sodium hydroxide about 0.01–20N, preferably about 0.1N–1N; for ammonia or substituted amino compound about 0.01–15N, preferably about 0.1N–3N; for trizma base about 1 mM–1M, preferably about 20 mM–200 mM; for secondary sodium phosphate about 1 mM–1M, preferably about 10 mM–100 mM; for potassium hydroxide about 0.01–14N, preferably about 0.1–2N; for barium hydroxide about 0.01–0.2M, preferably about 0.1M–0.2M.

Reaction temperature can be set at between about 0° to 80° C., preferably between about 0° and 50° C. Reaction times are preferably as follows: for cyanylation time about 10–60 minutes, preferably about 15–30 minutes; for hydrolysis time about 5 minutes to 100 hours, preferably about 10 minutes to 15 hours; for aminolysis time about 5 minutes-24 hours, preferably about 10–180 minutes.

It is believed that the reaction shown in FIG. 1 takes place upon the occurance of cyanylation, and hydrolysis or aminolysis described above. In FIG. 1, X denotes OH or R—NH—(R—NH-means amino or substituted amino group).

In adjusting the pH, the use of amino compounds or a derivative of amine makes it possible to produce the corresponding amide compound or substituted amide compound.

The desired peptide obtained through cleavage can be purified in accordance with a known method of peptide purification. For example, gel filtration, ion exchange chromatography, high performance liquid chromatography, affinity chromatography, hydrophobic chromatography, thin-layer chromatography and electrophoresis can be used in combination, as appropriate. Thus obtained peptide may have methionine corresponding to the translation starting codon ATG at its N-terminus.

The desired peptide thus obtained can be powdered by lyophilization, as necessary. In lyophilization, a stabilizer such as sorbitol, mannitol, dextrose, maltose, trehalose or glycerol may be added.

This method makes it possible to produce peptides with various bioactivities. For example, the GIP (glucose-dependent insulinotropic polypeptide), the amino acid sequence of which is shown in FIG. 2, and GLPI (7-37), the amino acid sequence of which is shown in FIG. 3, produced by the method of the present invention can be used very safely as therapeutic drugs for diabetes mellitus because they promote insulin secretion in the presence of a physiological concentration of glucose. Also, the parathyroid hormone (PTH) and its active fragment PTH (1-34), its amino acid sequence is shown in FIG. 4, comprising 34 peptides from its N-terminal, prepared by the method of the present invention is useful as a therapeutic drug for osteoporosis because it enhances bone metabolism.

The peptide produced by the method of the present invention can be mixed with sterile water, human serum albumin (HSA), physiological saline and other known physiologically acceptable carriers, and can be administered non-perorally or locally. It can be administered non-perorally by intravenous, intramuscular or other means at a daily dose of about 2,000 to 2,000,000 U/kg, preferably about 80,000 to 800,000 U/kg.

Preparations containing the peptide produced by the method of the present invention may contain salts, diluents, adjuvants and other carriers, buffers, binders, surfactants, preservatives and other physiologically acceptable active ingredients. Non-peroral preparations are supplied as sterile water solutions, ampules containing a suspension in a physiologically acceptable solvent or ampules containing a sterile powder normally obtained by lyophilizing a peptide solution which can be freshly prepared in dilution with a physiologically acceptable diluent for each use.

The method of the present invention is advantageous in producing a peptide which can be used for pharmaceutical and other uses on an industrial scale because it permits the production of the desired peptide which does not decompose.

The human PTH(1-34) derivative peptides represented by general formula (I) of the present invention can be used as therapeutic agents for osteoporosis, hypoparathyroidism and hypertension. The means of thereof administration include injections, nasotracheal absorption agents, perrectum absorption agents, transvaginal absorption agents, percutaneous absorption agents and eye drops. In some cases, they can be orally administered.

When the peptides are used as such therapeutic agents, effective amounts thereof are used to treat mammals, especially humans. Although they are generally used within the range of 1 ng to 100 $\mu$g/kg of weight, specific amounts may be determined by those skilled in the art.

When the peptides are used as therapeutic agents, they must be carefully purified so as to contain no bacteria and no pyrogens.

The peptides, when used as therapeutic agents for osteoporosis and the like, can be administered parenterally in the form of the above-described injections, nasotracheal absorption agents, perrectum absorption agents, transvaginal absorption agents, percutaneous absorption agents or eye drops, solely or in combination with pharmaceutically acceptable carriers, excipients or diluents. In the case of the injections, it is appropriate that the peptides are given to adults in a dose of 50 ng/kg to 5 mg/kg for 1 to 3 dasys, and preferably in a dose of 1 to 50 $\mu$g/kg for 1 to 3 days. In the case of injections, it is appropriate that the concentration of the therapeutic agent is 10 to 100 $\mu$g/ml.

Abbreviations for amino acids, peptides, protective groups, active groups and other materials used in the present specification and attached drawings are based on abbreviations specified by the IUPAC-IUB Commission on Biochemical Nomenclature or abbreviations in common use in relevant fields. Some examples are given in Table 1 below. When there is a possibility of the presence of an optical isomer in amino acid, the L-configuration is used, unless otherwise stated.

TABLE 1

| DNA: | Deoxyribonucleic acid |
|---|---|
| A: | Adenine |
| T: | Thymine |
| G: | Guanine |
| C: | Cytosine |
| RNA: | Ribonucleic acid |
| EDTA: | Ethylenediaminetetraacetic acid |
| Gly: | Glycine |
| Ala: | Alanine |
| Val: | Valine |
| Leu: | Leucine |
| Ile: | Isoleucine |
| Ser: | Serine |
| Thr: | Threonine |
| Met: | Methionine |
| Glu: | Glutamic acid |
| Asp: | Aspartic acid |
| Lys: | Lysine |
| Arg: | Arginine |
| His: | Histidine |
| Phe: | Phenylalanine |
| Tyr: | Tyrosine |
| Trp: | Tryptophan |
| Pro: | Proline |
| Asn: | Asparagine |
| Gln: | Glutamine |
| Aib: | Aminoisobutyric acid |
| Nle: | Norleucine |
| β-Ala: | P-Alanine |
| hPTH: | Human PTH |
| Fmoc: | 9-Fluorenylmethoxycarbonyl |
| Nva: | Norvaline |
| Abu: | α-Aminobutyric acid |

The transformant *Escherichia coli* MM294 (DE3)/ pTB960-3 obtained in Example 5 (2) below has been deposited under accession number IFO 15241 at the Institute for Fermentation, Osaka (IFO), Japan since Oct. 16, 1991, and has been deposited under accession number FERM BP-3615 under the Budapest Treaty at the Fermentation Research Institute, Agency of Industrial Science and Technology, Ministry of International Trade and Industry (FRI), Japan since Oct. 19, 1991.

The transformant *Escherichia coli* MM294 (DE3)/ pTB960-7 obtained in Example 6 (1) below has been deposited at the IFO under the accession number IFO 15254 since Dec. 17, 1991, and has been deposited at the FRI under the Budapest Treaty under the accession number FERM BP-3690 since Dec. 24, 1991.

The present invention is described in more detail by means of the following non-limiting reference and working examples.

REFERENCE EXAMPLE 1

Preparation of recombinant with tetracycline resistance marker which produces rhbFGF mutein CS23

Figure 5:
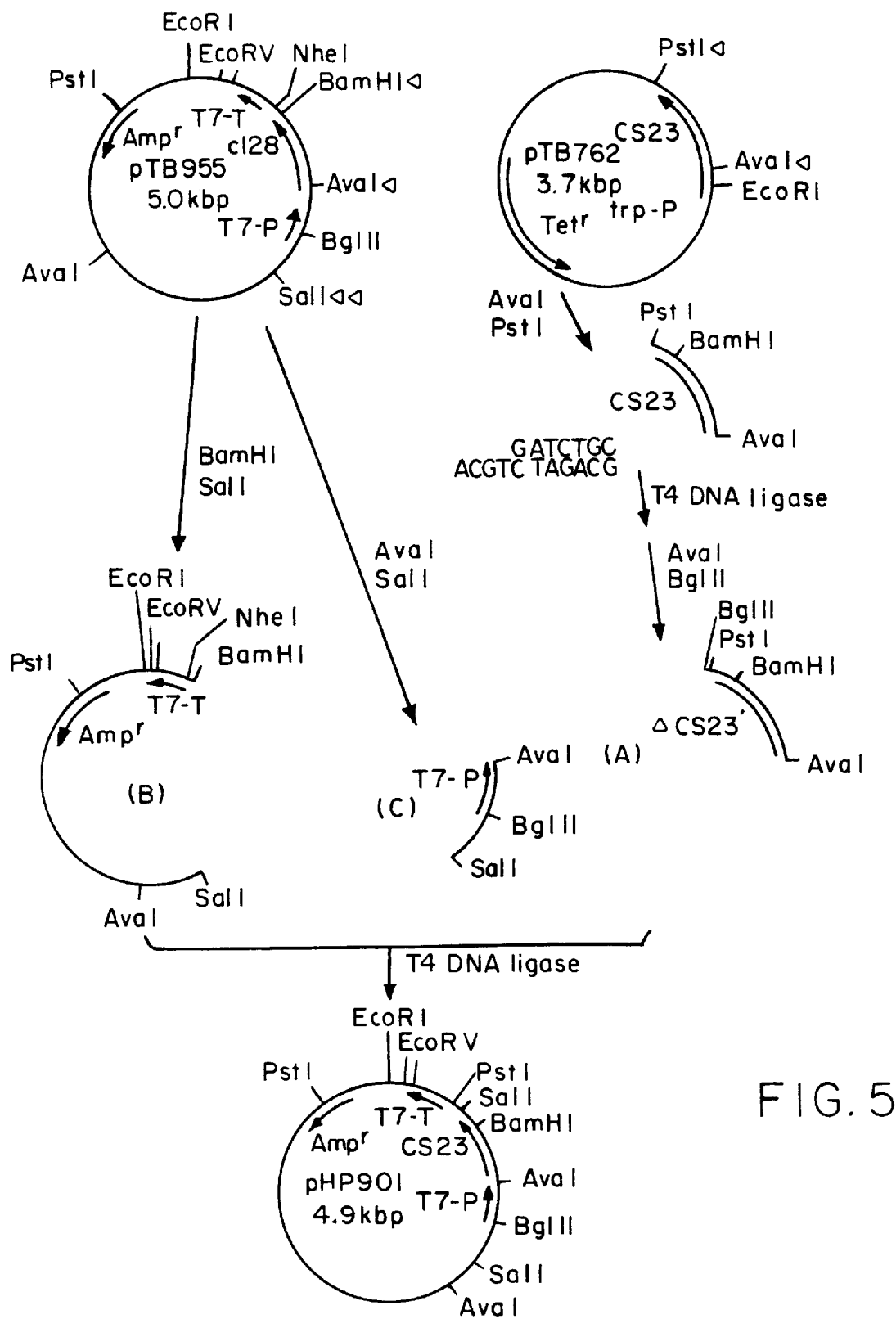
FIG. 5 shows the construction scheme for the plasmid pHP901 obtained in Reference Example 1.
Figure 6:
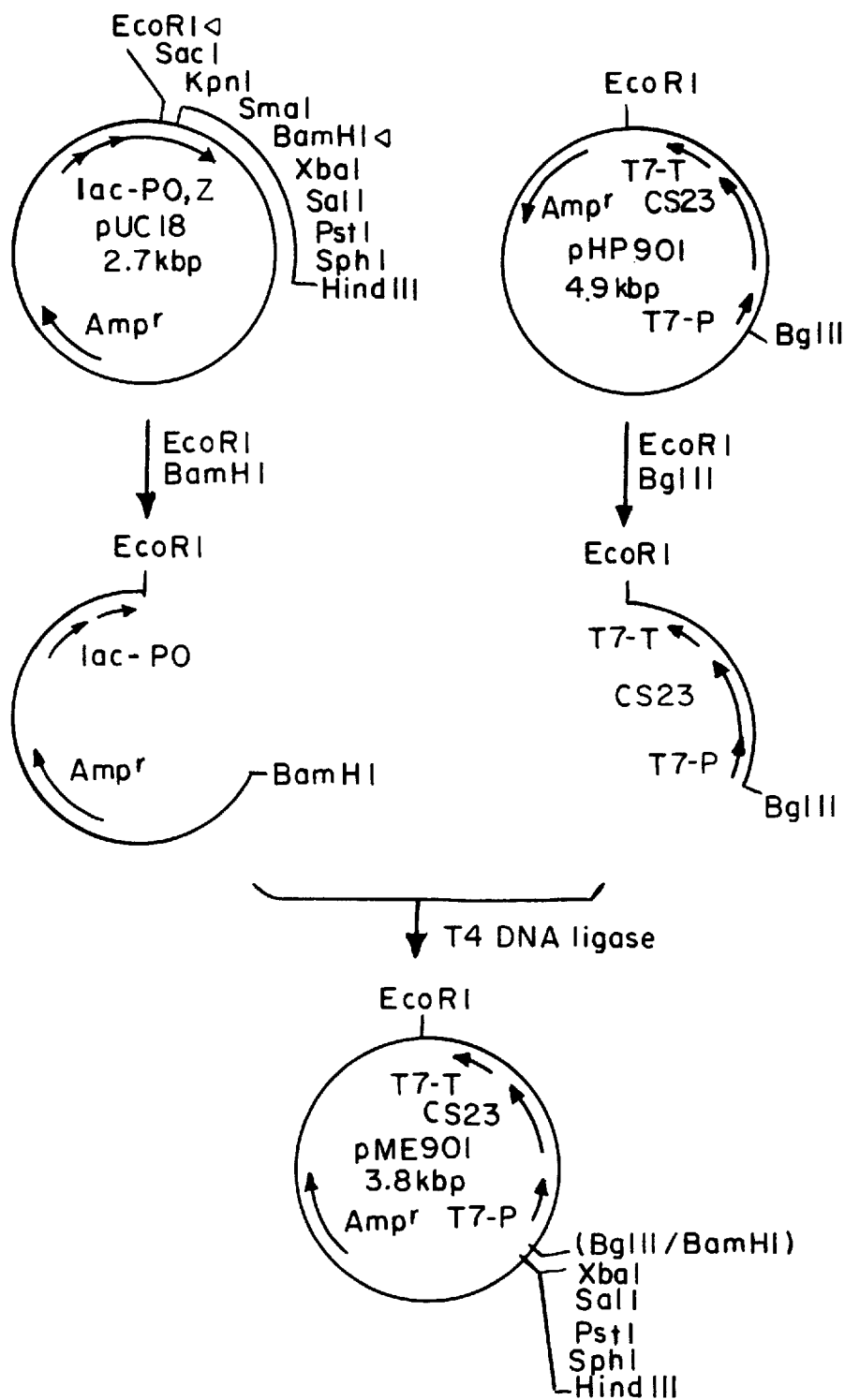
FIG. 6 shows the construction scheme for the plasmid pME901 obtained in Reference Example 1.
Figure 7:
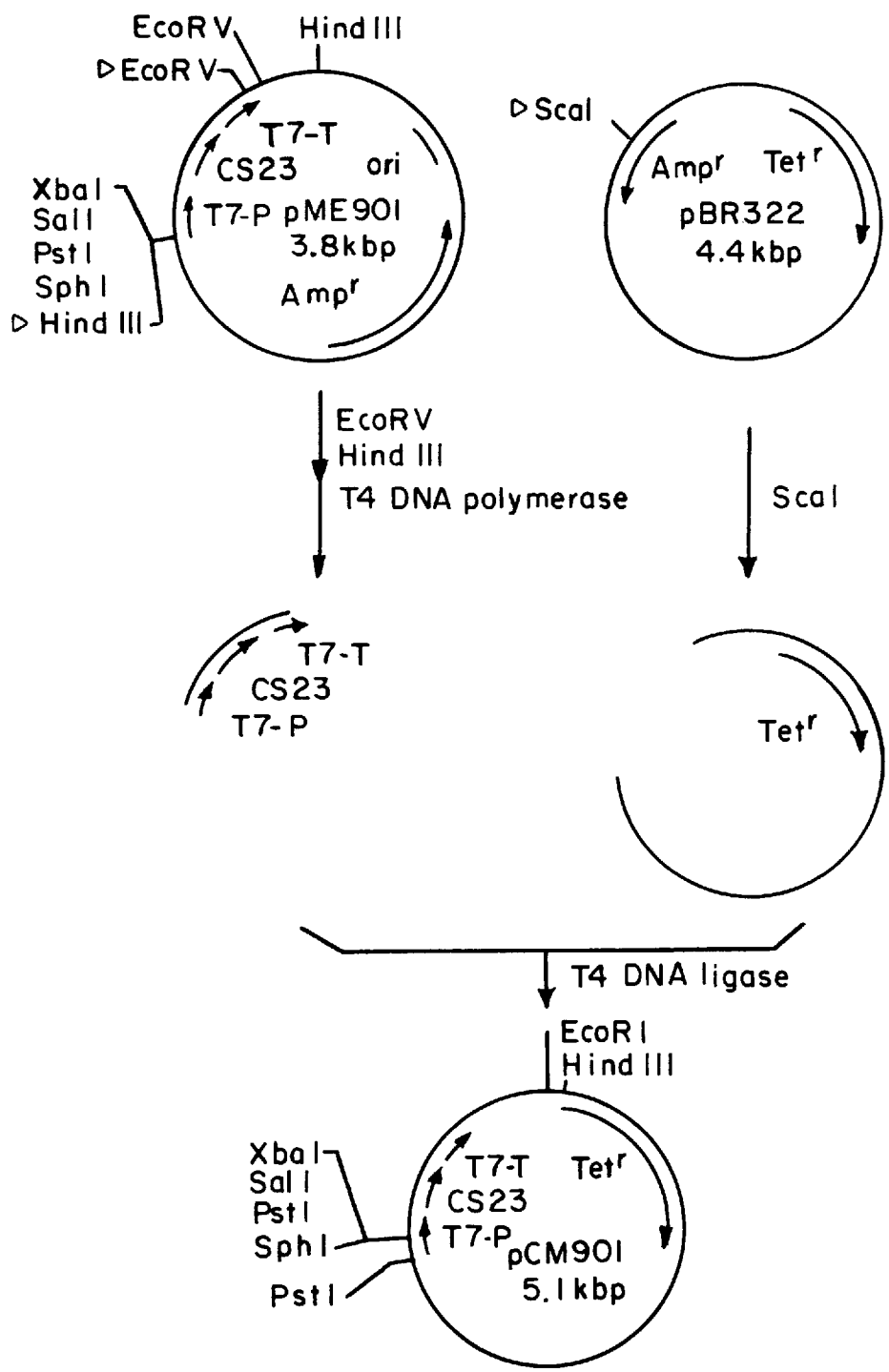
FIG. 7 shows the construction scheme for the plasmid pCM901 obtained in Reference Example 1.

The plasmid pTB 762, which incorporates a gene code for the rhbFGF mutein CS23, resulting from replacement of the 69- and 87-cysteine residues of the four cysteine residues in hbFGF by serine residues [Seno et al., Biochemical and Biophysical Research Communication, 151, 701–708 (1988); European Patent Publication No. 281, 822], was completely digested with Ava I and Pst I to yield an about 0.45 kbp fragment containing most of the rhbFGF mutein CS23. This fragment was ligated with synthetic DNA GATCTGC (ACGTCTAGACG), using T4 DNA ligase, followed by digestion with Ava I and Pst I to yield fragment A wherein the Pst I cleavage site had been changed to a Bgl II cleavage site. Next, the plasmid pTB955 [Seno et al., European Journal of Biochemistry, 188, 239–245 (1990)], which incorporates a gene coded for the rhbFGF mutein CS128 resulting from a C-terminal deletion from hbFGF, was completely digested with Sal I and BamH I to yield an about 4.1 kbp fragment B. Also, pTB955 was completely digested with Ava I and Sal I to yield an about 390 bp fragment C. These three fragments were ligated using T4 DNA ligase to yield pHP901, an expression plasmid having an ampicillin resistance marker (FIG. 5).

pHP901 was completely digested with EcoR I and Bgl II to yield an about 1.1 kbp fragment containing a gene coded for the rhbFGF mutein CS23, a T7 promoter and a T7 terminator. Using T4 DNA ligase, this fragment was ligated with pUC18 as completely digested with EcoR I and BamH I to yield the plasmid pME901 (FIG. 6).

pME901 was completely digested with EcoR V and Hind III to yield an about 0.77 kbp fragment containing a gene coded for the rhbFGF mutein CS23, a T7 promoter and a T7 terminator, followed by terminal smoothing using T4 DNA polymerase. Using T4 DNA ligase, this fragment was ligated with pBR322 as digested with Sca I to yield pCM901, an expression plasmid having a tetracycline resistance marker (FIG. 7).

Example 1

Figure 9:
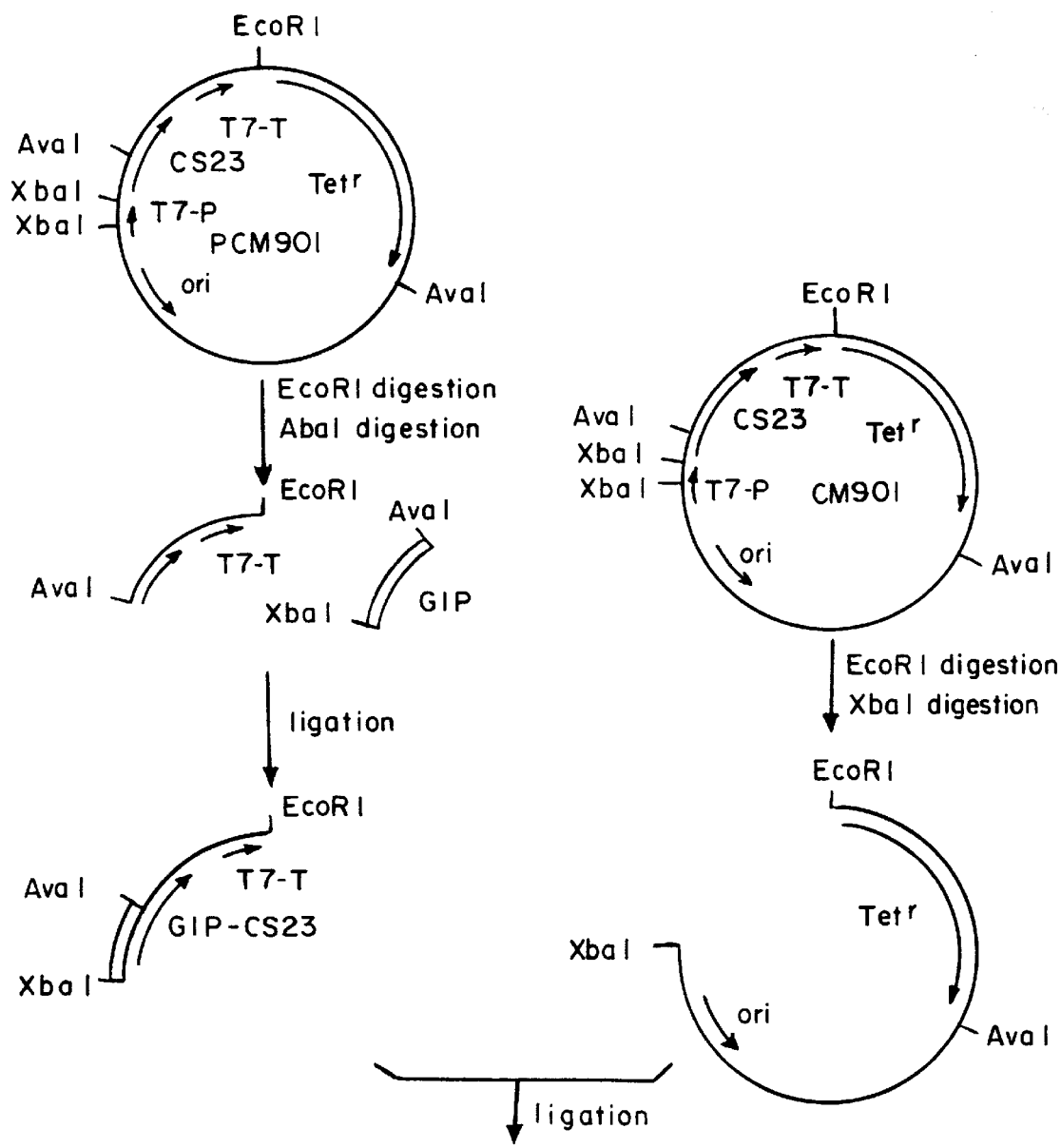
FIGS. 9 and 10 show the construction scheme for the plasmid pGS23 obtained in Example 1.
Figure 10:
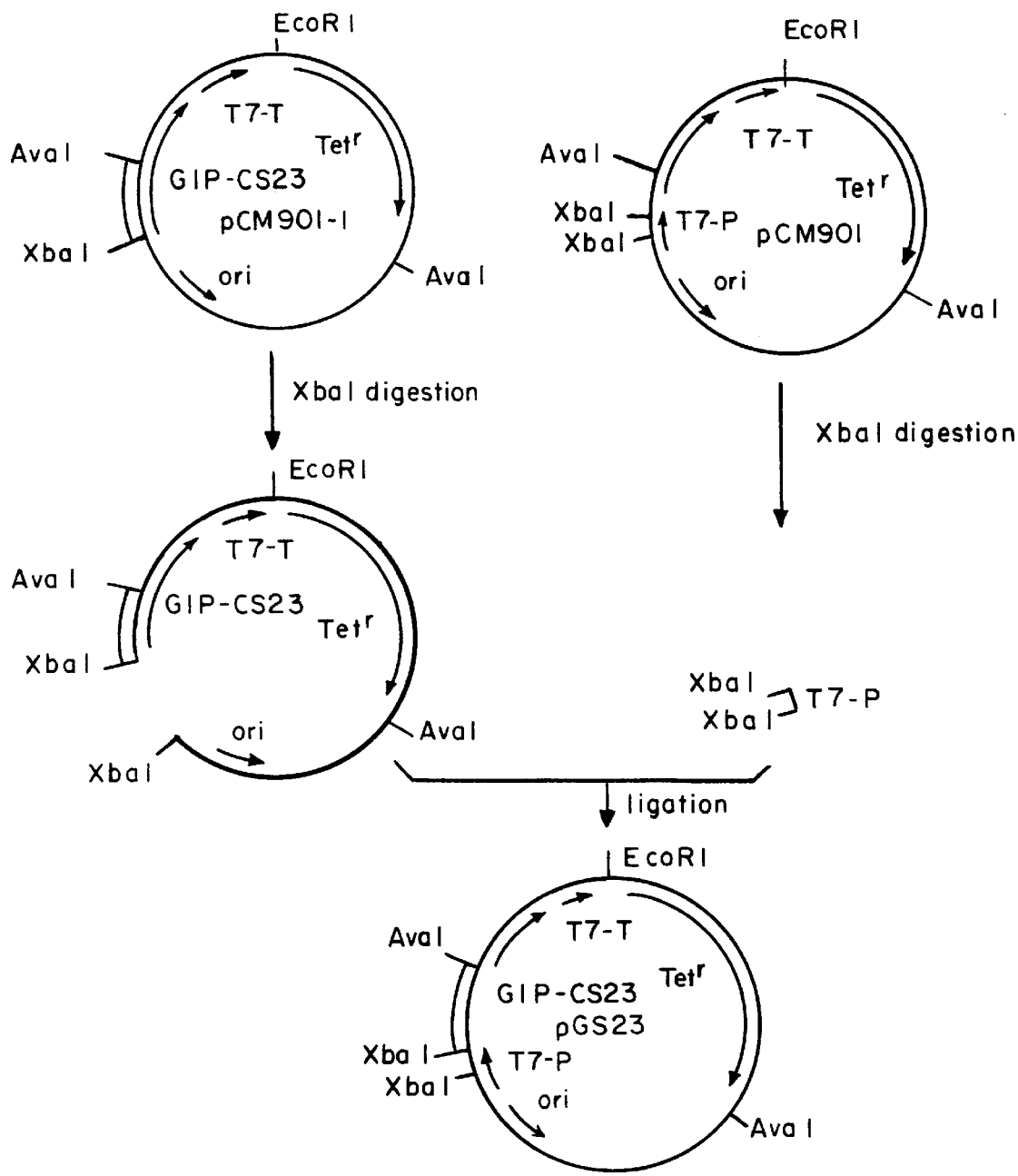

Preparation of recombinant which produces GIP-CS23 fused protein pCM901, the rhbFGF mutein CS23 expression plasmid obtained in Reference Example 1, is digested with restriction enzymes EcoR I and Ava I to yield a fragment containing a CS-23 gene region and a T7-promoter. Using T4 DNA ligase, this fragment is ligated to a GIP gene fragment having an Xba I cleavage site at its 5'-terminal and an Ava I cleavage site at its 3'-terminal, shown in FIG. 8, synthesized using a DNA synthesizer (ABI Company, 381A) to yield a GIP-CS23 fused gene fragment. Using T4 DNA ligase, this fragment is inserted into pCM901, as digested with restriction enzymes EcoR I and Xba I, to yield pCM901-1. To the Xba I cleavage site of this plasmid, the T7-promoter cleaved out of pCM-901 using restriction enzyme Xba I is inserted to yield the expression plasmid pGS23 (FIGS. 9 and 10). This plasmid is used to transform the *Escherichia coli* MM294(DE3) strain to yield *Escherichia coli* MM294(DE3)/pGS23, a recombinant carrying the rhGIP-CS23 fused gene shown in FIG. 11 and FIG. 12.

Example 2
Cultivation of recombinant

To 30 ml of a medium prepared by adding 5 mg/l tetracycline to LB medium (10 g/l Bacto Tryptone, 5 g/l Bacto yeast extract, 5 g/l sodium chloride), one loopful of recombinant *Escherichia coli* MM294(DE3)/pGS23 is inoculated, followed by shaking the culture at 37° C. overnight. A 1.5 ml quantity of this culture broth is transferred to 30 ml of a medium prepared by adding 15 g/l glucose, 15 g/l casamino acid, 1 mg/l thiamine hydrochloride and 5 mg/l tetracycline to M-9 medium (16.8 g/l $Na_2HPO_4 \cdot 12H_2O$, 3 g/l $KH_2PO_4$, 1 g/l $NH_4Cl$, 0.5 g/l sodium chloride, 0.246 g/l $MgSO_4 \cdot 7H_2O$), followed by shaking the culture at 37° C. When the turbidity reached 100 to 120 Klett units, IPTG is added, followed by cultivation for 4 more hours. Cells are collected by centrifugation and stored at −20° C.

Example 3
Purification of GIP-CS23 fused protein

Cells (*Escherichia coli* MM294(DE23)/pGS23) stored at −20° C., which is obtained in Example 2, are suspended in an extraction buffer comprising a 25 mM phosphate buffer (pH 6.0)+0.1 mM APMSF (p-amidinophenylmethanesulfonyl fluoride hydrochloride) +2 mM DTT (dithiothreitol). Using glass beads, the suspended cells are disrupted under ice cooling conditions in the Dynomill (KD-S model, Willey Buchofen, Switzerland). The resulting extract is centrifuged (model 21, Beckman Instrument, USA). The resulting supernatant is adsorbed to Heparin-5PW (7.5 mm ID×75 mm, Tosoh Corporation) which is equilibrated with 50 mM phosphate buffer (pH 6.0), followed by elution on a linear density gradient between 50 mM phosphate buffer (pH 6.0) and 50 mM phosphate buffer (pH 6.0)+2M sodium chloride. The main eluted fraction is adsorbed to ODP-50 (4.6 mm ID×150 mm, Asahi Chemical) which is equilibrated with 0.1% trifluoroacetic acid, followed by elution on a linear density gradient between 0.1% trifluoroacetic acid and 0.1% trifluoroacetic acid+80% acetonitrile. The main eluted fraction is treated using a centrifugal reduced pressure condenser (lyophilizer) (Servant Company, USA) to yield a dry standard preparation of purified GIP-CS23 fused protein.

Example 4
Separation of GIP from GIP-CS23 fused protein

The GIP-CS23 fused protein is dissolved in a 0.2M Tris-acetic acid buffer (pH 8.0) containing 6M guanidine hydrochloride+10 mM dithiothreitol, followed by incubation at 37° C. for 1 to 2 hours. After adding 2-nitro-5-thiocyanobenzoic acid in an amount 5 to 10 times the total amount of all thiol groups, the pH of the mixture is readjusted to 8.0 with sodium hydroxide. Then, reaction is carried out at 37° C. for 15 minutes. After adding acetic acid to reduce the pH to below 4 and cooling the mixture to 4° C., desalting is carried out by dialysis or gel filtration (50% acetic acid). After lyophilization using a centrifugal reduced pressure condenser (Servant Company, USA), the main eluted fraction is dissolved in 0.01N acetic acid and adjusted to a pH of 6.4 with 5% ammonia. This solution is adsorbed to CM-5PW (7.5 mm ID×75 mm, Tosoh Corporation), followed by elution on a linear density gradient between 0.01M ammonium acetate and 0.2M ammonium acetate. After lyophilization using a centrifugal reduced pressure condenser (Servant Company, USA), the main eluted fraction is dissolved in 0.1% TFA. This solution is adsorbed to Nucleosil 5C18 (10 mm ID×2.5 cm), followed by elution on a linear density gradient between 0.1% TFA and 0.1% TFA+80% acetonitrile. The main eluted fraction is lyophilized using a centrifugal reduced pressure condenser (Servant Company, USA) to yield a dry standard preparation of purified GIP.

Example 5

Figure 13:
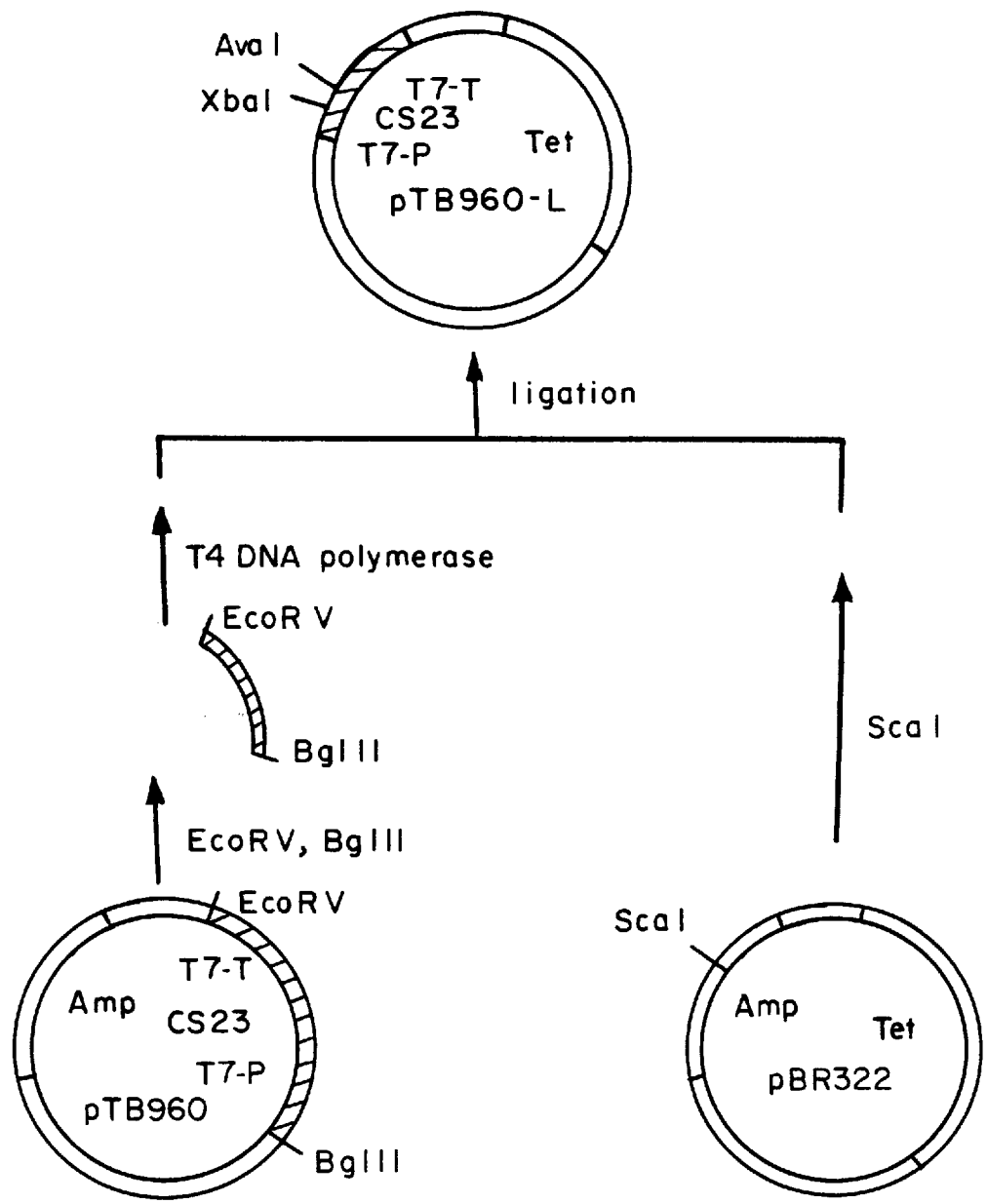
FIG. 13 shows the construction scheme for the plasmid pTB960-1 obtained in Example 5.
Figure 14:
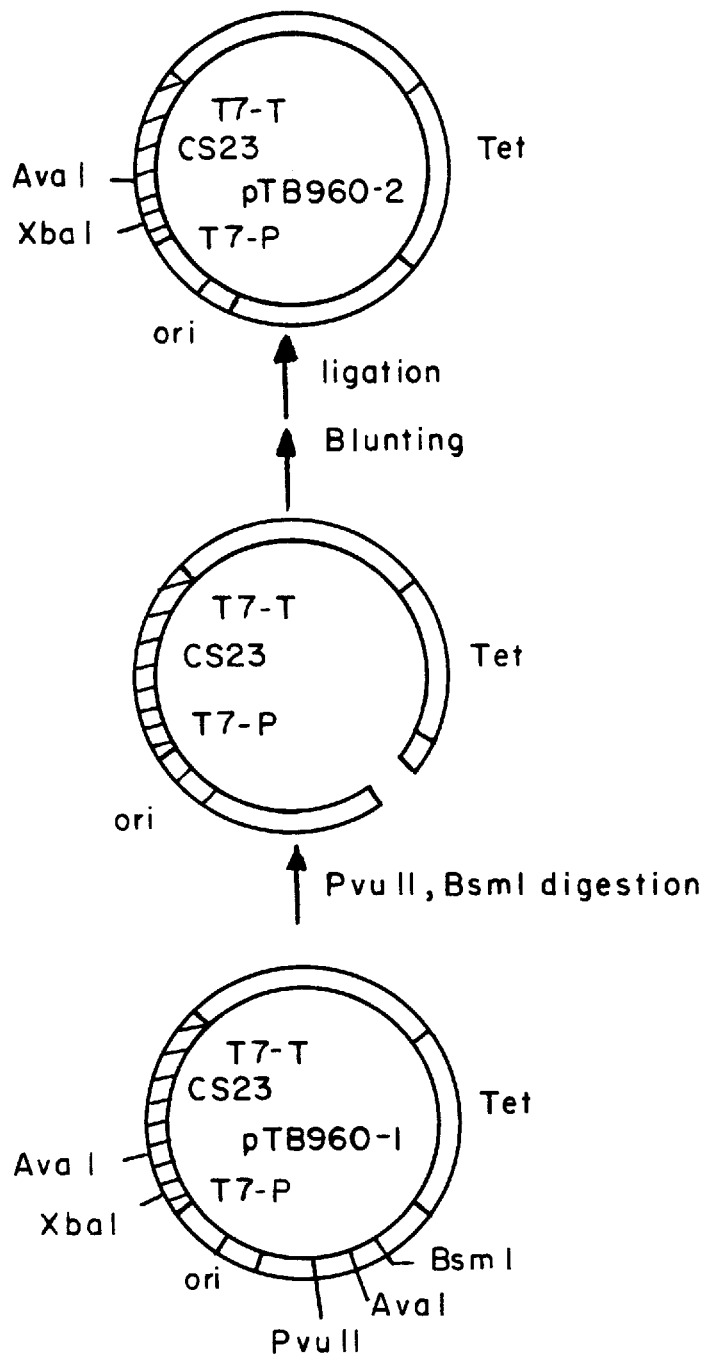
FIG. 14 shows the construction scheme for the plasmid pTB960-2 obtained in Example 5.

(1) Preparation of recombinant with tetracycline resistance marker which produces rhbFGF mutein CS23 pTB960 as obtained by the method described in PCT International Patent Publication No. WO91/09126 was cleaved with EcoR V and Bgl II. The resulting fragment, containing an rhbFGF mutein CS23 structural gene, was treated with T4 DNA polymerase to blunt its ends. This fragment was ligated with Sca I-digested pBR322 using T4 DNA ligase to yield pTB960-1 (FIG. 13).

pTB960-1 was further cleaved with Bsm I and Pvu II. After blunting both fragment ends using T4 DNA polymerase, ligation was carried out using T4 DNA ligase to yield pTB960-2, an expression plasmid having a tetracycline resistance marker (FIG. 14).

Figure 15:
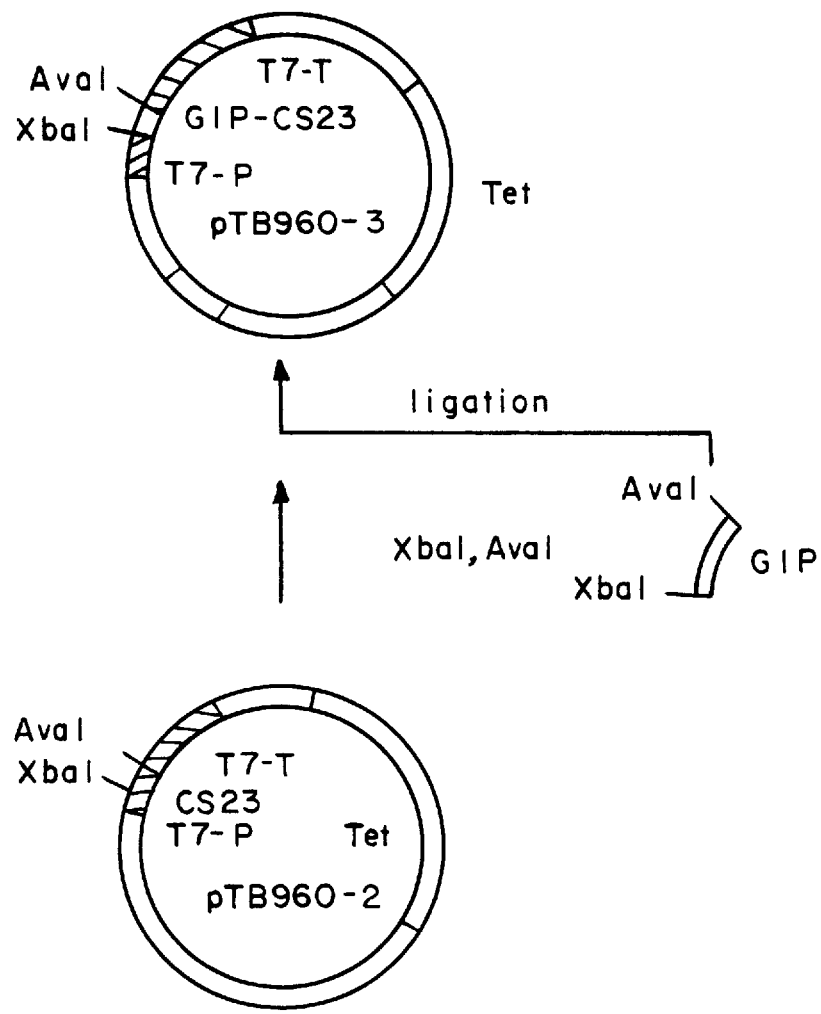
FIG. 15 shows the construction scheme for the plasmid pTB960-3 obtained in Example 5.

(2) Preparation of recombinant which produces GIP-CS23 fused protein pTB960-2, the rhbFGF mutein CS23 expression plasmid obtained in (1) above, was digested with Xba I and Ava I. Using T4 DNA ligase, this fragment was ligated with a GIP gene fragment (SEQ ID NO:5) having an Xba I cleavage site at its 5'-terminal and an Ava I cleavage site at its 3'-terminal, shown in FIG. 8, synthesized using a DNA synthesizer (ABI Company, 381A), to yield the plasmid pTB960-3 (FIG. 15). This expression plasmid pTB960-3 was used to transform *Escherichia coli* MM294(DE3) strain to yield *Escherichia coli* MM294(DE3)/pTB960-3 (IFO 15241, FERM BP-3615), a recombinant carrying the rhGIP-hbFGF mutein CS23 gene (hereinafter also referred to as GIP-CS23) fused protein (shown in FIGS. 11 and 12).

(3) Cultivation of recombinant

To 30 ml of a medium prepared by adding 5 mg/l tetracycline to LB medium (10 g/l Bacto Tryptone, 5 g/l Bacto yeast extract, 5 g/l sodium chloride), one loopful of the recombinant *Escherichia coli* MM294(DE3)/pTB960-3 obtained in (2) above was inoculated, followed by shaking culture at 37° C. overnight. A 1.5 ml quantity of this culture broth was transferred to 30 ml of a medium prepared by adding 15 g/l glucose, 15 g/l casamino acid, 1 mg/l thiamine hydrochloride and 5 mg/l tetracycline to M-9 medium (16.8 g/l $Na_2HPO_4 \cdot 12H_2O$, 3 g/l $KH_2PO_4$, 1 g/l $NH_4Cl$, 0.5 g/l sodium chloride, 0.246 g/l $MgSO_4 \cdot 7H_2O$), followed by shaking culture at 37° C. When the turbidity reached 100 to 120 Klett units, IPTG was added, followed by cultivation for 4 more hours. Cells were collected by centrifugation and stored at −20° C.

(4) Purification of GIP-CS23 fused protein

Cells of the recombinant *Escherichia coli* MM294(DE23)/pTB960-3, stored at −20° C., obtained in (3) above, were suspended in an extraction buffer comprising 25 mM phosphate buffer (pH 6.0)+0.1 mM APMSF (p-amidinophenylmethanesulfonyl fluoride hydrochloride)+2 mM DTT (dithiothreitol)+50 μg/ml lysozyme. After standing under ice cooling conditions for 1 hour, this suspension was treated under ice cooling conditions in an ultrasonic cell disrupter (Insonater, model 200M, Kubota, Ltd.) for 10 minutes. The resulting crude extract was centrifuged using a centrifuge (model J2-21, Beckman Instrument, USA). The resulting precipitate (GIP-CS23 fused protein inclusion body) was washed with 25 mM phosphate buffer, after which it was suspended in a 0.2M Tris-HCl buffer (pH 8.0) containing 2% SDS or 6M guanidine hydrochloride and 100 mM DTT, followed by heat treatment at 100° C. for 5 minutes for solubilization. The resulting soluble protein was adsorbed to a column of phenyl 5PW RP (4.5 mm ID×7.5 cm, Tosoh Corporation) equilibrated with 0.1% trifluoroacetic acid, followed by elution on a linear density gradient between 0.1% trifluoroacetic acid and 0.1% trifluoroacetic acid+80% acetonitrile. The main eluted fraction was evaporated under reduced pressure using a centrifugal reduced pressure condenser (lyophilizer) (Servant Company, USA) to yield a dry standard of purified GIP-CS23 fused protein preparation.

(5) Separation of GIP from GIP-CS23 fused protein

The GIP-CS23 fused protein was dissolved in a 0.2M Tris-acetic acid buffer (pH 8.0) containing 6M guanidine hydrochloride+10 mM dithiothreitol, followed by incubation at 37° C. for 1 to 2 hours. After adding 2-nitro-5-thiocyanobenzoic acid in an amount 5 to 10 times the total amount of all thiol groups, the pH of the mixture was readusted to 8.0 with sodium hydroxide. Then, reaction was carried out at 37° C. for 15 minutes. After adding acetic acid to reduce the pH below 4 and cooling the mixture to 4° C., desalting was carried out by dialysis or gel filtration (50% acetic acid). After lyophilization using a centrifugal reduced pressure condenser (Servant Company, USA), the main eluted fraction was dissolved in a 0.2M Tris-HCl buffer (pH 9.0) containing 6M guanidine hydrochloride, followed by incubation at 37° C. for 12 hours.

Then, this solution was filtered through a 10 KD membrane (Centricon, Amicon Corporation). The resulting fraction under 10 KD was adsorbed to a column of phenyl 5PW RP (4.5mm ID×7.5cm, Tosoh Corporation) equilibrated with 0.1% TFA+24% acetonitrile, followed by elution on a linear density gradient between 0.1% TFA+24% acetonitrile and 0.1% TFA+80% acetonitrile. After lyophilization using a centrifugal reduced pressure condenser (Servant Company, USA), the main eluted fraction was dissolved in 20 mM phosphate buffer (pH6.5). The resulting crude GIP solution was absorbed to a column of CM-5PW (7.5mm ID×7.5 cm, Tosoh Corporation) equilibrated with 20 mM phosphate buffer, followed by elution on a linear density gradient between 20 mM phosphate buffer (pH 6.5) and 20 mM phosphate buffer (pH 6.5)+1.0M NaCl. The resulting main eluted fraction was absorbed to a column of ODS-120T (7.8 mm ID×30 cm, Tosoh Corporation) equilibrated with 0.1% TFA, followed by elution on a linear density gradient between 0.1% TFA and 0.1% TFA+80% acetonitrile. The main eluted fraction was lyophilized using a centrifugal reduced pressure condenser (Servant Company, USA) to yield a dry standard preparation of purified GIP.

(6) Amino acid analysis of rhGIP

The rhGIP obtained in (5) above was analyzed for N-terminal amino acid sequence using the model 477A protein sequencer (Applied Biosystems). An hGIP sequence with Met added to its N-terminal was detected (Table 2). Its amino acid composition was determined using the model 6330 amino acid analyzer (Beckman). The values obtained agreed with the theoretical values (Table 3).

TABLE 2

N-terminal Amino Acid Sequencing

| Number of cycles | GIP amino acid sequence | Amino acid expected from base sequence |
|---|---|---|
| 1 | Met | Met |
| 2 | Tyr | Tyr |
| 3 | Ala | Ala |
| 4 | Glu | Glu |
| 5 | Gly | Gly |
| 6 | Thr | Thr |
| 7 | Phe | Phe |
| 8 | Ile | Ile |
| 9 | Ser | Ser |
| 10 | Asp | Asp |
| 11 | Tyr | Tyr |
| 12 | Ser | Ser |
| 13 | Ile | Ile |
| 14 | Ala | Ala |
| 15 | Met | Met |
| 16 | Asp | Asp |
| 17 | Lys | Lys |
| 18 | Ile | Ile |
| 19 | His | His |
| 20 | Gln | Gln |

Analyzed using the model 477A protein sequencer (Applied Biosystems).

TABLE 3

Determination of Amino Acid Composition

| Amino acid | rhGIP | Theoretical value |
|---|---|---|
| Asp/Asn | 6.8 | 7 |
| Thr | 1.9 | 2 |
| Ser | 1.7 | 2 |
| Glu/Gln | 5.1 | 5 |
| Gly | 1.9 | 2 |
| Ala | 2.8 | 3 |
| Val | 0.8 | 1 |
| Met | 2.0 | 2 |
| Ile | 3.8 | 4 |
| Leu | 1.8 | 2 |
| Tyr | 1.7 | 2 |
| Phe | 2.0 | 2 |
| His | 2.1 | 2 |
| Lys | 4.9 | 5 |
| Trp | 1.9 | 2 |

Acid hydrolysis was performed with 6N hydrochloric acid (110° C., 24 hours). Amino acid ratios were determined with the model 6330 amino acid analyzer (Beckman).
Determined by the Edelhoch method.

(7) Thin-layer chromatography of rhGIP

The rhGIP obtained in (5) above was analyzed using silica gel (Kieselgel, Merck & Co., Inc.) and a thin-layer plate of cellulose (Avicel SF, Funakoshi Yakuhin K. K.). The developing solvent used was n-butanol: pyridine: acetic acid: water in the ratio of 4: 1: 1: 2. The $Rf_1$ value (silica gel) was found to be 0.30 and the $Rf_2$ value (cellulose) 0.43.

Example 6

Figure 17:
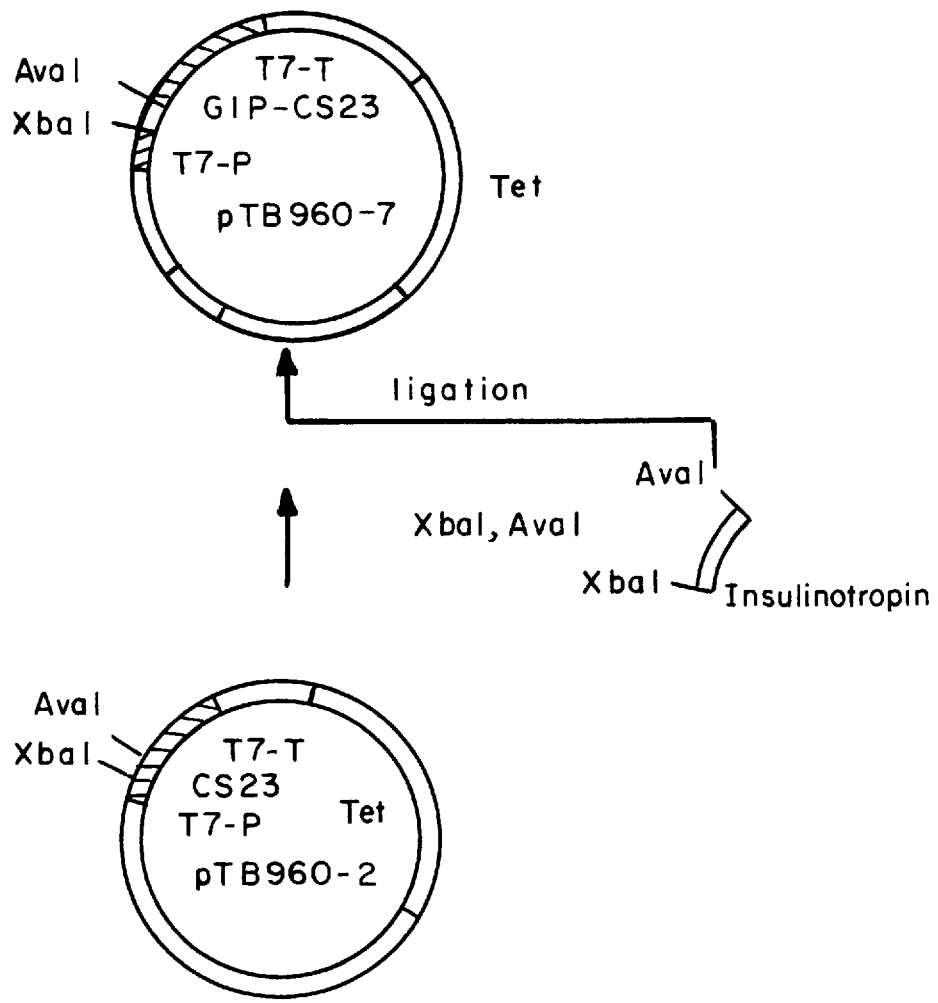
FIG. 17 shows the construction scheme for the plasmid pTB960-7 obtained in Example 6.

(1) Preparation of recombinant which produces GLP-I (7-37)-CS23 fused protein pTB960-2, the rhbFGF mutein CS23 expression plasmid obtained in Example 5 (1) above, was digested with Xba I and Ava I. Using T4 DNA ligase, this fragment was ligated to a GLP-I (7-37) (sometimes referred to as "Insulinotropin) gene fragment having an Xba I cleavage site at its 5'-terminal and an Ava I cleavage site at its 3'-terminal, shown in FIG. 16, synthesized using a DNA synthesizer (ABI Company, 381A), to yield the plasmid pTB960-7 (FIG. 17). This expression plasmid pTB960-7 was used to transform *Escherichia coli* MM294(DE3) strain to yield *Escherichia coli* MM294(DE3)/pTB960-7 (IFO 15254, FERM BP-3690), a recombinant carrying the GLP-I (7-37)-hbFGF mutein CS23 gene (hereinafter also referred to as Insulinotropin-CS23) fused protein (shown in FIGS. 18).

(2) Cultivation of recombinant

To 30 ml of a medium prepared by adding 5 mg/l tetracycline to LB medium (10 g/l Bacto Tryptone, 5 g/l Bacto yeast extract, 5 g/l sodium chloride), one loopful of the recombinant *Escherichia coli* MM294(DE3)/pTB960-7 obtained in (1) above was inoculated, followed by shaking culture at 37° C. overnight. A 1.5 ml quantity of this culture broth was transferred to 30 ml of a medium prepared by adding 15 g/l glucose, 15 g/l casamino acid, 1 mg/l thiamine hydrochloride and 5 mg/l tetracycline to M-9 medium (16.8 g/l $Na_2HPO_4 \cdot 12H_2O$, 3 g/l $KH_2PO_4$, 1 g/l $NH_4C$, 0.5 g/l sodium chloride, 0.246 g/l $MgSO_4 \cdot 7H_2O$), followed by shaking culture at 37° C. When the turbidity reached 100 to 120 Klett units, IPTG was added, followed by cultivation for 4 more hours. Cells were collected by centrifugation and stored at −20° C.

(3) Purification of Insulinotropin-CS23 fused protein

Cells of the recombinant *Escherichia coli* MM294(DE23)/pTB960-7, stored at −20° C., obtained in (2) above, were suspended in an extraction buffer comprising 25 mM phosphate buffer (pH 6.0)+0.1 mM APMSF (p-amidinophenylmethanesulfonyl fluoride hydrochloride) +2 mM DTT (dithiothreitol)+50 µg/ml lysozyme. After standing under ice cooling conditions for 1 hour, this suspension was treated under ice cooling conditions in an ultrasonic cell disrupter (Insonater, model 200M, Kubota, Ltd.) for 10 minutes. The resulting crude extract was centrifuged using a centrifuge (model J2-21, Beckman Instrument, USA). The resulting precipitate 35 (Insulinotropin-CS23 fused protein inclusion body) was washed with 25 mM phosphate buffer, after which it was suspended in a 0.2M Tris-HCl buffer (pH 8.0) containing 2% SDS or 6M guanidine hydrochloride and 100 mM DTT, followed by heat treatment at 100° C. for 5 minutes for solubilization. The resulting soluble protein was adsorbed to a column of phenyl 5PW RP (4.5 mm ID×7.5 cm, Tosoh Corporation) equilibrated with 0.1% trifluoroacetic acid, followed by elution on a linear density gradient between 0.1% trifluoroacetic acid and 0.1% trifluoroacetic acid+80% acetonitrile. The main eluted fraction was evaporated under reduced pressure using a centrifugal reduced pressure condenser (lyophilizer) (Servant Company, USA) to yield a dry standard of purified Insulinotropin-CS23 fused protein preparation.

(4) Separation of Insulinotropin from Insulinotropin-CS23 fused protein The Insulinotropin-CS23 fused protein was dissolved in a 0.2M Tris-acetic acid buffer (pH 8.0) containing 6M guanidine hydrochloride+10 mM dithiothreitol, followed by incubation at 37° C. for 1 to 2 hours. After adding 2-nitro-5-thiocyanobenzoic acid in an amount 5 to 10 times the total amount of all thiol groups, the pH of the mixture was readjusted to 8.0 with sodium hydroxide. Then, reaction was carried out at 37° C. for 15 minutes. After adding acetic acid to reduce the pH to below 4 and cooling the mixture to 4° C., desalting was carried out by dialysis or gel filtration (50% acetic acid). After lyophilization using a centrifugal reduced pressure condenser (Servant Company, USA), the main eluted fraction was dissolved in a 0.2M Tris-HCl buffer (pH 9.0) containing 6M guanidine hydrochloride, followed by incubation at 37° C. for 12 hours.

Then, this solution was filtered through 10 KD membrane (Centricon, Amicon Corporation). The resulting fraction containing smaller particles than 10 KD was absorbed to a column of phenyl 5 PW RP (4.5 mm ID×7.5 cm, Tosoh Corporation) equilibrated with 0.1% TFA+20% acetonitrile, followed by elution on a linear density gradient between 0.1% TFA+20% acetonitrile and 0.1% TFA+80% acetonitrile. After lyophilization using a centrifugal reduced pressure condenser (Servant Company, USA), the main eluted fraction was dissolved in 20 mM phosphate buffer (pH 6.5). The resulting crude Insulinotropin solution was absorbed to a column of CM-5PW (7.5 mmID×7.5 cm, Tosoh Corporation) equilibrated with 20 mM phosphate buffer, followed by elution on a linear density gradient between 20 mM phosphate buffer (pH 6.5) and 20 mM phosphate buffer (pH 6.5)+1.0M NaCl. The resulting main eluted fraction was absorbed to a column of ODS-120T (7.8 mm ID×30 cm, Tosoh Corporation) equilibrated with 0.1% TFA, followed by elution on a linear density gradient between 0.1% TFA and 0.1% TFA+80% acetonitrile. The main eluted fraction was lyophilized using a centrifugal reduced pressure condenser (Servant Company, USA) to yield a dry standard preparation of purified Insulinotropin.

(6) Amino acid analysis of Insulinotropin

Insulinotropin obtained in (5) above was analyzed for N-terminal amino acid sequence using the model 477A protein sequencer (Applied Biosystems). An Insulinotropin sequence with Met added to its N-terminal was detected (Table 4). Its amino acid composition was determined using the model 6330 amino acid analyzer (Beckman) by hydrolysis method with hydrochloric acid. The values obtained agreed with the theoretical values (Table 5).

TABLE 4

Amino acid sequence of N-terminal of Insulinotropin

| Cycle No. | Amino acid sequence of Insulinotropin | Amino acid deduced from base sequence |
| --- | --- | --- |
| 1 | Met | Met |
| 2 | His | His |
| 3 | Ala | Ala |
| 4 | Glu | Glu |
| 5 | Gly | Gly |
| 6 | Thr | Thr |
| 7 | Phe | Phe |
| 8 | Thr | Thr |
| 9 | Ser | Ser |
| 10 | Asp | Asp |
| 11 | Val | Val |
| 12 | Ser | Ser |
| 13 | Ser | Ser |
| 14 | Tyr | Tyr |
| 15 | Leu | Leu |
| 16 | Glu | Glu |
| 17 | Gly | Gly |
| 18 | Gln | Gln |
| 19 | Ala | Ala |
| 20 | Ala | Ala |

TABLE 5

Amino acid composition of Insulinotropin

| Amino acid | Value obtained | Theoretical value |
|---|---|---|
| Asp/Asn | 0.95 | 1 |
| Thr | 2.09 | 2 |
| Ser | 2.98 | 3 |
| Glu/Gln | 4.20 | 4 |
| Gly | 4.05 | 4 |
| Ala | 3.95 | 4 |
| Val | 1.80 | 2 |
| Met | 1.12 | 1 |
| Ile | 1.08 | 1 |
| Leu | 2.10 | 2 |
| Tyr | 0.90 | 1 |
| Phe | 2.20 | 2 |
| His | 0.97 | 1 |
| Lys | 1.92 | 2 |
| Arg | 0.90 | 1 |
| Trp | N.D. | 1 |

N.D.: Not Determined.

Example 7

(I) Production of a gene coding for human PTH (a) Synthesis of DNA Fragments

Fourteen DNA fragments #1 to #14 shown in FIG. 19 were synthesized using properly protected DNA β-cyanoethylphosphoamidite and using an automatic synthesizer (Model 380A, Applied Biosystems). The protocol for synthesis specified by Applied Biosystems was used. The protected DNA oligomer-resins thus synthesized (0.2 μmole of the resin) were heated in 2 ml of concentrated aqueous ammonia at 60° C. for 6 hours. The resulting products were purified by reversed phase high performance liquid chromatography (hereinafter referred to as HPLC) to obtain DNA oligomers only the 5'-terminal hydroxyl groups of which were protected by dimethoxytrityl groups. These DNA oligomers were treated with 2 ml of 80% acetic acid for 20 minutes to remove the terminal dimethoxytrityl groups, and the resulting products were purified by reversed phase HPLC and ion exchange HPLC. The fourteen DNA oligomers thus synthesized are as shown in FIG. 19.

(b) Phosphorylation of DNA oligomers

Each of the twelve DNA oligomers #2 to #13 (except for #1 and #14) which were to form the 5'-termini was reacted in 25 μl of a phosphorylation reaction solution [10 μl of the DNA oligomer, 50 mM Tris-HCl (pH 7.6), 10 mM MgCl$_2$, 1 mM spermidine, 10 mM dithiothreitol (hereinafter referred to as DTT), 0.1 mg/ml bovine serum albumin (hereinafter referred to as BSA), 1 mM ATP, 10 units of T4 polynucleotide kinase (Takara Shuzo)] at 37° C. for 1 hour to phosphorylate the 5'-terminus. This reaction solution was treated at 65° C. for 10 munutes, followed by freezing and thawing. The resulting product was subjected to the following reaction.

(c) Ligation of DNA Fragments (Refer to FIGS. 20 and 21)

(c-1) A series of stages for forming a doubel stranded structure of an hPTH gene are as shown in FIG. 20 in which the mark ⊢ indicates that a 5'-terminal hydroxyl group is phosphorylated. For example, the ligation of block I was carried out as follows. 7.5 μl portions of the phosphorylated reaction solutions of the five DNA fragments (corresponding to DNA fragments #2 to #6) obtained by the operation described in the above item 2 were combined with 2.5 μg of DNA fragment #1 corresponding to the 5'-terminus to 50 μl. Then, 5 units of T4 DNA ligase (New England Biolabs) was added thereto, followed by incubation at 14° C. for 5 hours. The resulting produt was thereafter treated at 65° C. for 10 minutes to terminate the reaction, thus obtaining block I. Blocks II and m were similarly prepared. 20 portions of these block I to III were mixed and 5 units of T4 DNA ligase was added thereto, followed by incubation at 14° C. for 20 hours. The resulting product was treated at 65° C. for 10 minutes to terminate the reaction.

The product thus obtained was subejcted to electrophoresis on a 7.5% polyacrylamide gel in a buffer (pH 8.3, 100 mM Tris-HCl, 100 mM borate, 2 mM EDTA) at 160 V for 1.5 hours. After electrophoresis, the gel was stained with 0.6 mg/e ethidium bromide (EtBr). Gel fragments containing 263-bp DNA fragments were sealed in a dialysis tube and submerged in a buffer for electrophoresis. Then, the DNA fragments were electrically eluted from the gel [*J. Mol. Biol.* 110, 119 (1977)]. A solution in this dialysis tube was recovered and poured on an Elutip-d column (Schleicher & Schnell) previously buffer with a solution containing 0.2M NaCl, 20 mMTris-HCl (pH 7.4) and 1.0 mM EDTA to allow the DNA fragment to be adsorbed. Then, the DNA fragments were eluted with a solution containing 1.0M NaCl, 20 mM Tris-HCl (pH 7.4) and 1.0 mM EDTA. Twice as much ethanol as the eluate was added to the eluate, and the mixture was cooled to −20° C. Then, the DNA fragments were precipitated by centrifugation.

(c-2) A series of stages for forming a double stranded structure of an hPTH gene can also be achieved by a process shown in FIG. 21 in which the mark ⊢ indicates that a 5'-terminal hydroxyl group is phosphorylated. 5 μl portions of the phosphorylated reaction solutions of the twelve kinds of DNA fragments (corresponding to DNA fragments #2 to #13) obtained in the above item 2 were combined with 2 μg of DNA fragments #1 and #14 corresponding to the 5'-terminus to 50 μl. Then, 5 units of T4 DNA ligase (Takara Shuzo) was added thereto, followed by incubation at 15° C. for 20 hours.

The product thus obtained was subjected to electrophoresis on an 8% polyacrylamide gel in a buffer (pH 8.3, 100 mM Tris-HCl, 100 mM boric acid, 2 mM EDTA) at 125 V for 2 hours. After electrophoresis, the gel was stained with 0.6 mg/l EtBr. Gel fragments containing 263-bp DNA fragments were sealed in a dialysis tube and submerged in a buffer for electrophoresis. Then, the DNA fragments were electrically eluted from the gel. A solution in this dialysis tube was subjected to phenol treatment twice, followed by recovery of an aqueous layer (an upper layer). Then, twice as much ethanol as the aqueous layer was added thereto, and the mixture was cooled to −70° C. The DNA fragments were thereafter precipitated by centrifugation. Thus, about 1 μg of the DNA fragments was obtained. After phosphorylation with T4 polynucleotide kinase (Takara Shuzo), the DNA fragments were subjected to the following experiment (d-2).

Figure 22:
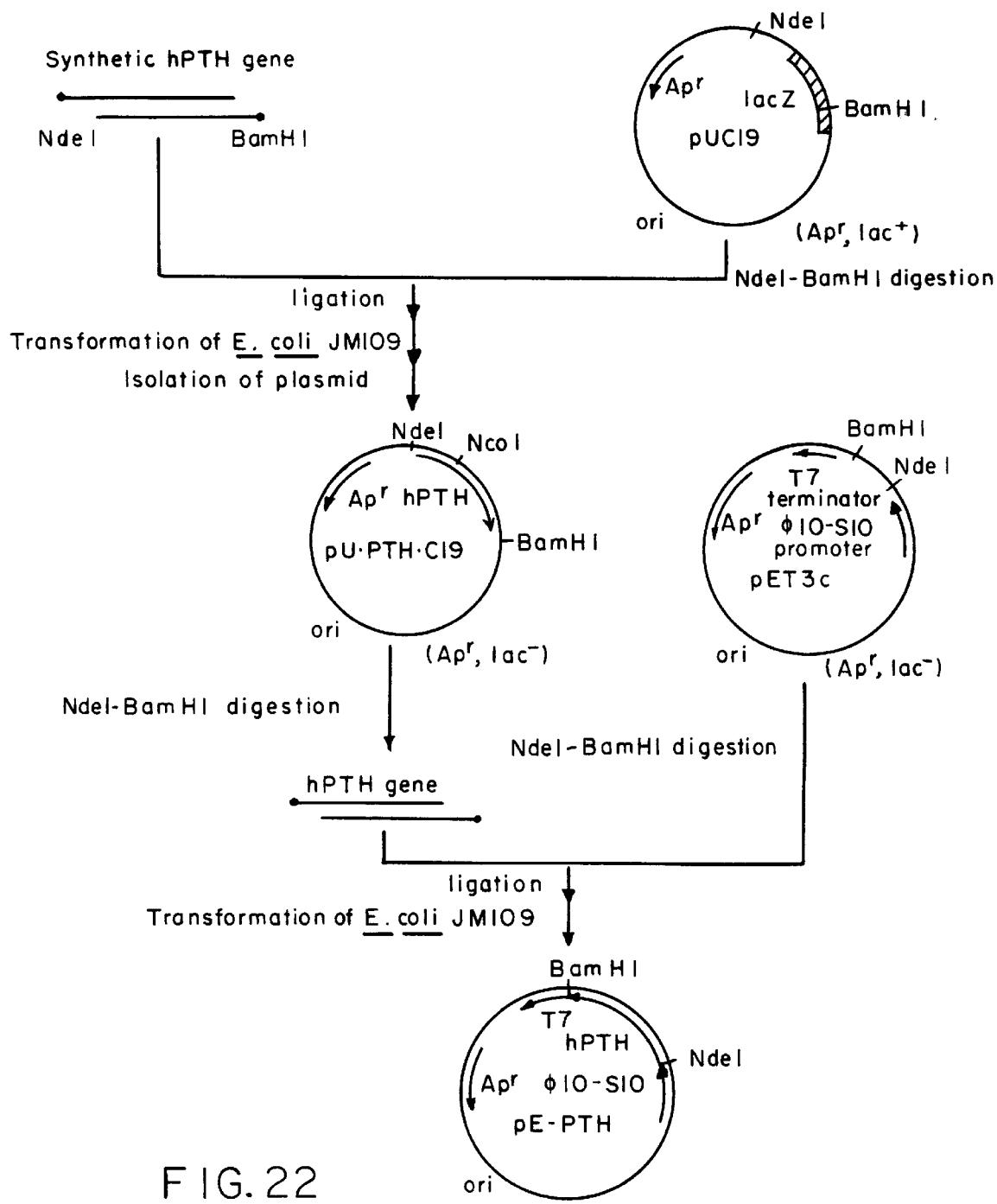
FIG. 22 shows the construction scheme for the plasmid pE-PTH obtained in Example 7.

(d) Cloning of hPTH Gene (FIG. 22)

(d-1) As a cloning vector, *E. coli* plasmid pBR322-derived pUC19 [J. Messing, *Gene* 33, 103–109 (1985)] was used. pUC19 DNA was rected in 20 μl of a reaction solution [20 mM Tris-HCl (pH 7.6), 7 mM MgCl$_2$, 150 mM NaCl, 10 mM 2-mercaptoethanol, 20 units of NdeI (New England Biolabs), 15 units of BamHI (Takara Shuzo)] at 37° C. for 24 hours. Then, the resulting product was diluted 5 times with water, and treated at 65° C. for 20 minutes to inactivate the enzyme. 5 μl of this reaction solution was mixed with about 5 equivalents of the DNA fragments obtained in the above item c-1 to prepare 20 μl of a reaction solution containing 50 mM Tris-HCl (pH 7.5), 10 mM MgCl$_2$, 10 mM DIT, 1 mM spermidine, 0.1 mg/ml BSA and 1 mM ATP. Then, T4 DNA ligase (New England Biolabs) was reacted with this solution at 14° C. for 15 hours to ligate the hPTH gene to the plasmic.

Using this reaction solution, the E. coli JM109 strain [J. Messing, Gene 33, 103–119 (1985)] was transformed according to methods known in the art. Namely, 50 μl of competent cells [D. Hanahan, J. Mol. Biol. 166, 557 (1983)] stored at -70° C. was incubated at 0° C. for 15 minutes, and then 10 μl of the above-mentioned reaction solution was added thereto. The resulting solution was further incubated at OC for 15 minutes, and then incubated at 42° C. for 1.5 minutes and further at 0° C. for 2 minutes. To this reaction solution was added 200 μl of LB medium (containing 10 g of Bacto-tryptone, 5 g of a Bacto-yeast extract and 5 g of NaCl), and incubated at 37° C. for 1 hour. This E. coli was seeded onto LB agar medium containing 50 μg/ml ampicillin, 100 μg/ml X-Gal and 0.1 mM isopropyl-β-D-thiogalactopyranoside (IPTG), and incubated at 37° C. overnight. Of the resulting ampicillin-resistant colonies, 14 β-galactosidase-deficient strains were selected and plasmid DNAs of transformed strains thereof were crudely purified by the alkali method [T. Maniatis et al., *Molecular Cloning*, (Cold Spring Harbor Laboratory) 368–369 (1982)], followed by digestion with NcoI and BamHI, and further with NdeI and BamHI. The electrophoretic patterns of these digests on a 1.7% agarose gel revealed that one strain was a transformed strain into which the hPTH gene was correctly inserted.

(d-2) The hPTH gene was also cloned by the following method. As a cloning vector, pUC19 (Takara Shuzo) was used. 0.5 μg of pUC19 DNA was reacted in 10 μl of a reaction solution [50 mM Tris-HCl (pH 7.5), 10 mM MgCl$_2$, 100 mM NaCl, 1 mM dithiothreitol, 20 units of NdeI (New England Biolabs), 10 units of BamHI (Takara Shuzo)] at 37° C. for 5 hours. Then, the resulting product was treated at 65° C. for 15 minutes to inactivate the enzyme. 1 μl of this reaction solution was mixed with about 10 equivalents of the DNA fragment obtained in the above item c-2, and the hPTH gene was ligated to the plasmid using a DNA ligation kit (Takara Shuzo). The transformation of the E. coli JM109 strain was carried out in the same manner as in step (d-1). Of the resulting ampicillin-resistant colonies, 17 β-galactosidase-deficient strains were selected and plasmid DNAs of transformed strains thereof were crudely purified by the alkali method, followed by digestion with NcoI and BamHI, and further with NdeI and BamHI. The electrophoretic patterns of these digests on a 1.5% agarose gel revealed that three strains were transformed strains into which the hPTH gene was correctly inserted.

The cloning vectors obtained in the above items d-1 and d-2 were named pU·PTH·C19. 20 ml of LB medium containing 50 μg/ml ampicillin was inoculated with one loopful of E. coli JM109 recombinants having plasmid pU·PTH·C19 and cultivated at 37° C. overnight with shaking. Plasmid DNA was crudely purified from this culture solution, and dissolved in 80 μl of TE buffer [10 mM Tris-HCl (pH 8.0), 1 mM EDTA] containing 20 μg/ml RNase.

(e) Construction of Plasmid for Expression of hPTH and Production of Transformant (FIG. 22)

About 10 μg of pU·PTH·C19 obtained in step (d) was reacted in a reaction solution [150 mM NaCl, 20 mM Tris-HCl (pH 7.8), 7 mM MgCl$_2$, 10 mM mercaptoethanol, 40 nunits of NdeI, 20 units of BamHI (Takara Shuzo)] at 37° C. for 5 hours. Then, 263-bp DNA fragments were purified by 1.7% agarose gel electrophoresis according to known methods. As a vector for expression, pET3C [F. W. Stadier et al., *Methods in Enzymology* 195, 60–89 (1990)] was used. pET3C DNA was digested with NdeI and BamHI in the same manner as above, and four times as much water as the resulting reaction solution was added thereto, followed by heating at 65° C. for 20 minutes to inactivate the enzymes.

Each of the 263-bp DNA and the plasmid DNA has single stranded cohesive ends produced by NdeI digestion and BamHI digestion at both ends thereof.

Both of them were mixed with each other, and the mixture was reacted with T4 DNA ligase (New England Biolabs) in the presence of 50 mM Tris-HCl (pH 7.6), 10 mM MgCl$_2$, 10 mM DTT, 1 mM spermidine, 0.1 mg/ml BSA and 1 mM ATP at 14° C. for 16 hours to ligate the DNAs to each other, followed bytransformation of the E. coli JM109 strain in the same manner as above. Then, this E. coli was seeded onto LB agar medium containing 50 μg/ml ampicillin, and cultivated at 37° C. for 1 day. The resulting ampicillin-resistant colonies were selected. Plasmid DNAs of the transformed strains were further digested by combinations of restriction enzymes such as NdeI-BamHI, BglII-BamHI, EcoRI-NdeI and AvrII-BglII. Transformed strains containing the correct hPTH genes were selected by their patterns of polyacrylamide electrophoresis. The plasmids for expression thus obtained were named pE-PTH.

(II) Production of [Cys$^{35}$] human PTH (1-84):

(i) Construction of pU-PTH, a plasmid containing a human PTH gene, for site-directed mutagenesis, The plasmid pE-PTH obtained in (I) above, which incorporates human PTH DNA, was digested with BamH I and Xba I to yield a 0.3 kbp DNA fragment containing the human PTH DNA and pET3c expression promoter. Next, pUC118, a plasmid vector for preparation of single-stranded chains, was digested with BamH I and Xba I and mixed with the above-mentioned DNA fragment containing the human PTH gene, and they were ligated using T4 DNA ligase. The ligated DNA was used to transform *Escherichia coli* MV1184. Cells of the resulting transformant were sown over a plate with from correct insertion of the human PTH gene in pUC118, to be released in the form of phage particles into the culture medium. This single-stranded DNA was purified and used as a template for site-directed mutagenesis. The *Escherichia coli* MV1184 and helper phage KO7 used herein are described by J. Vieira and J. Messing in Methods in Enzymology, 153, 3–11 (1987).

(ii) Production and expression of a gene which codes for [Cys$^{35}$] human PTH(1-84)

Figure 23:
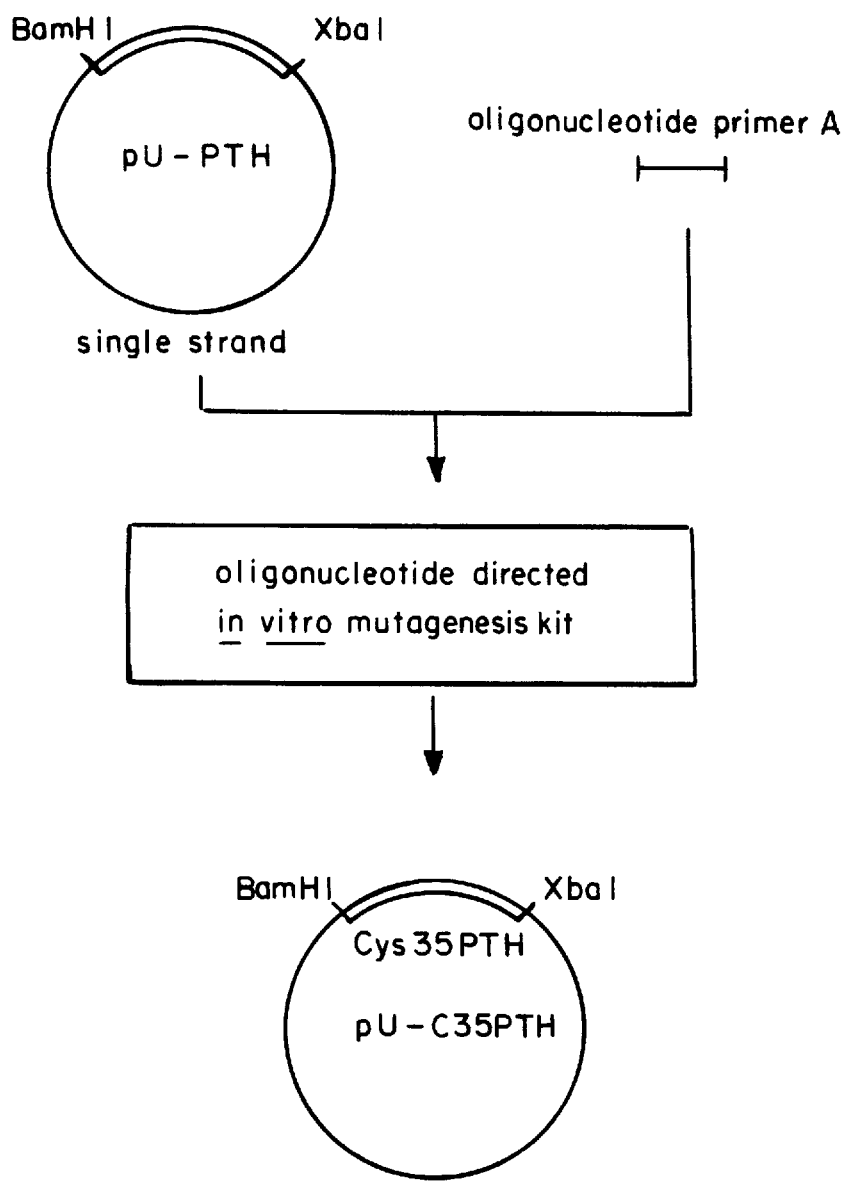
FIG. 23 shows the process for site-directed mutagenesis to produce the plasmid pU-C35PTH obtained in Example 7.

(a) Production of a gene which codes for [Cys$^{35}$] human PTH(1-84) (see FIG. 23)

First, to convert the 35-Val codon to a Cys codon, an oligonucleotide primer A:CACAATTTTTGCGCCTTAG-GTGC (SEQ ID NO:33) was synthesized. Using a site-directed mutagenesis kit (Amersham Corporation, Oligonucleotide Directed In Vivo Mutagenesis System, Version 2), a mutated plasmid was obtained from a combination of the above synthetic oligonucleotide (4 picomol) with its 5' terminal phosphorylated by T4 kinase treatment and the above-mentioned single-stranded pU-PTH (5 μg). This plasmid was used to transform *Escherichia coli* MV1184 by a conventional method. Cells of the resulting transformant were sown over a 2×YT medium agar plate containing 150 μg/ml ampicillin and cultivated at 37° C. for 15 hours to yield a large number of colonies. From 10 of the colonies was collected a small amount of bacterial cells, which then were cultivated in 0.3 ml of 2×YT medium for about 5 hours. A 30 μl portion of this culture broth and 30 pl of a solution containing helper phage KO7 were mixed and kept standing at 37° C. for 1 hour, followed by overnight cultivation in the presence of 3 ml of 2×YT medium. The culture broth was centrifuged to separate the supernatant and cells. From the cells the plasmid was crudely purified by the alkali method, and the single-stranded DNA was recovered from the supernatant as a phage particle by a conventional method.

The oligonucleotide primer A described above contains a restriction enzyme Hha I recognition site, which is not present in the template gene which codes for human PTH.

Consequently, reacting Hha I on the correctly mutated plasmid should cause cleavage at two sites, namely the Hha I site newly resulting from mutation and the Hha I site originally present in pUC118, to yield a 260 bp fragment. The plasmid obtained from the 10 colonies described above was digested with Hha I and analyzed by agarose gel electrophoresis and a correct-sized fragment was seen in four clones.

With the single-stranded plasmids from two clones used as template, DNA sequencing was conducted using DNA sequencer model 373A (Applied Biosystems Inc.); it was confirmed that the desired mutation was introduced (FIG. 25).

The plasmid thus obtained, which contains the gene coding for [$Cys^{35}$] human PTH (FIG. 25), is called pU-C35PTH.

Figure 24:
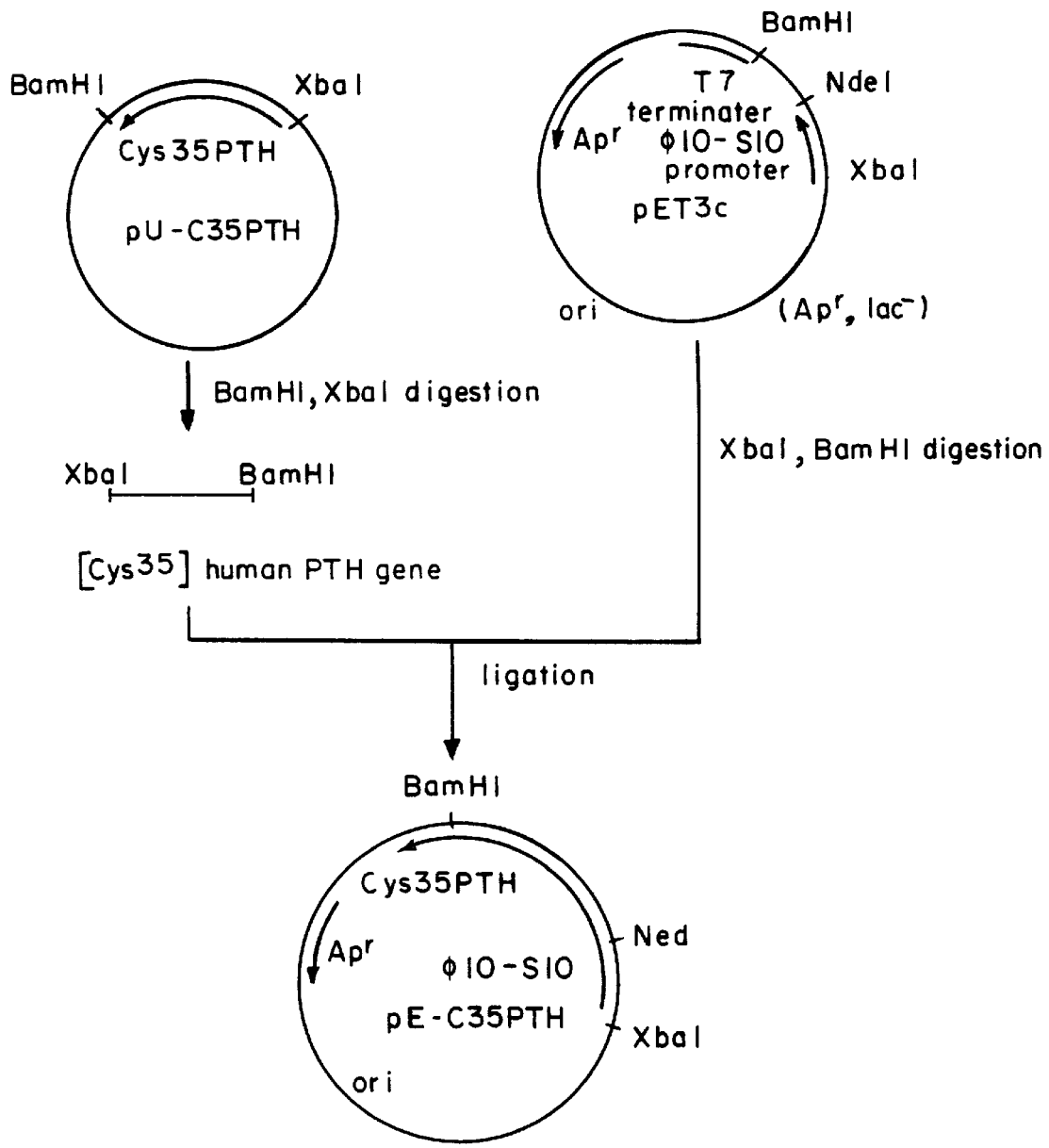
FIG. 24 shows the construction scheme for the plasmid pE-C35PTH obtained in Example7.

(b) Construction of pE-C35PTH, an *Escherichia coli* expression plasmid (see FIG. 24) pU-C35PTH as obtained in step (a) was digested with restriction enzymes Xba I and BamH I to yield an about 0.3 kbp fragment which codes for the mutein [$Cys^{35}$] human PTH. After purification by agarose gel electrophoresis, this fragment was ligated to the expression plasmid vector pET3c [F. W. Stadier et al.; Methods in Enzymology, 195, 60–89 (1990)], previously digested with restriction enzymes Xba I and BamH I, using T4 ligase. The expression plasmid thus obtained is called pE-C35PTH.

The λ phage DE3 [F. W. Stadier et al.; Journal of Molecular Biology, 189, 113–130 (1986)], incorporating a T7 phage RNA polymerase gene, was lysogenized to *Escherichia coli* MM294 strain to yield the *Escherichia coli* MM294(DE3) strain.

The plasmid pE-C35PTH was used to transform *Escherichia coli* MM294(DE3) to yield cells of MM294(DE3)/pE-C35PTH, a strain having a plasmid containing the mutein-encoding gene shown in FIG. 25.

Figure 26:
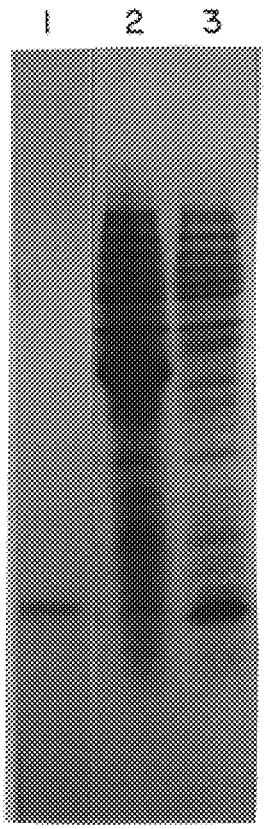
FIG. 26 shows sodium dodecyl sulfate-polyacrylamine gel electrophoresis (stained by Coomassie Brilliant Blue) indicating the production of [Cys35] human PTH in Example 7 in which, lane 1 shows standard sample of human PTH, lane 2 shows an extract of the transformant bearing the plasmid without [Cys$^{35}$] human PTH gene, and lane 3 shows an extract of the transformant bearing the plasmid pE-C35PTH after induction by IPTG.
Figure 27:
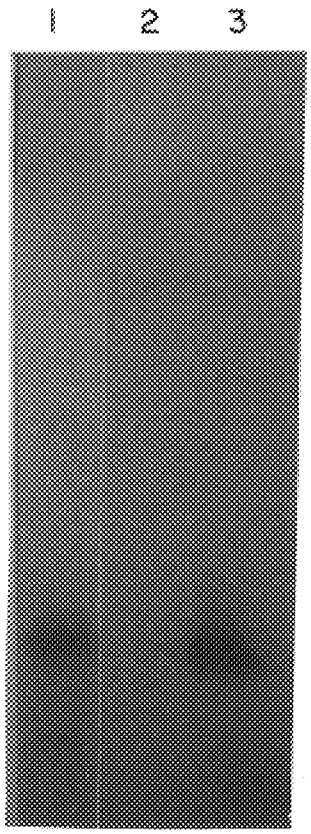
FIG. 27 shows the result of Western blotting of FIG. 26.

(c) Production of [$Cys^{35}$] human PTH i) *Escherichia coli* MM294(DE3)/pE-C35PTH was subjected to 20 shaking culture in 3 ml of an LB medium containing 60 μg/ml ampicillin at 37° C. overnight. A 100 μl portion of this culture broth was added to 10 ml of the same medium dispensed in a 200 ml flask and cultivated at 37° C. until the Klett value reached about 170, after which isopropyl-β-D-thiogalacto-pyranoside (IPTG) was added to reach a final concentration of 0.1 mM. After 2 more hours of cultivation, 1 ml of the culture broth was centrifuged at 15000 rpm and 4° C. for 5 minutes. The cells thus separated were dissolved in 100 μl of an aqueous solution containing 0.5M Tris-HCl (pH 6,8), 10% glycerol, 10% (W/V) sodium dodecyl sulfate (SDS), 0.1% (W/V) β-mercaptoethanol and Bromophenol Blue [Laemmli, U. K.; Nature, 227, 680 (1970)] and boiled for 3 minutes, followed by 16% SDS polyacrylamide gel electrophoresis (PAGE). After electrophoresis, the gel was stained with Coomassie Brilliant Blue; a dense band having the same mobility as the reference sample of human PTH appeared (see FIG. 26). The lanes in FIG. 26 respectively show the result from human PTH (1 μg) for lane 1, the result from a culture broth (10 μl) of an *Escherichia coli* strain carrying no plasmid pE-C35PTH after adding IPTG for lane 2, and the result from a culture broth (10 μl) of an *Escherichia coli* strain carrying the plasmid pE-C35PTH after adding IPTG for lane 3. Another gel was subjected to Western blotting using the human PTH antibody; the same stain pattern as with the reference sample of human PTH was obtained (see FIG. 27). The lanes in FIG. 27 are similar to those shown in FIG. 26. Quantitative comparisons of gel stain pattern with the standard sample revealed that about 200 mg of [$Cys^{35}$] human PTH was expressed per liter of culture broth.

ii) The [$Cys^{35}$] human PTH accumulated in *Escherichia coli* was purified as follows. Cells from 200 ml of a culture broth obtained in the same manner as above were suspended in a buffer (5 ml) containing 8M urea, 50 mM Tris-HCl (pH 7.5), 50 mM EDTA, 20 mM 2-mercaptoethanol (hereinafter abbreviated 2-ME) and 1 mM α-toluenesulfonyl fluoride, and this suspension was vigorously shaken under ice cooling conditions for about 1 hour to disrupt the cells. After centrifugation at 15000 rpm and 4° C. for 20 minutes, the resulting supernatant was collected, and the precipitate was subjected to two cycles of the same extraction procedure using buffers (3 ml for each cycle) with the same composition. The supernatants were combined and double diluted. This dilution was passed through a column of TSK-gel CM-Toyopearl (Tosoh Corporation) (10 ml) equilibrated with a 50 mM ammonium acetate buffer (pH 5) containing 4M urea and 10 mM 2-ME to adsorb the desired substance. The column was washed with a 50 mM ammonium acetate buffer (pH 5) containing 4M urea and 10 mM 2-ME (about 10 ml buffer was required). After the absorption at 280 nm disappeared, the column was developed by the linear gradient method using a combination of 50 ml of a 50 mM ammonium acetate buffer (pH 5) containing 10 mM 2-ME and 50 ml of a 0.5M ammonium acetate buffer (pH 6) (flow rate 10 ml/hr, volume 2 ml for each fraction). Fraction Nos. 35 through 43 were combined, lyophilized and then subjected to reverse phase high performance liquid chromatography under the following conditions. Column, YMC-pack A-325 S-5120A ODS (1×30 cm) (produced by Y.M.C.); solvent, acetonitrile containing 0.1% trifluoroacetic acid on a linear density gradient from 25% to 50%; flow rate, 3 ml/minutes. The peak of the desired substance (retention time 17.0 minutes) was separated. The eluate thus obtained was passed through a column of Bio-Rad AG 1×8 (acetate form) (Bio-Rad Laboratory). After column washing, the washings were combined and the acetonitrile was distilled off, followed by lyophilization. The desired hPTH was obtained as a white powder with a yield of 3.6 mg.

Figure 29:
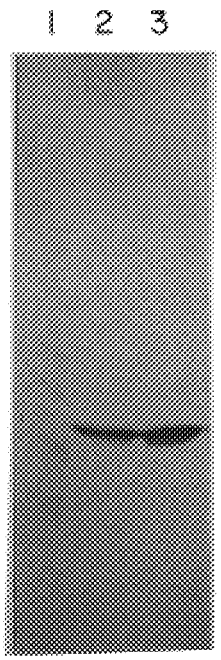
FIG. 29 shows the results of SDS-PAGE, in which lane 1 shows molecular weight marker, lane 2 shows standard human PTH, and lane 3 shows purified [Cys$^{35}$] human PTH obtained in Example 7.
Figure 28:
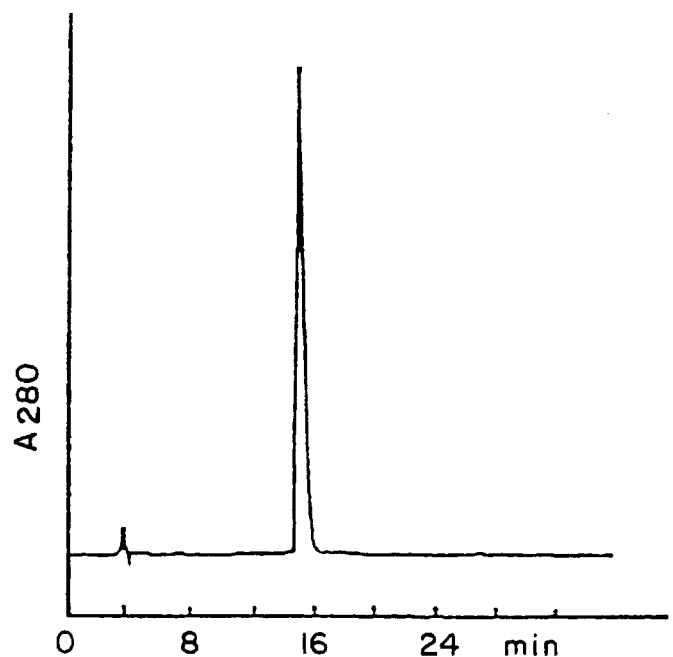
FIG. 28 shows the results of reverse phase HPLC obtained in Example 7.

This sample was identified as highly purified [$Cys^{35}$] human PTH, as confirmed by the analyses described below.

a) A single sharp peak appeared in reverse phase HPLC (see FIG. 28). Column, YMC-pack A-303 S-5 ODS 120A, 4.6 dia.×260 mm; eluents, A (0.1% trifluoroacetic acid) and B (acetonitrile containing 0.1% trifluoroacetic acid); gradient program, 0–30 minutes (30–38%, B); flow rate, 1 ml/minute. b) A single band with the same mobility as with human PTH appeared in SDS-PAGE (see FIG. 29). The lanes in FIG. 29 respectively show the result from the molecular marker for lane 1, the result from human PTH for lane 2, and the result from [Cys$^{35}$] human PTH for lane 3.

c) The results of amino acid analyses are as follows (in the presence of thioglycolic acid, in a reduced pressure sealed tube, 110° C., 24 hours, 5.7N hydrochloric acid hydrolysis, figures in parentheses are theoretical values).

Asp (10), 10.33; Thr (1), 0.91; Ser (7), 6.10; Glu (11), 11.82; Pro (3), 3.00; Gly (4), 4.44; Ala (7), 6.91; Cys (1), 1.11; Val (7), 6.60; Met (2), 2.11; Ile (1.01; Leu (10), 10.83, Phe (1), 1.10; Lys (9), 9.32; His (4), 3.75; Arg (5), 5.2 Trp (1), 0.93 (recovery 84.2%; the value for Cys was obtained from the hydrolyzate after oxidation with performic acid.)

d) N-terminal amino acid sequencing using the gas-phase sequencer model 470 A (Applied Biosystems Inc.) revealed that the sequence from the 1-Ser to the 15-Leu is correct.

A mutein having the amino acid sequence shown in FIG. 25, in which the 35-valine has been replaced by cysteine, was thus obtained.

(III) Production of hPTH(1-34)OH from [Cys$^{35}$]hPTH(1-84)

S-cyanylation of the Cys$^{35}$ of [Cys$^{35}$]hPTH(1-84) was achieved in accordance with the method described in Example 5(5) as follows. 4.76 mg of [Cys$^{35}$]hPTH(1-84) was dissolved in 2.4 ml of 6M Gu-HCl-0.2M Tris-acetic acid (pH 8.4). To this solution was added 0.154 mg of dithiothreitol in solution in 0.1 ml of the same buffer, and the mixture was kept standing at room temperature for 30 minutes. Then, 1.646 mg of 2-nitro-5-thiolyonebenzoic acid (NTCB) in solution in 0.1 ml of the same buffer was added, and the pH was immediately adjusted to 8.0, followed by reaction at room temperature for 15 minutes. After completion of the reaction, 2.5 ml of acetic acid was added, followed by desalting by gel filtration using a Sephadex G-25 column. The gel filtration conditions used were column size, 2.6×37 cm; detection wavelength, 280 nm; eluent, 10% acetic acid; flow rate, 20 ml/hr. The fraction containing [SCN-Cys$^{35}$]hPTH(1-84) was collected and lyophilized, after which it was used for cleavage reaction.

Figure 30:
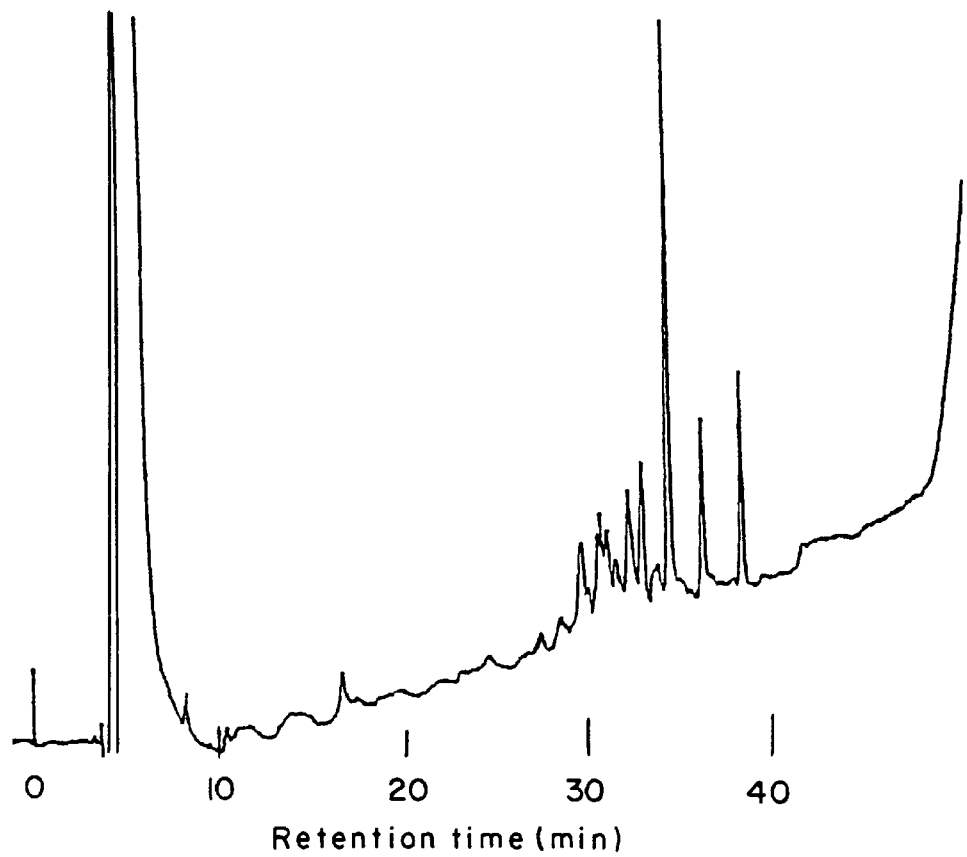
FIG. 30 shows the results of reverse phase high performance liquid chromatography obtained in Example 7.

The cleavage reaction for the obtainment of hPTH(1-34) OH was performed as follows. 200 μg of [SCN-Cys$^{35}$]hPTH (1-84) was reacted in 200 μl of a 6M Gu-HCl-0.1M borate buffer at 37° C. for 17 hours, and the reaction was terminated by the addition of the same amount of glacial acetic acid. The reaction broth thus obtained was assayed by reverse phase high performance liquid chromatography (FIG. 30). The assay conditions were) column, YMC A-303 ODS (4.6×250 mm; column temperature, 25° C.; solvent, 0.1% trifluoroacetic acid-99.9% distilled water (Eluent A). and 0.1% trifluoroacetic acid-99.9% acetonitrile (Eluent B); elution program, 0 minute (75% A+25% B), 40 minutes (60% A+40% B), 45 minutes (20% A+80% B); elution rate, 0.7 ml/min; detection wavelength, 230 nm. The retention time of the peak indicated by the arrow in the figure, about 35 minutes, agreed with the elution time of the reference sample of hPTH(1-34)OH purchased from Peptide Instifute, Inc., (Japan). This peak fraction was separated and subjected to various protein chemical analyses. Under the elution conditions used in reverse phase high performance liquid chromatography, the C-terminal fragment of the cleavage products was eluted in the flow through fraction.

The amino acid composition of hPTH(1-34)OH was analyzed in accordance with the method described above. The data obtained are shown in Table 6, agreeing with the theoretical values for hPTH(1-34)OH. Moreover, the carboxyl terminal amino acid Phe$^{34}$ of the obtained product hPTH(1-34)OH was confirmed not to have been racemized as follows.

The sample used was the hydrolyzate used for the amino acid analysis. All amino acids in the hydrolyzate were pre-labeled with ortho-phthalaldehyde. Assay was made by reverse phase high performance liquid chromatography using a YMC A-303 ODS column (4.6×250 mm). The eluent used was 50 mM sodium acetate-40% methanol. As a result, Phe in the hydrolyzate was detected as L-Phe, while no peak of D-Phe was detected. The molecular weight of the hPTH (1-34)OH obtained was determined by fast atom bombardment mass spectrometry (FAB-MS) to be mass (m/z):(M+ H)$^+$=4116.8, whose difference from the theoretical value 4118.1 was within the range of error.

TABLE 6

Amino Acid Composition of the hPTH(1–34)OH Obtained

| | Experimentally Obtained Value | Theoretical Value |
|---|---|---|
| Asp & Asn | 4.00 | 4 |
| Ser | 2.59 | 3 |
| Gln & Gln | 5.01 | 5 |
| Gly | 1.14 | 1 |
| Val | 2.84 | 3 |
| Met | 1.94 | 2 |
| Ile | 0.85 | 1 |
| Len | 4.84 | 5 |
| Phe | 0.87 | 1 |
| Lys | 2.94 | 3 |
| His | 2.58 | 3 |
| Trp | 0.65 | 1 |
| Arg | 1.79 | 2 |

Example 8

Production of hPTH(1-34)-NH$_2$ from [Cys$^{35}$]hPTH(1-84)

S-cyanaylation of the Cys$^{35}$ of [Cys$^{35}$]hPTH(1-84) was achieved in accordance with the method described by Wakselman et al.in the Journal of Chemical Society Chemical Communication, 1967, 21–22, as follows. 8.40 mg of [Cys$^{35}$]hPTH(1-84) was dissolved in 3.78 ml of 7M urea-0.1M ammonium acetate (pH 3.5). After keeping this solution standing at 25° C. for 15 minutes, 592 μg of 1-cyano-4-dimethylaminopyridinium fluoroborate dissolved in 0.42 ml of the same buffer was added, followed by reaction at room temperature for 15 minutes. After completion of the reaction, the reaction mixture was immediately desalted using a Sephadex G-25 column. The conditions for gel filtration were column size, 2.6×37 cm; eluent, 10% acetic acid; flow rate, 20 ml/hr; detection wavelength, 280 nm. The fraction containing [SCN-Cys$^{35}$]hPTH(1-84) was collected and lyophilized. The yield was 7.5 mg. This product was used for cleavage reaction as follows.

Figure 31:
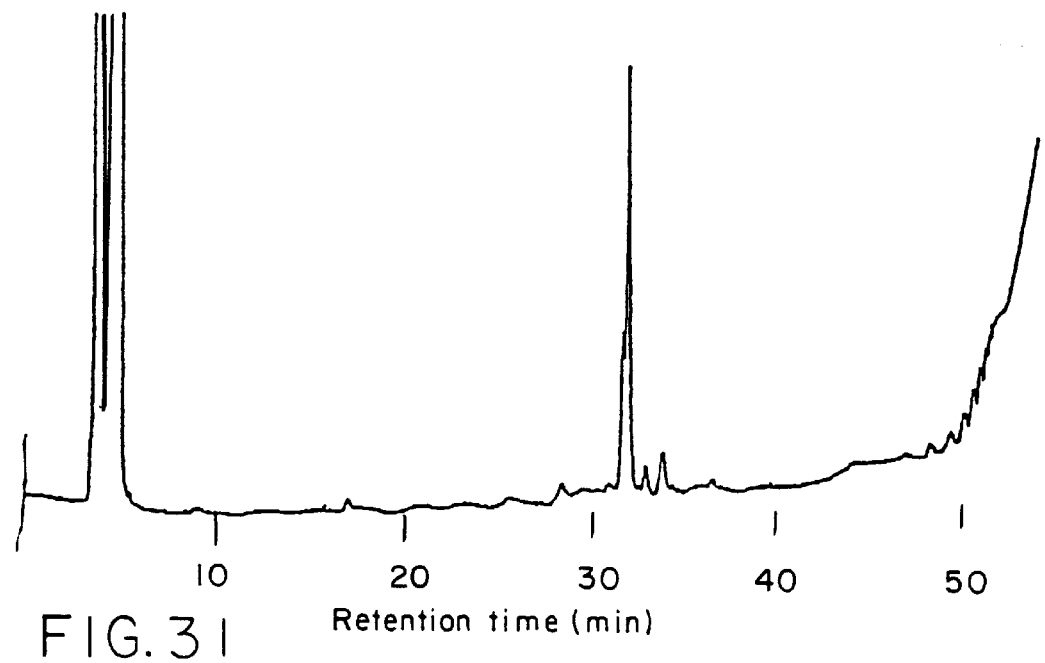
FIG. 31 shows the results of reverse phase high performance liquid chromatography obtained in Example 8.

200 μg of [SCN-Cys$^{35}$]hPTH(1-84) was dissolved in 200 pl of 3M aqueous ammonia, followed by reaction at 37° C. for 10 minutes. The reaction mixture was assayed by reverse phase high performance liquid chromatography under the conditions described in Example 7. As seen in FIG. 31, the [SCN-Cys$^{35}$]hPTH(1-84) disappeared completely, while a single peak with a shoulder appeared at a retention time of 32 minutes. The main peak portion of this peak agreed with the elution position of the reference sample of hPTH(1-34) -NH$_2$ prepared by solid phase peptide synthesis. Under the assay conditions used, the C-terminal fragment of the cleavage products was eluted in the flow through fraction.

Example 9
Production of hPTH(1-34)NHC$_2$H$_5$ from [Cys$^{35}$]hPTH(1-84)

S-cyanylation of the cystein residue of [Cys$^{35}$]hPTH(1-84) and separation of [SCN-Cys$^{35}$]hPTH(1-84) were achieved as directed in Example 8.

Figure 32:
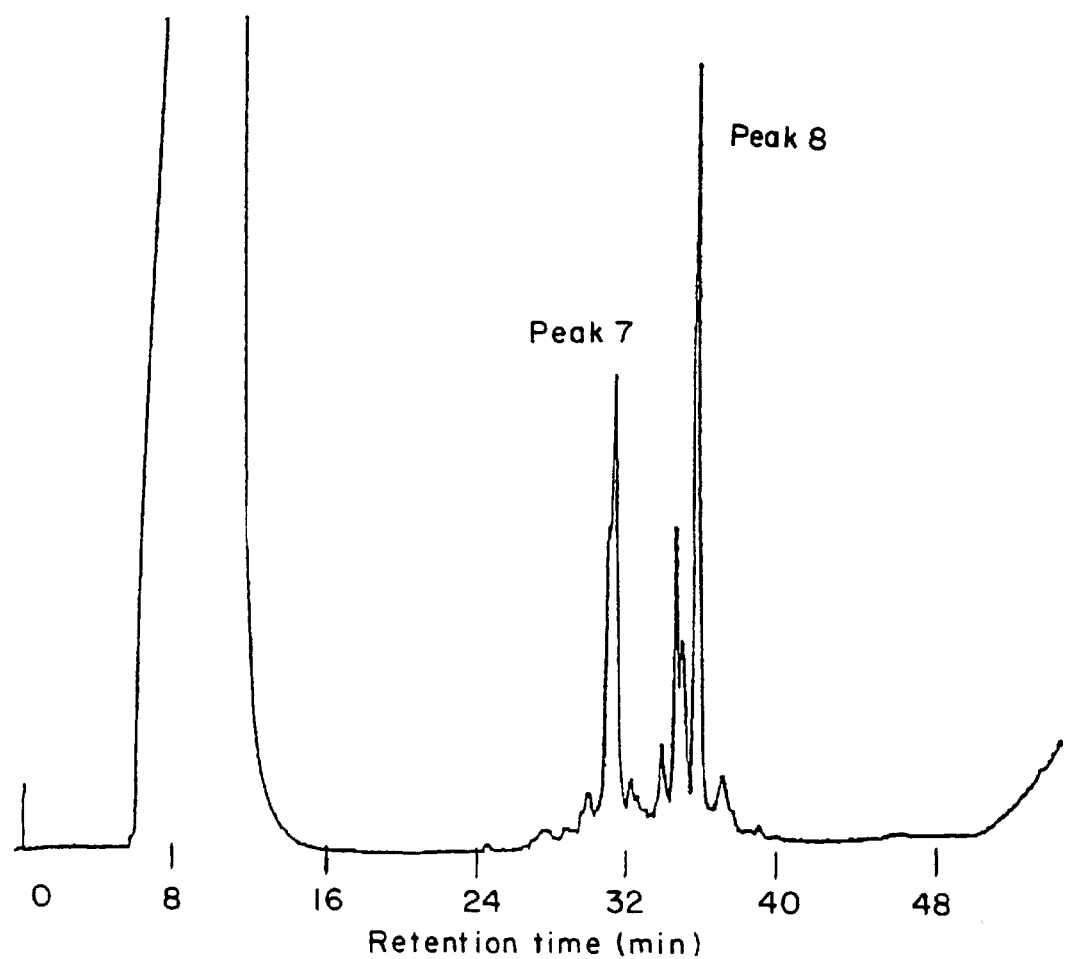
FIG. 32 shows the results of reverse phase high performance liquid chromatography obtained in Example 9.

200μg of [SCN-Cys$^{35}$]hPTH(1-84) was dissolved in 500 μl of 3.1M ethylamine, followed by reaction at 37° C. for 20 minutes. Then, the same amount of glacial acetic acid was added to terminate the reaction. The reaction mixture thus obtained was assayed by reverse phase high performance liquid chromatography under the same conditions as in Example 7. As seen in FIG. 32, the [SCN-Cys$^{35}$]hPTH(1-84) disappeared almost completely, while two major peaks appeared. These peaks, eluted at retention times of 31 minutes and 36 minutes, respectively, were designated as Peak 7 and Peak 8, respectively, and separated and subjected to protein chemical analyses.

The amino acid composition of the fraction of Peak 8 was determined as directed in Example 7. The data obtained are shown in Table 7. These values agreed well with the theoretical values of hPTH(1-34)NHC$_2$H$_5$. To determine whether the carboxyl terminal amino acid Phe$^{34}$ of Peak 8 was racemized or not, the hydrolysate used for amino acid analysis was analyzed. After pre-labeling all amino acids with ortho-phthalaldehyde, analysis was made by reverse phase high performance liquid chromatography using a YMC A-303 ODS column (4.6×250 mm). The eluent used was 50 mM sodium acetate-40% methanol. As a result, all Phe in the hydrolysate was detected as L-Phe, while no peak of D-Phe was detected. The molecular weight of the hPTH (1-34)NH$_2$C$_2$H$_5$ obtained was determined by FAB-MS to be mass (m/z):(M+H)$^+$=4144.9, whose difference from the theoretical value 4143.2 was within the range of error.

The fraction of Peak 7 was also subjected to amino acid analysis. The values almost agreed with the theoretical composition of [SCN-Cys$^{35}$]hPTH(1-84). Judging from the fact that the starting material [SCN-Cys$^{35}$]hPTH(1-84) is eluted at a retention time of about 35 minutes, Peak 7 may be assigned to [dehydroalanine$^{35}$]hPTH(1-84) as resulting from β-elimination of the S-cyano group of [SCN-Cys$^{35}$] hPTH(1-84). The β-elimination reaction has been reported to compete with cleavage reaction [Y. Degami, A. Patchornik et al.; Biochemistry, 13, 1–11 (1974)].

The C-terminal fragment of the cleavage products was eluted in the flow though fraction.

TABLE 7

Amino Acid Composition of the hPTH(1-34)NHC$_2$H$_5$ Obtained

|  | Experimentally Determined Value | Theoretical Value |
|---|---|---|
| Asp & Asn | 4.01 | 4 |
| Ser | 2.74 | 3 |
| Glu & Gln | 5.22 | 5 |
| Gly | 1.35 | 1 |
| Val | 2.74 | 3 |
| Met | 2.09 | 2 |
| Ile | 0.91 | 1 |
| Leu | 4.86 | 5 |
| Phe | 1.00 | 1 |
| Lys | 2.89 | 3 |
| His | 2.58 | 3 |
| Trp | 0.75 | 1 |
| Arg | 1.43 | 2 |
| Ethylamine | 1.58 | 1 |

Example 10
(1) Synthesis of H-Pro-Tyr-Gly-Cys-Gly-Glu-Glu-Asn-Leu-Val-Tyr-NH$_2$ (Peptide A) (SEQ ID NO:35)

H-Pro-Tyr-Gly-Cys-Gly-Glu-Glu-Asn-Leu-Val-Tyr-NH$_2$ (Peptide A) (SEQ ID NO:35) was synthesized by the solid phase method in accordance with the method of Merrifleld, R. B. [Advance of Enzymology, 32, 221–296 (1969)] using automatic peptide synthesizer 430A (Applied Biosystems). The carrier used was p-methyl-BHA-resin. Synthesis was sequentially performed from the carboxyl terminal. The Boc-amino acids used were Boc-Pro, Boc-Tyr(Br-Z), Boc-Gly, Boc-Cys(4-CH$_3$BZl), Boc-Glu(OBZl), Boc-Asn, Boc-Leu and Boc-Val. After synthesis to the amino terminal Pro, the peptide resin was taken out from the synthesizer.

To 450 mg of the peptide resin were added 0.45 ml of p-cresol, 0.45 ml of ethanedithiol, 50 mg of 2-mercaptopyridine and also about 3.5 ml of liquid hydrogen fluoride, followed by reaction at 0° C. for 1.5 hours. After completion of the reaction, the hydrogen fluoride was evaporated under reduced pressure, and most of the remaining reagents were washed out with diethyl ether containing 0.1% 2-mercaptoethanol. The peptide was extracted with 10 ml of 3% acetic acid and centrifuged. After removal of resin, the supernatant was purified by gel filtration using a Sephadex G-25 column. The gel filtration conditions were column size, 2.8×60 cm; detection wavelength, 280 nm; eluent, 3% acetic acid; and flow rate, 30 ml/hr. The fraction containing the peptide was collected and purified by reverse phase high performance liquid chromatography. The assay conditions were column, YMC A-303 ODS (4.6×250 mm); column temperature, 25° C.; eluent, 0.1% trifluoroacetic acid-99.9% distilled water (Eluent A) and 0.1% trifluoroacetic acid-99.9% acetonitrile (Eluent B); elution program, 0 minute (95% A+5% B), 30 minutes (55% A+45% B), 35 minutes (20% A+80% B); flow rate, 0.7 ml/min; detection wavelength, 280 nm. The main peak, eluted at a retention time of about 27 minutes was collected and lyophilized. Amino acid analysis Asp (1), 1.03; Glu (2), 2.15; Gly (2), 1.89; Val (1), 0.89, Leu (1), 1.00, Tyr (2),1.96; Pro (1), 1.00

(2) Synthesis of H-Pro-Tyr-Gly-OH (SEQ ID NO:36) from H-Pro-Tyr-Gly-Cys-Gly-Glu-Glu-Asn-Leu-Val-Tyr-NH$_2$ (SEQ ID NO:35)

Figure 33:
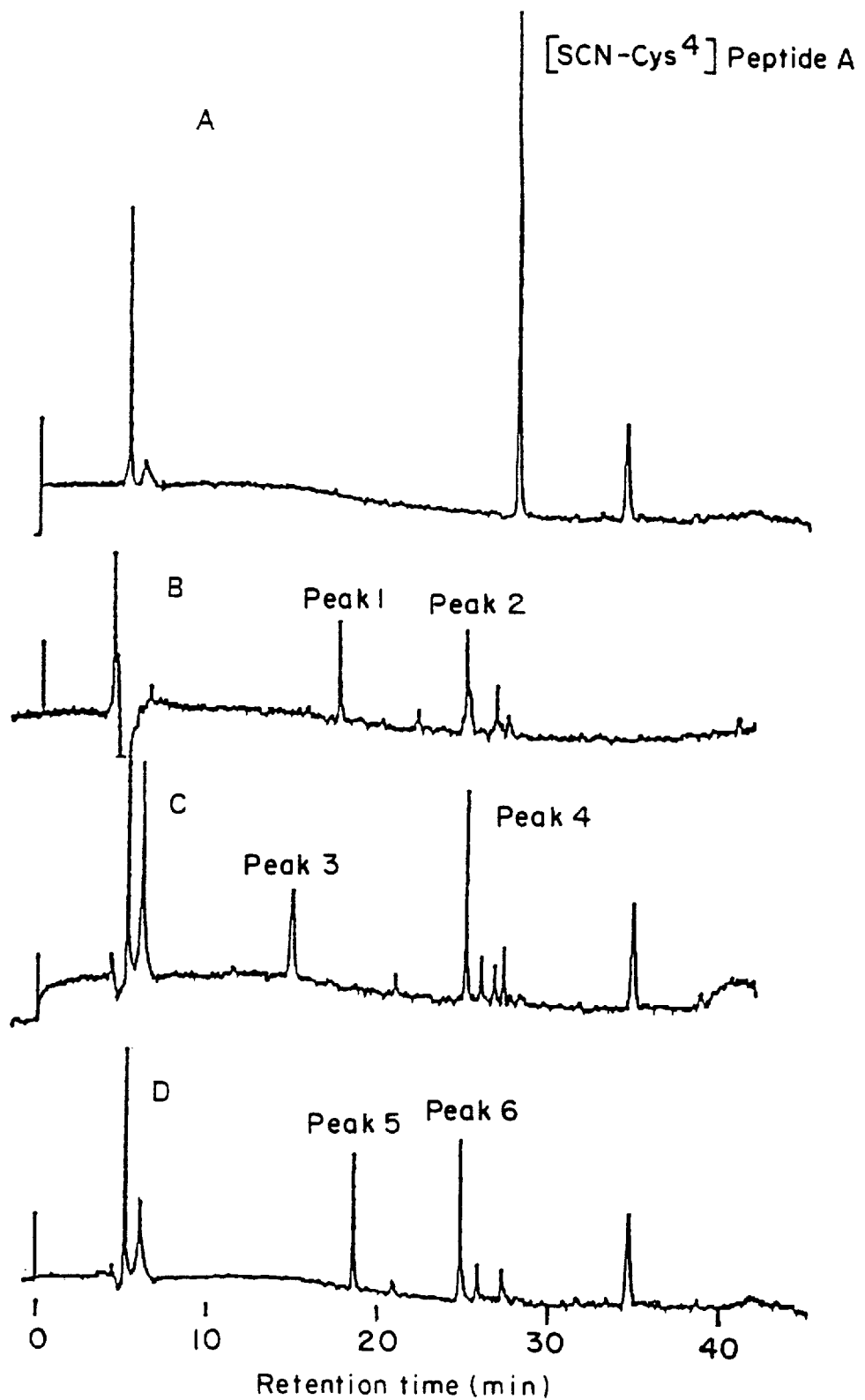
FIG. 33 shows the results of reverse phase high performance liquid chromatography obtained in Examples 10, 11 and 12.

The Cys$^4$ of H-Pro-Tyr-Gly-Cys-Gly-Glu-Glu-Asn-Leu-Val-Tyr-NH$_2$ (Peptide A) (SEQ ID NO:35) was cyanylated in accordance with the method described in Methods in Enzymology, 47, 129–132 (1977) as follows. 677 pg (0.546 μmol) of Peptide A was dissolved in 2.4 ml of a 6M guanidine-hydrochloric acid (Gu-HCl)-0.2M Tris-acetate buffer (pH 8.0). To this solution was added 154 μg (1 μmol) of dithiothreitol dissolved in 0.1 ml of the same buffer, and the mixture was kept standing at room temperature for 30 minutes. To this mixture was added 1.65 mg (7.5 μmol) of 2-nitro-5-thiocyanobenzoic acid (NTCB) in solution in 0.1 ml of the same buffer. After readjusting to a pH of 8.0, reaction was carried out at room temperature for 15 minutes, followed by the addition of 1 ml of glacial acetic acid to terminate the reaction. The reaction mixture thus obtained was desalted and purified by reverse phase high performance liquid chromatography to yield [S-cyano-Cys$^4$]-Peptide A ([SCN-Cys$^4$]Peptide A). The conditions for reverse phase high performance liquid chromatography were column, YMC A-303 ODS (4.6×250 mm); column temperature, 25° C.; eluent, 0.1% trifluoroacetic acid-99.9% distilled water (Eluent A) and 0.1% trifluoroacetic acid-99.9% acetonitrile (Eluent B); elution program, 0 minute (95% A+5% B), 37 minutes (55% A+45% B) and 35 minutes (20% A+80% B); flow rate, 0.7 ml/min detection wavelength, 280 nm. Under these conditions, [SCN-Cys$^4$]Peptide A was eluted as the main peak at a retention time of 28 minutes (FIG. 33-A). This fraction was separated and used for the following cleavage reaction.

The cleavage reaction to give H-Pro-Tyr-Gly-OH (SEQ ID NO:36) was carried out in a 6 M Gu-HCl-0.1M borate buffer (pH 9.2) in accordance with the method described in Methods in Enzymology, 47, 129–132 (1977). 62 pg of [SCN-Cys$^4$]Peptide A was dissolved in 2 ml of a 6M Gu-HCl-0.1M borate buffer (pH 9.2), followed by reaction at 37° C. for 20 hours, and the reaction was terminated by the addition of 0.2 ml of glacial acetic acid. The reaction broth thus obtained was assayed by reverse phase high performance liquid chromatography (FIG. 33-B). The reverse phase high performance liquid chromatography conditions were the same as those used to obtain [SCN-Cys$^4$] Peptide A.

The [SCN-Cys$^4$]Peptide A eluted at a retention time of 28 minutes (FIG. 33-A) disappeared completely after cleavage reaction, while two major peaks appeared. These peaks, eluted at retention times of 17 minutes and 25 minutes, respectively, were designated as Peak 1 and Peak 2, respectively, and separated and subjected to analyses.

Amino acid compositions were determined using the Hitachi 835 model amino acid analyzer after hydrolyzing in 5.7N hydrochloric acid in a sealed tube under reduced pressure at 110° C. for 24 hours. The amino acid composition of Peak 1 was found to be Pro 0.88 (1), Gly 1.00 (1) and Tyr 0.88 (1), agreeing well with the theoretical amino acid composition of the desired product Pro-Tyr-Gly-OH (SEQ ID NO:36). The amino acid composition of Peak 2 was found to be Asp 1.00 (1), Glu 1.86 (2), Gly 0.84 (1), Val 1.00 (1), Leu 1.03 (1) and Tyr 0.97 (1), agreeing well with the theoretical amino acid composition of the C-terminal fragment of the cleavage products. The molecular weight of Peak 1 was determined by secondary ion mass spectrometry (SIMS) to be mass (m/z):(M+H)$^+$=336, agreeing with the theoretical value of 335.14 for H-Pro-Tyr-Gly-OH.

Example 11

Production of H-Pro-Tyr-Gly-NH2 (SEQ ID NO:36) from H-Pro-Tyr-Gly-Cys-Gly-Glu-Glu-Asn-Leu-Val-Tyr-NH$_2$ (SEQ ID NO:36)

S-cyanylation of the Cys of H-Pro-Tyr-Gly-Cys-Gly-Glu-Glu-Asn-Leu-Val-Tyr-NH2 (Peptide A) (SEQ ID NO:35) and separation of [SCN-Cys$^4$]Peptide A were achieved as directed in Example 10.

To obtain H-Pro-Tyr-Gly-NH$_2$ (SEQ ID NO:36), a aminolysis reaction was carried out in dilute aqueous ammonia. 62 µg of Peptide A was reacted in 0.5 ml of 3M aqueous ammonia at 37° C. for 10 minutes. The same amount of glacial acetic acid was added to terminate the reaction. The reaction mixture thus obtained was assayed by reverse phase high performance liquid chromatography under the conditions shown in Example 10, and the reaction mixture was assayed (FIG. 33-C). After completion of the reaction, the peak of the starting material [SCN-Cys$^4$]Peptide A disappeared completely, while two major peaks appeared. These peaks, eluted at retention times of 14.8 minutes and 25 minutes, respectively, were designated as Peak 3 and Peak 4, respectively, and separated. The amino acid compositions of these peaks were determined in accordance with the method described in Example 10. The amino acid composition of Peak 3 was found to be Gly 1.00 (1), Tyr 0.98 (1) and Pro 0.96 (1), agreeing well with the theoretical amino acid composition of the desired product H-Pro-Tyr-Gly-NH$_2$ (SEQ ID NO:36). The amino acid composition of Peak 4 was found to be Asp 1.00 (1), Glu 1.92 (2), Gly 0.99 (1), Val 0.84 (1), Leu 0.95 (1) and Tyr 0.99 (1), agreeing with the theoretical amino acid composition of the C-terminal fragment of the cleavage products. The molecular weight of Peak 3 was determined by SIMS to be mass (m/z):(M+H)$^+$=335, agreeing with the theoretical value of 334.16 for H-Pro-Tyr-Gly-NH$_2$ (SEQ ID NO:36).

Example 12

Production of H-Pro-Tyr-Gly-NHC$_2$H$_5$ (SEQ ID NO:36) from H-Pro-Tyr-Gly-Cys-Gly-Glu-Glu-Asn-Leu-Val-Tyr-NH$_2$ (SEQ ID NO:35)

S-cyanylation of the Cys of H-Pro-Tyr-Gly-Cys-Gly-Glu-Glu-Asn-Leu-Val-Tyr-NH$_2$ (Peptide A) (SEQ ID NO:35) and separation of [SCN-Cys$^4$]Peptide A were achieved as directed in Example 10. To obtain H-Pro-Tyr-Gly-NHC$_2$H$_5$, a cleavage reaction was carried out as follows. 62 µg of [SCN-Cys$^4$]Peptide A was reacted in 500 µl of 3.1M ethylamine at 37° C. for 10 minutes. The same amount of glacial acetic acid was added to terminate the reaction. The reaction mixture thus obtained was assayed by reverse phase high performance liquid chromatography (FIG. 33-D). The column conditions were the same as in Example 10. After completion of the cleavage reaction, the peak of the starting material [SCN-Cys$^4$]Peptide A disappeared completely, while two major peaks appeared. These peaks, eluted at retention times of 18.6 minutes and 25 minutes, respectively, were designated as Peak 5 and Peak 6, respectively, and separated.

The amino acid compositions of these peaks were determined in accordance with the method described in Example 10. The amino acid composition of Peak 5 was found to be Gly 1.00 (1), Tyr 0.95 (1), Pro 1.02 (1) and ethylamine 0.95 (1) (calculated on the assumption that the ninhydrin coloring rate was the same as with Gly), agreeing with the theoretical values of amino acid composition of the desired product H-Pro-Tyr-Gly-NHC$_2$H$_5$ (SEQ ID NO:36). The amino acid composition of Peak 5 was found to be Asp 1.00 (1), Glu 1.89 (2), Gly 0.99 (1), Val 0.84 (1), Leu 0.94 (1) and Tyr 1.00 (1), agreeing with the theoretical values of amino acid composition of the C-terminal fragment of the cleavage products. The molecular weight of Peak 5 was determined by SIMS to be mass (m/z):(M+H)$^+$=363, agreeing with the theoretical value of 362.20 for H-Pro-Tyr-Gly-NHC$_2$H$_5$ (SEQ ID NO:36).

The following references, which are referred to for their disclosures at various points in this application, are incorporated herein by reference.

Science, 198, 1056 (1977)
Methods in Enzymology, 153,46 (1987)
Seikagaku Jikken Koza (Biochemical Experiment), 1, Chemistry of Protein, pp. 247–250, 1976, Tokyo Kagaku Dohjin
Genetic Engineering: Principles and Methods, Plenum Press, vol. 3, pp. 1–32 (1981)
Gene, 33, 103–119 (1985)
Methods in Enymology, 101, 20–78 (1983)
Molecular and General Genetics, 177, 231 (1980)
Methods in Enzymology, 153, 3–11 (1987)
Gene, 2, 95 (1977)
Gene, 2, 75 (1977)
Gene, 4, 124 (1978)
Gene, 9, 287 (1980)
Gene, 17, 79 (1982)
Gene, 3, 1 (1978)
Seikagaku, 52, 770 (1980)

Journal of Bacteriology, 134, 1141 (1978)
Methods in Engymology, 68, 268 (1979)
Gene, 19, 259 (1982)
Proc. Natl. Acad. Sci. USA, 71,4579 (1974)
Proc. Natl. Acad. Sci. USA, 72, 3461 (1975)
Gene, 1, 255 (1977)
Science, 196, 161 (1977)
Journal of Virology, 29, 555 (1979)
Proc. Natl. Acad. Sci. USA, 74,4266–4270 (1977)
Cell, 16, 815–825 (1979)
Nature, 280, 35 (1979)
J. Mol. Biol., 166 477–535 (1983)
Gene, 56,125–135 (1987)
J. Mol. Biol., 189,113–130 (1986)
Proc. Natl. Acad. Sci. USA, 69,2110 (1972)
Proc. Natl. Acad. Sci. USA, 60, 160 (1968)
Nucleic Acids Research, 9, 309 (1981)
J. Mol. Biol., 120, 517 (1978)
J. Mol. Biol., 41, 459 (1969)
Genetics, 39, 440 (1954)
Cell, 25, 713 (1981)
Proc. Natl. Acad. Sci. USA, 73, 4174 (1976)
Gene, 24, 255(1983)
Journal of Bacteriology, 95, 87 (1984)
Proc. Natl. Acad. Sci. USA, 75, 1929 (1978)
Proc. Natl. Acad. Sci. USA, 77, 2173 (1980)
Genetics, 85, 23 (1976)
Proc. Natl. Acad. Sci. USA, 78, 2258 (1981)
Cell, 23, 175 (1981)
Japanese Journal of Clinical Medicine, 21, 1209 (1963)
Journal of Experimental Medicine, 108, 945 (1985)
Journal of National Cancer Institute, 4, 165 (1943)
Proceedings of the Society for Experimental Biology and Medicine, 94, 532 (1957)
J. Mol. Biol., 189, 113–130 (1986)
Molecular & General Genetics, 168, 111 (1979)
Proc. Natl. Acad. Sci. USA, 75, 1929 (1978)
Virology, 52, 456 (1973)
Journal of Experiments in Molecular Genetics, 431, 433, Cold Spring Harbor Laboratory, 1972
Proc. Natl. Acad. Sci. USA, 77, 4505 (1980)
Virology, 8, 396 (1959)
Journal of the American Medical Association, 199, 519 (1967)
Proceeding of the Society for the Biological Medicine, 73, 1 (1950)
Advances in Enymology, 32, 221–296 (1969)
Biochem. Biophys. Res. Commun. 151, 701–708 (1988)
EP-A-281,822
European Journal of Biochemistry, 188, 239–245 (1990)
J. Mol. Biol. 110, 119 (1977)
J. Mol. Biol. 166, 557 (1983)
Molecular Cloning, Cold Spring Harbor Laboratory, 368–369, 1982
Methods in Enzymology, 195, 60–89 (1990)
Methods in Enzymology, 153, 3–11 (1987)
Nature, 227, 680 (1970)
Journal of Chemical Society Chemical Communication, 1967, 21–22
Biochemistry, 13, 1–11 (1974)
Advance of Enzymology, 32, 221–296 (1969)
Methods in Enzymology, 47, 129–132 (1977)

What we claim is:

1. A method for producing human parathyroid hormone (1-34), which comprises cultivating a transformant having a vector carrying a gene coding human parathyroid hormone (1-84) wherein valine at amino acid 35 of said hormone has been replaced with cysteine, expressing said human parathyroid hormone, subjecting the expressed hormone to a reaction for cleaving the peptide linkage on the amino group side of cysteine residue, wherein the reaction for cleaving the peptide linkage is conducted by a cyanylation reaction by using S-cyanylation reagent followed by hydrolysis to produce a carboxy peptide and isolating human parathyroid hormone (1-34).

* * * * *